(12) United States Patent
Voytas et al.

(10) Patent No.: US 11,384,360 B2
(45) Date of Patent: Jul. 12, 2022

(54) GENE TARGETING IN PLANTS USING DNA VIRUSES

(71) Applicant: Regents of the University of Minnesota, Minneapolis, MN (US)

(72) Inventors: Daniel F. Voytas, Falcon Heights, MN (US); Nicholas J. Baltes, Maple Grove, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 0 days.

(21) Appl. No.: 17/010,239

(22) Filed: Sep. 2, 2020

(65) Prior Publication Data

US 2021/0054388 A1    Feb. 25, 2021

Related U.S. Application Data

(63) Continuation of application No. 14/409,148, filed as application No. PCT/US2013/046495 on Jun. 19, 2013, now abandoned.

(60) Provisional application No. 61/790,581, filed on Mar. 15, 2013, provisional application No. 61/772,704, filed on Mar. 5, 2013, provisional application No. 61/661,542, filed on Jun. 19, 2012.

(51) Int. Cl.
   *C12N 15/82*    (2006.01)
   *C12N 15/90*    (2006.01)
   *C12N 9/22*     (2006.01)

(52) U.S. Cl.
   CPC ........... *C12N 15/8203* (2013.01); *C12N 9/22* (2013.01); *C12N 15/902* (2013.01); *C12N 2750/12043* (2013.01); *C12N 2999/007* (2013.01)

(58) Field of Classification Search
   None
   See application file for complete search history.

(56) References Cited

U.S. PATENT DOCUMENTS

| | | |
|---|---|---|
| 4,179,337 A | 12/1979 | Davis et al. |
| 4,683,195 A | 7/1987 | Mullis et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,959,317 A | 9/1990 | Sauer |
| 4,975,374 A | 12/1990 | Goodman et al. |
| 5,006,333 A | 4/1991 | Saifer et al. |
| 5,013,659 A | 5/1991 | Bedbrook et al. |
| 5,162,602 A | 11/1992 | Somers et al. |
| 5,204,253 A | 4/1993 | Sanford et al. |
| 5,276,268 A | 1/1994 | Strauch et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,501,967 A | 3/1996 | Offringa et al. |
| 5,538,880 A | 7/1996 | Lundquist et al. |
| 5,554,798 A | 9/1996 | Lundquist et al. |
| 5,561,236 A | 10/1996 | Leemans et al. |
| 5,591,616 A | 1/1997 | Hiei et al. |
| 5,767,366 A | 6/1998 | Sathasivan et al. |
| 5,792,640 A | 8/1998 | Chandrasegaran |
| 5,879,903 A | 3/1999 | Strauch et al. |
| 5,928,937 A | 7/1999 | Kakefuda et al. |
| 6,084,155 A | 7/2000 | Volrath et al. |
| 6,326,166 B1 | 12/2001 | Pomerantz et al. |
| 6,329,571 B1 | 12/2001 | Hiei |
| 6,368,227 B1 | 4/2002 | Olson |
| 6,392,121 B1 | 5/2002 | Mason et al. |
| 6,451,732 B1 | 9/2002 | Beckett et al. |
| 6,451,735 B1 | 9/2002 | Ottaway et al. |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,001,768 B2 | 2/2006 | Wolffe |
| 7,013,219 B2 | 3/2006 | Case et al. |
| 7,067,722 B2 | 6/2006 | Fillatti |
| 7,070,934 B2 | 7/2006 | Cox, III et al. |
| 7,163,824 B2 | 1/2007 | Cox, III et al. |
| 7,189,691 B2 | 3/2007 | Hemenway |
| 7,220,719 B2 | 5/2007 | Case et al. |
| 7,262,054 B2 | 8/2007 | Jamieson et al. |
| 7,262,267 B1 | 8/2007 | Hildt et al. |
| 7,273,923 B2 | 9/2007 | Jamieson et al. |
| 7,285,416 B2 | 10/2007 | Choo et al. |
| 7,361,635 B2 | 4/2008 | Miller et al. |
| 7,521,241 B2 | 4/2009 | Choo et al. |
| 7,608,752 B2 | 10/2009 | Lyznik et al. |
| 7,842,489 B2 | 11/2010 | Arnould et al. |
| 8,058,506 B2 | 11/2011 | Klimyuk et al. |
| 8,106,255 B2 | 1/2012 | Carroll |

(Continued)

FOREIGN PATENT DOCUMENTS

| | | |
|---|---|---|
| CN | 10188909 | 11/2010 |
| CN | 103343120 | 10/2013 |

(Continued)

OTHER PUBLICATIONS

Mor et al 2003 (Biotechnology and Bioengineering 81:4, p. 431-437) (Year: 2003).*

(Continued)

*Primary Examiner* — Matthew R Keogh
(74) *Attorney, Agent, or Firm* — Fish & Richardson P.C.

(57) ABSTRACT

Systems and methods for gene targeting in plants, including systems and methods that include the use of geminiviruses and customizable endonucleases.

6 Claims, 43 Drawing Sheets

Specification includes a Sequence Listing.

(56) References Cited

U.S. PATENT DOCUMENTS

| | | |
|---|---|---|
| 8,420,782 B2 | 4/2013 | Bonas et al. |
| 8,440,431 B2 | 5/2013 | Voytas et al. |
| 8,440,432 B2 | 5/2013 | Voytas et al. |
| 8,450,471 B2 | 5/2013 | Voytas et al. |
| 8,586,363 B2 | 11/2013 | Voytas et al. |
| 8,697,359 B1 | 4/2014 | Zhang |
| 8,697,853 B2 | 4/2014 | Voytas et al. |
| 9,035,129 B2 | 5/2015 | Bilyeu et al. |
| 9,187,755 B2 | 11/2015 | Samuel et al. |
| 9,198,365 B2 | 12/2015 | Bilyeu et al. |
| 10,457,950 B2 | 10/2019 | Malcuit et al. |
| 2001/0016956 A1 | 8/2001 | Ward et al. |
| 2004/0101880 A1 | 5/2004 | Rozwadowski et al. |
| 2004/0261149 A1 | 12/2004 | Fauquet et al. |
| 2005/0042603 A1 | 2/2005 | Wang |
| 2005/0064474 A1 | 3/2005 | Umov et al. |
| 2005/0091706 A1 | 4/2005 | Klimyuk et al. |
| 2007/0141038 A1 | 6/2007 | Choulika et al. |
| 2008/0015137 A1 | 1/2008 | Chook |
| 2009/0013315 A1 | 1/2009 | Sharma et al. |
| 2009/0060921 A1 | 3/2009 | Dickey et al. |
| 2009/0100536 A1 | 4/2009 | Adams et al. |
| 2009/0133152 A1* | 5/2009 | Lyznik ............... A01H 1/02 800/275 |
| 2009/0133158 A1 | 5/2009 | Lahaye et al. |
| 2009/0271881 A1 | 10/2009 | Arnould et al. |
| 2009/0305402 A1 | 12/2009 | Liljedahl et al. |
| 2010/0003111 A1 | 1/2010 | Yeo et al. |
| 2010/0076057 A1 | 3/2010 | Sontheimer et al. |
| 2010/0132069 A1 | 5/2010 | Lahaye et al. |
| 2010/0154081 A1 | 6/2010 | Weterings et al. |
| 2011/0014594 A1 | 1/2011 | Chen et al. |
| 2011/0041195 A1 | 2/2011 | Doyon |
| 2011/0059160 A1 | 3/2011 | Essner et al. |
| 2011/0129898 A1 | 6/2011 | Doyon et al. |
| 2011/0136895 A1 | 6/2011 | Gregory et al. |
| 2011/0145940 A1 | 6/2011 | Voytas et al. |
| 2011/0158957 A1 | 6/2011 | Bonini et al. |
| 2011/0167521 A1 | 7/2011 | DeKelver et al. |
| 2011/0177557 A1 | 7/2011 | Edenhofer et al. |
| 2011/0201055 A1 | 8/2011 | Doyon et al. |
| 2011/0201118 A1 | 8/2011 | Yang et al. |
| 2011/0203012 A1 | 8/2011 | Dotson et al. |
| 2011/0207221 A1 | 8/2011 | Cost et al. |
| 2011/0239315 A1 | 9/2011 | Bonas et al. |
| 2011/0247089 A1 | 10/2011 | Doyon |
| 2011/0265198 A1 | 10/2011 | Gregory et al. |
| 2011/0269234 A1 | 11/2011 | Doyon et al. |
| 2011/0287545 A1 | 11/2011 | Cost et al. |
| 2011/0301073 A1 | 12/2011 | Gregory et al. |
| 2012/0042411 A1 | 2/2012 | Malcuit |
| 2012/0064620 A1 | 3/2012 | Bonas et al. |
| 2012/0110685 A1 | 5/2012 | Bonas et al. |
| 2012/0122205 A1 | 5/2012 | Bonas et al. |
| 2012/0135021 A1 | 5/2012 | Torens Madrazo et al. |
| 2012/0178131 A1 | 7/2012 | Voytas et al. |
| 2012/0178169 A1 | 7/2012 | Voytas et al. |
| 2012/0214228 A1 | 8/2012 | Voytas et al. |
| 2012/0246764 A1 | 9/2012 | Hlubek et al. |
| 2012/0284877 A1 | 11/2012 | Hlubek et al. |
| 2012/0324603 A1 | 12/2012 | Hlubek et al. |
| 2013/0122581 A1 | 5/2013 | Voytas et al. |
| 2014/0068797 A1 | 3/2014 | Doudna |
| 2014/0090116 A1 | 3/2014 | Ainley et al. |
| 2014/0273235 A1 | 9/2014 | Voytas et al. |
| 2014/0335592 A1 | 11/2014 | Voytas et al. |
| 2014/0335618 A1 | 11/2014 | Voytas et al. |
| 2015/0067922 A1 | 3/2015 | Yang |
| 2015/0079681 A1 | 3/2015 | Zhang |
| 2015/0167000 A1 | 6/2015 | Voytas |
| 2016/0237451 A1 | 8/2016 | Voytas |
| 2017/0175140 A1 | 6/2017 | Hummel et al. |
| 2019/0249183 A1 | 8/2019 | Humanes |
| 2021/0002656 A1 | 1/2021 | Voytas et al. |

FOREIGN PATENT DOCUMENTS

| | | |
|---|---|---|
| EP | 0242246 | 10/1987 |
| EP | 2181193 | 6/2008 |
| EP | 2206723 | 7/2010 |
| EP | 2392208 | 12/2011 |
| EP | 2562260 | 2/2013 |
| EP | 3401400 | 3/2013 |
| EP | 2389441 | 8/2016 |
| GB | 2500812 | 10/2013 |
| JP | 2002-534104 | 10/2002 |
| JP | 2003-512061 | 4/2003 |
| JP | 2003-527093 | 9/2003 |
| JP | 2006-505287 | 2/2006 |
| JP | 2007-524392 | 8/2007 |
| JP | 2009-159967 | 7/2009 |
| JP | 2011-147448 | 8/2011 |
| JP | 2012-523234 | 10/2012 |
| JP | 2013-513389 | 4/2013 |
| JP | 2015-514015 | 5/2015 |
| JP | 2015-523856 | 8/2015 |
| JP | 2016-521561 | 7/2016 |
| WO | WO 1994/18313 | 8/1994 |
| WO | WO 1995/09233 | 4/1995 |
| WO | WO 2001/38514 | 5/2001 |
| WO | WO 2002/034771 | 5/2002 |
| WO | WO 2003/083118 | 10/2003 |
| WO | WO 2003/087341 | 10/2003 |
| WO | WO 2004/067736 | 8/2004 |
| WO | WO 2007/060495 | 5/2007 |
| WO | WO 2008/021207 | 2/2008 |
| WO | WO 2008/141806 | 11/2008 |
| WO | WO 2008/148223 | 12/2008 |
| WO | WO 2009/095793 | 8/2009 |
| WO | WO 2009/130695 | 10/2009 |
| WO | WO 2010/079430 | 7/2010 |
| WO | WO 2010/091018 | 8/2010 |
| WO | WO 2010/118077 | 10/2010 |
| WO | WO 2010/145846 | 12/2010 |
| WO | WO 2011/005998 | 1/2011 |
| WO | WO 2011/017293 | 2/2011 |
| WO | WO 2011/019385 | 2/2011 |
| WO | WO 2011/072246 | 6/2011 |
| WO | WO 2011/100058 | 8/2011 |
| WO | WO 2011/117249 | 9/2011 |
| WO | WO 2011/143124 | 11/2011 |
| WO | WO 2011/146121 | 11/2011 |
| WO | WO 2011/154393 | 12/2011 |
| WO | WO 2012/013717 | 2/2012 |
| WO | WO 2012/058458 | 5/2012 |
| WO | WO 2013/071440 | 5/2012 |
| WO | WO 2012/106105 | 8/2012 |
| WO | WO 2012/129443 | 9/2012 |
| WO | WO 2012/138927 | 10/2012 |
| WO | WO 2013/009525 | 1/2013 |
| WO | WO 2013/050155 | 4/2013 |
| WO | WO 2013/176772 | 11/2013 |
| WO | WO 2013/192278 | 12/2013 |
| WO | WO 2014/039692 | 3/2014 |
| WO | WO 2014/039702 | 3/2014 |
| WO | WO 2014/099744 | 4/2014 |
| WO | WO 2014/065596 | 5/2014 |
| WO | WO 2014/089290 | 6/2014 |
| WO | WO 2014/093712 | 6/2014 |
| WO | WO 2014/144155 | 9/2014 |
| WO | WO 2014/186585 | 11/2014 |
| WO | WO 2014/191521 | 12/2014 |
| WO | WO 2014/194190 | 12/2014 |
| WO | WO 2014/199358 | 12/2014 |
| WO | WO 2015/026883 | 2/2015 |

OTHER PUBLICATIONS

Supplementary Materials for Cong et al., "Multiplex Genome Engineering Using CRISPR/Cas Systems," Science 339(6121):819-23, Feb. 2013, 28 pages.

(56) References Cited

OTHER PUBLICATIONS

Supplementary Materials for Mali et al., "RNA-guided human genome engineering via Cas9," Science 339(6121):823-6, Feb. 2013, 36 pages.
Avesani et al., "Stability of Potato virus expression vectors is related to insert size: implications for replication models and risk assessment," Transgenic Research, 16(5):587-597, Oct. 2007.
Barrangou, "RNA-mediated programmable DNA cleavage," Nat. Biotechnology, 30(9):836-838, Sep. 2012.
Chen et al., "Geminiviral vectors based on bean yellow dwarf virus for production of vaccine antigens and monoclonal antibodies in plants," Hum. Vaccines, 7(3):331-338, Mar. 2011.
Hickey et al., "Transgene regulation in plants by alternative splicing of a suicide exon," Nucleic Acids Research, 40(10):4701-4710, May 2012.
Matoba et al., "Recombinant Protein Expression in Nicotiana," Methods Mol. Biology, 701:199-219, Dec. 2010.
Regnard et al., "High level protein expression in plants through the use of novel autonomously replicating geminivirus shuttle vector," Plant Biotechnol. Journal, 8(1):38-46, Jan. 2010.
Supplementary Materials for Jinek et al., "A programmable dual-RNA-guided DNA endonuclease in adaptive bacterial immunity," Science, 337(6096):816-21, Aug. 2012, 37 pages.
Supplementary Materials for Townsend et al., "High-frequency modification of plant genes using engineered zinc-finger nucleases," Nature, 459(7245):442-5, May 2009, 12 pages.
Supplementary Materials for Zhang et al., "Transcription activator-like effector nucleases enable efficient plant genome engineering," Plant Physiol., 161(1):20-7, Jan. 2013, 7 pages.
Trejo-Saavedra et al., "The infective cycle of Cabbage leaf curl virus (CaLCuV) is affected by Crumpled Leaf (CRL) gene in *Arabidopsis thaliana*," Virol. Journal, 6:169, Oct. 20, 2009, 13 pages.
Vainstein et al., "Permanent Genome Modifications in Plant Cells by Transient Viral Vectors," Proc. 24th Int. Eucarpia Symp. Section Ornamentals, Acta Hort., ISHS 2012, 953:31-36, Sep. 2012.
Vainstein et al., "Permanent genome modifications in plant cells by transient viral vectors," Trends Biotechnology, 29(8):363-369, Aug. 2011.
Bortesi et al., "The CRISPR/Cas9 system for plant genome editing and beyond," Biotechnol. Advances, 33(1):41-52, Dec. 20, 2014.
GenBank Accession No. DQ458791.1, "Chickpea chlorotic dwarf virus, complete genome," dated Mar. 15, 2013, 2 pages.
Gleba et al., "Engineering viral expression vectors for plants: the 'full virus' and the 'deconstructed virus' strategies," Curr. Opin. Plant Biology, 7(2):182-188, Apr. 2004.
Mor et al., "Geminivirus vectors for high-level expression of foreign proteins in plant cells," Biotechnol. Bioengineering, 81(4):430-437, Feb. 20, 2003.
Peyret et al., "When plant virology met Agrobacterium: the rise of the deconstructed clones," Plant Biotechnol. Journal, 13(8):1121-1135, Jun. 12, 2015.
U.S. Appl. No. 14/291,605, filed May 30, 2014, Yang et al.
U.S. Appl. No. 14/898,208, filed Dec. 14, 2015, Voytas et al.
U.S. Appl. No. 61/225,043, filed Jul. 13, 2009, Bonas et al.
U.S. Appl. No. 61/716,256, filed Oct. 19, 2012, Jinek et al.
U.S. Appl. No. 61/758,624, filed Jan. 30, 2013, Chen et al.
U.S. Appl. No. 61/790,694, filed Mar. 15, 2013, Voytas et al.
U.S. Appl. No. 61/937,045, filed Feb. 7, 2014, Cigan.
"Expression of Useful Genes with Viral Vector," Kagaku to Seibutsu, Chemicals, Organism, 41:183-189, 2003, 1 page.
"TAL effector nucleases," Nature Reprint Collection [online]. Oct. 2011, [retrieved on Mar. 14, 2012]. Retrieved from the Internet: URL <http://www.nature.com/nbt/collections/talen/index.html>, 32 pages, Marshall (ed.).
Alam and Sittman, "Characterization of the cytotoxic effect of a chimeric restriction enzyme, H1°-FokI," Gene. Ther. Mol. Biol., 10:147-60, 2006.
Alam, "Characterization of the cytotoxic effect of a novel chimeric restriction nuclease, H1°-FokI, in mouse fibroblast cells: Implications for chromatin mapping and gene therapy studies," Ph.D. Thesis, The University of Mississippi Medical Center, 223 pages, 2006.
Ali et al., "Activity and Specificity of TRV-Mediated Gene Editing in Plant" Plant Sig. Beh., 10(10):e1044191-1-4, Oct. 2015.
Ali et al., "Efficient Virus-Mediated Genome Editing in Plants Using the CRISPR/Cas9 System," Mol. Plant, 8:1288-91, Aug. 2015.
Al-Saadi et al., "All five host-range variants of Xanthomonas citri carry one pthA homolog with 17.5 repeats that determines pathogenicity on citrus, but none determine host-range variation," Mol. Plant Microbe. Interact., 20(8): 934-43, 2007.
Andrieu et al., "An in planta, Agrobacterium-mediated transient gene expression method for inducing gene silencing in rice (*Oryza sativa* L.) leaves," Rice (NY)., 5(1):23, Aug. 2012.
Anonymous Mar. 13, 2013 "RNA mediated DNA cleavage in engineering Agrobacterium and plant genomes".
Antony et al., "Rice xa13 recessive resistance to bacterial blight is defeated by induction of the disease susceptibility gene Os-11N3," Plant Cell, 22(11):3864-76, 2010.
Antony, "Molecular basis of avrXa7 mediated virulence in bacterial blight of rice," [abstract of dissertation] Kansas State University, 99 pages, 2010.
Arimondo et al., "Exploring the cellular activity of camptothecin-triple-helix-forming oligonucleotide conjugates," Mol. Cell Biol., 26:324-33, 2006.
Ascencio-Ibanez et al., "DNA abrasion onto plants is an effective method for geminivirus infection and virus-induced gene silencing," J. Virol. Methods, 142(1-2):198-203, Jun. 2007.
Athinuwat et al., "Xanthomonas axonopodis pv. glycines soybean cultivar virulence specificity is determined by avrBs3 homolog avrXg1," Phytopathology, 99(8):996-1004, 2009.
Bai et al., "Xanthomonas oryzae pv. oryzae a virulence genes contribute differently and specifically to pathogen aggressiveness," Mol. Plant Microbe. Interact., 13(12):1322-9, 2000.
Baker, "Gene-editing nucleases," Nature Methods, 9:23-26, Dec. 2011.
Ballvora et al., "Genetic mapping and functional analysis of the tomato Bs4 locus governing recognition of the *Xanthomonas campestris* pv. *vesicatoria* AvrBs4 protein," Mol. Plant Microbe. Interact., 14(5):629-38, 2001.
Baltes et al., "DNA replicons for plant genome engineering," Plant Cell, 26(1):151-63, Jan. 2014.
Bashirullah et al., "Spatial and temporal control of RNA stability," Proc. Natl. Acad. Sci. U.S.A., 98(13):7025-8, Jun. 2001.
Baulcombe, "RNA silencing in plants," Nature., 431:356-363, Sep. 16, 2004.
Behrouzi et al., "Cooperative tertiary interaction network guides RNA folding," Cell., 149:348-357, Apr. 13, 2012.
Belhaj et al., "Plant genome editing made easy: targeted mutagenesis in model and crop plants using the CRISPR/Cas system," Plant Methods, 9:(1)39, Dec. 2013.
Beretta et al., "Tethering a type IB topoisomerase to a DNA site by enzyme fusion to a heterologous site-selective DNA-binding protein domain," Cancer Res., 59:3689-97, 1999.
Bethke and Busse, "Validation of a simple, colorimetric, microplate assay using amplex red for the determination of glucose and sucrose in potato tubers and other vegetables," Am. J. Pot Res., 85(6):414-421, Dec. 2008.
Beurdeley et al., "Compact designer TALENs for efficient genome engineering," Nat. Commun., 4:1762, Apr. 2013.
Beuselinck et al., "An Assessment of Phenotype Selection for Linolenic Acid Using Genetic Markers," Crop Sci., 46(2):747-50 Mar. 2006.
Bhaskar et al., "Suppression of the vacuolar invertase gene prevents cold-induced sweetening in potato," Plant Physiol., 154(2):939-948, Oct. 2010.
Bhushan et al., "The role of the N-terminal domain of chloroplast targeting peptides in organellar protein import and miss-sorting," FEBS Lett. 580(16):3966-72, Jul. 2006.
Bian et al., "Analysis of silencing escape of tomato leaf curl virus: an evaluation of the role of DNA methylation," Mol. Plant Microbe. Interact., 19(6):614-24, Jun. 2006.

(56) References Cited

OTHER PUBLICATIONS

Bibikova et al., "Enhancing gene targeting with designed zinc finger nucleases," Science, 300(5620):764, 2003.
Bibikova et al., "Stimulation of homologous recombination through targeted cleavage by chimeric nucleases," Mol. Cell Biol., 21(1): 289-97, 2001.
Bitinaite et al., "FokI dimerization is required for DNA cleavage," Proc. Natl. Acad. Sci. USA., 95:10570-5, 1998.
Boch and Bonas. "Xanthomonas AvrBs3 family-type III effectors: discovery and function," Annu Rev Phytopathol, 48, 419-436, 2010.
Boch et al., "Breaking the code of DNA binding specificity of TAL-type III effectors," Science, 326:1509-12, 2009.
Boch et al., "Molecular characterization of three AvrBs3-like effectors from the *Arabidopsis* pathogen Xanthomonas campestris pv. armoraciae," (abstract), XIV International Congress on Molecular Plant-Microbe Interactions, Quebec City, Canada, Jul. 19-23, 2009, 2 pages.
Bogdanove and Voytas, "TAL effectors: customizable proteins for DNA targeting," Science, 333(6051):1843-6, Sep. 2011.
Bogdanove et al., "TAL effectors: finding plant genes for disease and defense," Cur. Opin. Plant Biol., 13:394-401, 2010.
Boller and He, "Innate immunity in plants: an arms race between pattern recognition receptors in plants and effectors in microbial pathogens," Science, 324:742-4, 2009.
Bonas et al., "Genetic and Structural characterization of the avirulence gene avrBs3 from Xanthomonas campestris pv. Vesicatoria," Mol. Gen. Genet., 218:I27-36, 1989.
Bonas et al., "How the bacterial plant pathogen Xanthomonas campestris pv. vesicatoria conquers the host," Mol. Plant. Pathol., 1(1):73-6, 2000.
Bonas et al., "Resistance in tomato to Xanthomonas campestris pv vesicatoria is determined by alleles of the pepper-specific avirulence gene avrBs3," Mol. Gen. Genet., 238(1-2):261-9, 1993.
Bonas, "How Xanthomonas manipulates the plant cell," (abstract), XIV International Congress on Molecular Plant-Microbe Interactions, Quebec City, Canada, Jul. 19-23, 2009, 2 pages.
Borevitz et al., "Activation tagging identifies a conserved MYB regulator of phenylpropanoid biosynthesis," Plant Cell, 12:2383-94, 2000.
Busk, "Regulatory elements in vivo in the promoter of the abscisic acid responsive gene rab17 from maize," Plant J, 11:1285-95, 1997.
Butler et al., "Geminivirus-mediated genome editing in potato (*Solanum tuberosum* L.) using sequence-specific nucleases," Front. Plant Sci., 7:1045, Jul. 2016.
Büttner and Bonas, "Getting across—bacterial type III effector proteins on their way to the plant cell," EMBO J., 21(20):5313-22, 2002.
Büttner et al., "Functional analysis of HrpF, a putative type III translocon protein from Xanthomonas campestris pv. vesicatoria," J. Bacteriol., 184(9):2389-98, 2002.
Büttner et al., "HpaB from Xanthomonas campestris pv. vesicatoria acts as an exit control protein in type III-dependent protein secretion," Mol. Microbiol., 54(3):755-68, 2004.
Büttner et al., "Targeting of two effector protein classes to the type III secretion system by a HpaC- and HpaB-dependent protein complex from Xanthomonas campestris pv. vesicatoria," Mol. Microbiol, 59(2):513-27, 2006.
Canteros et al., "A gene from Xanthomonas campestris pv. vesicatoria that determines avirulence in tomato is related to avrBs3," Mol. Plant Microbe. Interact., 4(6):628-32, 1991.
Carlson et al., "Targeting DNA With Fingers and TALENs," Mol Ther Nucl Acids, 1 :e3, 2012.
Cathomen et al., "Zinc-finger nucleases: the next generation emerges," Mol Ther, 16(7):1200-7, 2008.
Cavalier et al., "Disrupting Two *Arabidopsis thaliana* Xylosyltransferase Genes Results in Plant Deficient in Xyloglucan, a Major Primary Cell Wall Component," The Plant Cell, 20:1519-1537, Jun. 2008.
Čermák et al., "High-frequency, precise modification of the tomato genome," Genome Biol., 16(1):232, Dec. 2015.

Čermák et al., "Efficient design and assembly of custom TALEN and other TAL effector-based constructs for DNA targeting," Nucl. Acids. Res., 39(12):e82, Apr. 2011.
Čermák et al.,"Engineered TAL effector nucleases: new tools for genome editing," Poster and Abstract, Northwest Genome Engineering Consortium Workshop on Genome Engineering, 3 pages, 2010.
Certo et al., "Coupling endonucleases with DNA end-processing enzymes to drive gene disruption," Nat. Methods, 9(10):972-5, Oct. 2012.
Chang et al., "Genome editing with RNA-guided Cas9 nuclease in zebrafish embryos," Cell Res., 23(4):465-472, Apr. 2013.
Chevalier et al., "Design, activity, and structure of a highly specific artificial endonuclease," Mol. Cell, 10(4):895-905, 2002.
Cho et al., "Targeted genome engineering in human cells with the Cas9 RNA-guided endonuclease," Nat Biotechnol., 31(3):230-232, Mar. 2013.
Choi et al., "A plant virus vector for systemic expression of foreign genes in cereals," Plant J., 23:547-55, Aug. 2000.
Choo et al., "In vivo repression by a site-specific DNA-binding protein designed against an oncogenic sequences," Nature, 372(6507):642-5, 1994.
Choulika et al., "Induction of homologous recombination in mammalian chromosomes by using the I-SceI system of *Saccharomyces cerevisiae*," Mol. Cell Biol., 15(4):1968-73, 1995.
Christian et al., "Targeting DNA double-strand breaks with TAL effector nucleases," Genetics, 186(2):757-61, Oct. 2010.
Christian et al., "Fusions of TAL effectors to the FokI endonuclease confer site specificity in DNA cleavage," Poster and Abstract, IAPB 12th World Congress and In Vitro Biology Meeting, 4 pages, Jun. 2010.
Christou, "Rice transformation: bombardment," Plant Mol. Biol., 35(1-2):197-203, Sep. 1997.
Chugh et al., "Translocation of cell-penetrating peptides and delivery of their cargoes in triticale microspores," Plant Cell Rep., 28(5):801-10, May 2009.
Chylinski et al., "The tracrRNA and Cas9 families of type II CRISPR-Cas immunity systems," RNA biology, 10(5):726-37, May 2013.
Clough and Bent, "Floral dip: a simplified method for Agrobacterium-mediated transformation of *Arabidopsis thaliana*," Plant J., 16(6):735-743, Dec. 1, 1998.
Cocozaki et al., "Structure of the Cmr2 subunit of the CRISPR-Cas RNA silencing complex," Structure, 20(3):545-53, Mar. 2012.
Cole et al., "The Jpred 3 secondary structure prediction server," Nucl Acids Res, 36:W197-W201, 2008.
Cong et al., "Multiplex Genome Engineering Using CRISPR/Cas Systems," Science 339(6121):819-23, Feb. 2013.
Comai et al., "Expression in plants of a mutant aroA gene from *Salmonella typhimurium* confers tolerance to glyphosate," Nature, 317(24): 741-744, 1985.
Cornelis, "The type III secretion injectisome," Nat. Rev. Microbiol., 4:811-25, 2006.
Curtin et al., "Targeted mutagenesis of duplicated genes in soybean with zine-finger nucleases," Plant Physiology, 156(2):466-473, Jun. 2011.
De Feyter et al., "Gene-for genes interactions between cotton R genes and Xanthomonas campestris pv. malvacearum avr genes," Mol. Plant Microbe. Interact., 6(2):225-37, 1993.
DeFrancesco, "Move over ZFNs," Nat. Biotechnol., 29: 681-4, 2011.
Desjarlais and Berg, "Toward rules relating zinc finger protein sequences and DNA binding site preferences," Proc. Natl. Acad. Sci. USA., 89:7345-9, 1992.
Dicarlo et al., "Genome engineering in *Saccharomyces cerevisiae* using CRISPR-Cas systems," Nucleic Acids Res., 41(7):4336-4343, Mar. 2013.
Domingues et al., "The Xanthomonas citri effector protein PthA interacts with citrus proteins involved in nuclear transport, protein folding and ubiquitination associated with DNA repair," Mol. Plant Pathol., 11(5):663-75, Sep. 2010.

(56) References Cited

OTHER PUBLICATIONS

Dormann et al., "Arginine methylation next to the PY-NLS modulates Transportin binding and nuclear import of FUS," EMBO J., 31(22): 4258-75, Nov. 2012.
Doyle et al., "TAL Effector-Nucleotide Targeter (TALE-NT) 2.0: tools for TAL effector design and target prediction," Nucleic Acids Res, 40:W117-122, Jun. 2012.
Draffehn et al., "Natural diversity of potato (*Solanum tuberosum*) invertases," BMC Plant Biol., 10:271, Dec. 2010.
Dugdale et al., "In plant activation: an inducible, hyperexpression platform for recombinant protein production in plants," Plant Cell, 25(7):2429-2443, Jul. 2013.
Durai et al., "Zinc finger nucleases: custom-designed molecular scissors for genome engineering of plant and mammalian cells," Nucl. Acids Res., 33(1): 5978-90, 2005.
Eisenschmidt et al., "Developing a programmed restriction endonuclease for highly specific DNA cleavage," Nucl. Acids Res., 33:7039-47, 2005.
Engler et al., "A One Pot, One Step, Precision Cloning Method with High Throughput Capability," PLoS One, 3: e3647, 2008.
Engler et al., "Golden Gate Shuffling: A One-Pot DNA Shuffling Method Based on Type IIs Restriction Enzymes," PLoS One, 4:e5553, 2009.
Eudes et al., "Cell-penetrating peptides: From mammalian to plant cells," Plant Signal Behav., 3(8):549-50, Aug. 2008.
Evans et al., "The effects of ribozymes on gene expression in plants," Biochem Soc Trans., 20(4):344S, Nov. 1992.
Fajardo-Sanchez et al., "Computer design of obligate heterodimer meganucleases allows efficient cutting of custom DNA sequences," Nucl. Acids Res., 36(7):2163-73, 2008.
Feng et al., "Efficient genome editing in plants using a CRISPR/Cas system," Cell research, 23(10):1229, Oct. 2013.
Feyter et al., "Expressing ribozymes in plants," Methods Mol Biol., 74:403-415, 1997.
Foley et al., "Rapid Mutation of Endogenous Zebrafish Genes Using Zinc Finger Nucleases Made by Oligomerized Pool ENgineering (OPEN)," PLoS One, 4:e4348, 2009.
Fonfara et al., "Creating highly specific nucleases by fusion of active restriction endonucleases and catalytically inactive homing endonucleases," Nucl. Acids Res., 40(2):847-60, 2011.
Frankel and Pabo, "Cellular uptake of the tat protein from human immunodeficiency virus," Cell, 55(6):1189-93, Dec. 1988.
Fujikawa et al., "Suppression of defense response in plants by the avrBs3/pthA gene family of *Xanthomonas* spp," Mol. Plant Microbe. Interact., 19(3):342-9, 2006.
Gabriel et al., "An unbiased genome-wide analysis of zinc-finger nuclease specificity," Nat. Biotechnol., 29:816-23, 2011.
Gaj et al., "ZFN, TALEN, and CRISPR/Cas-based methods for genome engineering," Trends in biotechnology, 31(7):397-405, Jul. 2013.
Gaj et al., "Targeted gene knockout by direct delivery of zinc-finger nuclease proteins," Nat. Methods, 9(8):805-7, Jul. 2012.
Gallois and Marinho, "Leaf disk transformation using Agrobacterium tumefaciens-expression of heterologous genes in tobacco," Methods Mol. Biol., 49:39-48, 1995.
Gasiunus et al., "Cas9-crRNA ribonucleoprotein complex mediates specific DNA cleavage for adaptive immunity in bacteria," Proc Natl Acad Sci U.S.A., 109(39): E2579-86, Sep. 2012.
Geißler et al., "Transcriptional activators of human genes with programmable DNA-specificity," PLoS One, 6(5):e19509, May 2011.
GenBank Accession No. AAT46122, "avirulence protein AvrXa7-1M [Xanthomonas oryzae pv. oryzae]," Nov. 12, 2004, 2 pages.
GenBank Accession No. ABP27518.1, "Sequence 2533 from U.S. Pat. No. 7,193,069," Apr. 11, 2007, 1 page.
GenBank Accession No. ACD58243, "TAL effector AvrBs3/PthA [Xanthomonas oryzae pv. oryzae PXO99A]," May 19, 2008, 2 pages.

GenBank Accession No. AM778833.1, "Tomato leaf curl New Delhi virus segment DNA-B, complete sequence," Jan. 7, 2010, 2 pages.
GenBank Accession No. AY986492, "*Oryza sativa* (indica cultivar-group) Xa27 (Xa27) gene, Xa27-IRBB27 allele, complete cds," 2 pages, Jun. 24, 2005.
GenBank Accession No. CP000967, GI: 188518722, "Xanthomonas oryzae pv. oryzae PXO99A, complete genome," May 19, 2008, 606 pages.
GenBank Accession No. J04623, "F.okeanokoites methylase (MFokI) and endonuclease (RFokI) genes, complete cds," Apr. 1993, 2 pages.
GenBank Accession No. M28828, "F.okeanokoites fokIR and fokIM genes encoding endonuclease and methyltransferase, complete cds," Apr. 1993, 3 pages.
GenBank Accession No. P14727, "RecName: Full=Avirulence protein AvrBs3," Jun. 28, 2011, 3 pages.
GenBank Accession No. X16130, "Xanthomonas vesicatoria plasmid pXV11 avrBs3 gene for avirulence protein avrBs3," Oct. 15, 2007, 3 pages.
Gera and McIver., "Laboratory Growth and Maintenance of *Streptococcus pyogenes* (The Group A *Streptococcus*, GAS)," Curr Protoc Microbiol., 30:Unit 9D.2.1-9D.2.13, Oct. 2013.
Gil-Humanes et al., "Genetic transformation of wheat" Advances in the transformation method and applications for obtaining lines with imporved bread-making quality and low toxicity in relation to celiac disease, Ed.Alvarez IntechOpen, 2011:135-50.
Givord et al., "Detection of geminiviruses from tropical countries by a double monoclonal antibody ELISA using antibodies to African cassava mosaic virus," Agronomie-Sciences des Productions Vegetales et de l'Environnement, 14(5):327-334, Jan. 1994.
Gleba et al., "Viral vectors for the expression of proteins in plants," Curr Opin Biotechnol., 18(2):134-141, Apr. 2007.
Göhre and Robatzek, "Breaking the barriers: microbial effector molecules subvert plant immunity," Ann. Rev. Phytopathol., 46:189-215, 2008.
Golds et al., "Stable plastid transformation in PEG-treated protoplasts of nicotiana tabacum," Nature Biotechnology, 11:95-97, Jan. 1993.
Gonchar et al., PspXI, a novel restriction endonuclease that recognizes the unusual DNA sequence 5'-VC↓TCGAGB-3', Bulletin of biotechnology and physico-chemical biology, 1(1):18-24, 2005, Translation by Ovchinnikov, "Science sibenzyme.com" [online], [retrieved on Aug. 11, 2011]. Retrieved from the Internet: URL: <http://science.sibenzyme.com/article8_article_3_1.phtml>, 4 pages.
González et al., "Regeneration of transgenic cassava plants (*Manihot esculenta* Crantz) through Agrobacterium-mediated transformation of embryogenic suspension cultures," Plant Cell Reports, 17(11):827-831, Aug. 1998.
Gonzalez et al., "Molecular and pathotypic characterization of new Xanthomonas oryzae strains from West Africa," Mol. Plant Microbe. Interact., 20(5):534-46, 2007.
Gorbunova and Levy, "Non-homologous DNA end joining in plant cells is associated with deletions and filler DNA insertions," Nucleic Acids Res., 25(22):4650-7, Nov. 1997.
Govindarajulu et al., "Evaluation of constitutive viral promoters in transgenic soybean roots and nodules," Mol. Plant Microbe Interact, 21(8):1027-1035, Aug. 2008.
Gratz et al., "Genome engineering of *Drosophila* with the CRISPR RNA-guided Cas9 nuclease," Genetics, 194(4):1029-35, Aug. 2013.
Greiner et al., "Ectopic expression of a tobacco invertase inhibitor homolog prevents cold-induced sweetening of potato tubers," Nature Biotechnology, 17(7):708-711, Jul. 1999.
Greisman and Pabo, "A general strategy for selecting high-affinity zinc finger proteins for diverse DNA target sites," Science, 275(5300):657-61, 1997.
Gu et al., "Transcription activator-like type III effector AvrXa27 depends on OsTFIIAgamma5 for the activation of Xa27 transcription in rice that triggers disease resistance to Xanthomonas oryzae pv. oryzae," Mol. Plant Pathol., 10(6):829-35, 2009.
Gu et al.,"R gene expression induced by a type-III effector triggers disease resistance in rice," Nature, 435:1122-5, 2005.

(56) References Cited

OTHER PUBLICATIONS

Guan et al., "Heritable endogenous gene regulation in plants with designed polydactyl zinc finger transcription factors," Proc. Natl. Acad. Sci. USA., 99(20):13296-301, 2002.
Gürlebeck et al., "Dimerization of the bacterial effector protein AvrBs3 in the plant cell cytoplasm prior to nuclear import," Plant J., 42:175-87, 2005.
Gürlebeck et al., "Type III effector proteins from the plant pathogen Xanthomonas and their role in the interaction with the host plant," J. Plant Physiol., 163(3):233-55, 2006.
Gürlebeck et al., "Visualization of novel virulence activities of the Xanthomonas type III effectors AvrBs1, AvrBs3, and AvrBs4," Mol. Plant Pathol., 10(2):175-88, 2009.
Gutierrez, "Geminivirus DNA replication," Cell. Mol. Life Sci., 56(3-4):313-29, Oct. 1999.
Gutierrez, "Strategies for geminivirus DNA replication and cell cycle interference," Physiol. Mol. Plant Pathol., 60(5):219-30, May 2002.
Haber, "In vivo biochemistry: Physical monitoring of recombination induced by site-specific endonucleases," Bioessays, 17:609-20, 1995.
Haberlach et al., "Isolation, culture and regeneration of protoplasts from potato and several related Solanum species," Plant Science, 39:67-74, May 1985.
Hahn et al., "New mechanistic insights into the virulence activity of the Xanthomonas type III effector AvrBs3," (abstract), XIV International Congress on Molecular Plant-Microbe Interactions, Quebec City, Canada, Jul. 19-23, 2009, 2 pages.
Halford et al., "The reaction mechanism of FokI excludes the possibility of targeting zinc finger nucleases to unique DNA sites," Biochem. Soc. Trans., 39:584-8, 2011.
Handel et al., "Expanding or restricting the target site repertoire of zinc-finger nucleases: the inter-domain linker as a major determinant of target site selectivity," Mol. Ther., 17:104-11, 2009.
Haun et al., "Improved soybean oil quality by targeted mutagenesis of fatty acid desaturase 2 gene family," Plant Biotechnology Journal, 12(7):934-40, Sep. 2014.
Haupt et al., "Evidence for symplastic phloem unloading in sink leaves of barley," Plant Physiol., 125:209-18, Jan. 2001.
Hellemans et al., "qBase relative quantification framework and software for management and automated analysis of real-time quantitative PCR data," Genome Biol., 8(2):R19, 2007.
Herbers et al., "Race-specificity of plant resistance to bacterial spot disease determined by repetitive motifs in a bacterial avirulence protein," Nature, 356:172-4, 1992.
Heuer et al., "Repeat domain diversity of avrBs3-like genes in Ralstonia solanacearum strains and association with host preferences in the field," Appl. Environ. Microbiol., 73(13):4379-84, 2007.
Hicks and Raikhel, "Specific binding of nuclear localization sequences to plant nuclei," Plant Cell, 5(8): 983-94, Aug. 1993.
Hockemeyer et al., "Genetic engineering of human pluripotent cells using TALE nucleases," Nat Biotechnol., 29(8):731-4, 2011.
Hopkins et al., "Identification of a family of avirulence genes from Xanthomonas oryzae pv. oryzae," Mol. Plant Microbe. Interact., 5(6):451-9, 1992.
Horsch et al., "A simple and general method for transferring genes into plants," Science, 227(4691):1229-31, Mar. 1985.
Hu et al., "A virulence gene and insertion element-based RFLP as well as RAPD markers reveal high levels of genomic polymorphism in the rice pathogen Xanthomonas oryzae pv. oryzae," Syst. Appl. Microbiol., 30:587-600, 2007.
Huang et al., "A DNA replicon system for rapid high-level production of virus-like particles in plants," Biotechnol Bioeng., 103(4):706-714, Jul. 1, 2009.
Huang et al., "Heritable gene targeting in zebrafish using customized TALENs," Nat Biotechnol, 29(8):699-700, 2011.
Hummel et al., "Rice gene activation by transcription activator-like effectors of Xanthomonas oryzae pvs. oryzae and oryzicola," poster presentation, and "A cipher-like mechanism governs TAL effector-DNA recognition," poster #13-517, XIV International Congress on Molecular Plant-Microbe Interactions, Jul. 19-23, 2009, Quebec City, Canada, 3 pages.
Hurt et al., "Highly specific zinc finger proteins obtained by directed domain shuffling and cell-based selection," Proc. Natl. Acad. Sci. USA., 100(21):12271-6, 2003.
Hwang et al., "Efficient genome editing in zebrafish using a CRISPR-Cas system," Nat. Biotechnol., 31(3):227-9, Mar. 2013.
Isalan et al., "A rapid, generally applicable method to engineer zinc fingers illustrated by targeting the HIV-1 promoter," Nat. Biotechnol., 19(7):656-60, 2001.
Ishida et al., "Agrobacterium-mediated transformation of maize," Nat. Protoc., 2(7):1614-21, 2007.
Jackel et al., "Protein design by directed devolution," Ann. Rev. Biophys., 37:155-73, 2008.
Jacoby et al., "Expanding LAGLIDADG endonuclease scaffold diversity by rapidly surveying evolutionary sequence space," Nucleic Acids Res., 40(11):4954-64, Feb. 2012.
Jiang et al., "Demonstration of CRISPR/Cas9/sgRNA-mediated targeted gene modification in Arabidopsis, tobacco, sorghum and rice," Nucleic acids research, 41(20):e188, Aug. 2013.
Jiang et al., "RNA-guided editing of bacterial genomes using CRISPR-Cas systems," Nat. Biotechnol., 31(3):233-239, Mar. 2013.
Jinek et al., "A programmable dual-RNA-guided DNA endonuclease in adaptive bacterial immunity," Science, 337(6096):816-21, Aug. 2012.
Jinek et al., "RNA-programmed genome editing in human cells", Elife, 2:e00471, Jan. 2013.
Jones and Dangl, "The plant immune system," Nature, 444:323-9, 2006.
Jordan et al., "Physical delimitation of the pepper Bs3 resistance gene specifying recognition of the AvrBs3 protein from Xanthomonas campestris pv. vesicatoria," Theor. Appl. Genet., 113(5):895-905, 2006.
Kay and Bonas, "How Xanthomonas type III effectors manipulate the host plant," Curr. Opin. Microbiol., 12:37-43, 2009.
Kay et al., "A Bacterial Effector Acts as a Plant Transcription Factor and Induces a Cell Size Regulator," Science, 318(5850):648-51, 2007.
Kay et al., "Characterization of AvrBs3-like effectors from a Brassicaceae pathogen reveals virulence and avirulence activities and a protein with a novel repeat architecture," Mol. Plant Microbe Interact., 18(8):838-48, 2005.
Kay et al., "Detailed analysis of the DNA recognition motifs of the Xanthomonas type III effectors AvrBs3 and AvrBs3deltarep16," Plant J., 59(6):859-71, 2009.
Keshavarzi et al., "Basal defenses induced in pepper by lipopolysaccharides are suppressed by Xanthomonas campestris pv. vesicatoria," Mol. Plant Microbe Interact., 17(7):805-15, 2004.
Kheyr-Pour et al., "Agroinoculation of tomato yellow leaf curl virus (TYLCV) overcomes the virus resistance of wild Lycopersicon species," Plant Breeding, 112(3):228-233, Apr. 1994.
Kim and Chandrasegaran, "Chimeric restriction endonuclease," Proc. Natl. Acad. Sci. USA, 91(3):883-7, Feb. 1994.
Kim et al, "Hybrid restriction enzymes: zinc finger fusions to Fok I cleavage domain," Proc. Natl. Acad Sci. USA 93(3):1156-60, Feb. 1996.
Kim et al., "Highly efficient RNA-guided genome editing in human cells via delivery of purified Cas9 ribonucleoproteins," Genome Res., 24(6):1012-1019, Jun. 2014.
Kim et al., "Comparative analysis of three indigenous plasmids from Xanthomonas axonopodis pv. glycines," Plasmid., 56(2):79-87, 2006.
Kim et al., "Construction of a Z-DNA-specific restriction endonuclease," Proc. Natl. Acad. Sci. USA, 94(24):12875-9, 1997.
Kim et al., "Site-specific cleavage of DNA-RNA hybrids by zinc finger/FokI cleavage domain fusions," Gene., 203(1):43-9, 1997.
Kim et al., "Targeted genome editing in human cells with zinc finger nucleases constructed via modular assembly," Genome Res., 19:1279-1288, Jul. 2009.
Klahre et al., "High molecular weight RNAs and small interfering RNAs induce systemic posttranscriptional gene silencing in plants," Proc. Natl. Acad. Sci. USA., 99(18):11981-11986, Sep. 2002.

(56) References Cited

OTHER PUBLICATIONS

Klein et al., "Transformation of microbes, plants and animals by particle bombardment," Biotechnology, 10(3):286-91, Mar. 1992.
Knoop et al., "Expression of avirulence gene avrBs3 from Xanthomonas campestris pv. vesicatoria is not under the control of hrp genes and is independent of plant factors," J. Bacteriol., 173(22):7142-50, 1991.
Lahaye and Bonas, "Molecular secrets of bacterial type III effector proteins," Trends Plant. Sci., 6(10):479-85, 2001.
Lakshmanan et al., "Rapid and efficient gene delivery into plant cells using designed peptide carriers," Biomacromolecules, 14(1):10-6, Jan. 2013.
Lange et al., "Classical nuclear localization signals: definition, function, and interaction with importin α," J. Biol. Chem., 282(8):5101-5, Feb. 2007.
Laursen et al., "Production of fertile transgenic maize by electroporation of suspension culture cells," Plant Mol. Biol., 24(1):51-61, Jan. 1994.
Lawrence and Jackson, "Requirements for cell-to-cell movement of Barley stripe mosaic virus in monocot and dicot hosts," Mol. Plant Pathol., 2:65-75, Mar. 2001.
Lazarowitz et al., "Maize streak virus genes essential for systemic spread and symptom development," EMBO J., 8(4):1023-32, Apr. 1989.
Ledford, "Plant genes get fine tailoring," Nature News [online], Apr. 29, 2009 [retrieved on May 21, 2009]. Retrieved from the Internet: <URL: http://www.nature.com/news/2009/090429/full/news.2009.415.html>, 3 pages.
Lee et al., "Barley stripe mosaic virus-mediated tools for investigating gene function in cereal plants and their pathogens: virus-induced gene silencing, host-mediated gene silencing, and virus-mediated overexpression of heterologous protein," Plant Physiol., 160:582-90, Oct. 2012.
Lee et al., "Environmental Effects on Oleic Acid in Soybean Seed Oil of Plant Introductions with Elevated Oleic Concentration," CropScience, 49:1762-1768, Sep. 2009.
Li et al., "Gene replacements and insertions in rice by intron targeting using CRISPR-Cas9," Nature Plants, 2(10):16139, Oct. 2016.
Li et al., "High-efficiency TALEN-based gene editing produces disease-resistant rice," Nat. Biotechnol., 30:390-2, May 2012.
Li et al., "How RNA unfolds and refolds," Annu Rev Biochem., 77:77-100, 2008.
Li et al., "Multiplex and homologous recombination-mediated genome editing in *Arabidopsis* and Nicotiana benthamiana using guide RNA and Cas9," Nat. Biotechnol., 31(8):688-91, Aug. 2013.
Li et al., "Functional domains in FokI restriction endonuclease," Proc. Natl. Acad. Sci. USA, 89(10):4275-9, 1992.
Li et al., "Modularly assembled designed TAL effector nucleases for targeted gene knockout and gene replacement in eukaryotes," Nucl. Acids Res., 39:6315-25, 2011.
Li et al., "TAL nucleases (TALNs): hybrid proteins composed of TAL effectors and FokI DNA-cleavage domain," Nucl. Acids Res., 39(1):359-72, 2010.
Liang et al., "Targeted mutagenesis in *Zea mays* using TALENs and the CRISPR/Cas system," J. Genet. Genomics, 41:63-8. Feb. 2014.
Liang et al., "Cloning and characterization of a novel avirulence gene (arp3) from Xanthomonas oryzae pv. oryzae," DNA Seq., 15(2):110-7, Apr. 2004.
Lim et al., "Protoplast isolation and regeneration of fertile plants from *Arabidopsis* Trp mutant, trp1-100," Korean Journal of Biological Sciences, 2(2):239-242, Jan. 1998.
Liu et al., "Bean yellow dwarf virus RepA, but not rep, binds to maize retinoblastoma protein, and the virus tolerates mutations in the consensus binding motif," Virol., 256(2):270-9, Apr. 1999.
Liu et al., "Design of polydactyl zinc-finger proteins for unique addressing within complex genomes," Proc. Natl. Acad. Sci. USA, 94(11):5525-30, 1997.

Livak and Schmittgen, "Analysis of relative gene expression data using real-time quantitative PCR and the 2(-Delta Delta C(T)) Method," Method. Methods, 25:402-408, Dec. 2001.
Lloyd et al., "Targeted mutagenesis using zinc-finger nucleases in *Arabidopsis*," Proc. Natl. Acad. Sci. USA., 102(6):2232-7, Feb. 2005.
Lopez-Ochoa et al., "Peptide aptamers that bind to a geminivirus replication protein interfere with viral replication in plant cells," J Virol., 80(12):5841-5853, Jun. 2006.
Luo et al., "Non-transgenic plant genome editing using purified sequence-specific nucleases," Molecular plant, 8(9):1425-7, Sep. 2015.
Mae and Langel, "Cell-penetrating peptides as vectors for peptide, protein and oligonucleotide delivery," Curr Opin Pharmacol, 6(5):509-14, Oct. 2006.
Mahfouz et al., "De novo-engineered transcription activator-like effector (TALE) hybrid nuclease with novel DNA binding specificity creates double-strand breaks," Proc. Natl. Acad. Sci. USA, 108:2623-8, 2011.
Mahfouz et al., "TALE nucleases and next generation GM crops," GM Crops, 2(2):99-103, Apr. 2011.
Mak, "Sequence-specific DNA-binding TALEs," Nat. Biotechnol., 29:43, 2011.
Makarova et al., "Evolution and classification of the CRISPR-Cas systems," Nat. Rev. Microbiol.., 9(6):467-77, May 9, 2011.
Makarova et al., "A putative RNA-interference-based immune system in prokaryotes: computational analysis of the predicted enzymatic machinery, functional analogies with eukaryotic RNAi, and hypothetical mechanisms of action," Biology Direct, 1(1):7, Dec. 2006.
Mali et al., CAS9 transcriptional activators for target specificity screening and paired nickases for cooperative genome engineering, Nat Biotechnol., 31(9):833-838, Sep. 2013.
Mali et al., "RNA-guided human genome engineering via Cas9," Science 339(6121):823-6, Feb. 2013.
Malik et al., "Interaction between coat protein and replication initiation protein of Mung bean yellow mosaic India virus might lead to control of viral DNA replication," Virol., 337(2):273-83, Jul. 2005.
Mansoor et al., "Geminivirus disease complexes: an emerging threat," Trends Plant Sci., 8(3):128-134, Mar. 2003.
Mao et al., "Application of the CRISPR-Cas system for efficient genome engineering in plants," Molecular plant, 6(6):2008-11, Nov. 2013.
Marois et al., "The xanthomonas type III effector protein AvrBs3 modulates plant gene expression and induces cell hypertrophy in the susceptible host," Mol. Plant. Microbe Interact., 15(7):637-46, 2002.
Marton et al., "Nontransgenic genome modification in plant cells," Plant Physiol., 154(3):1079-87, Sep. 2010.
Matzeit et al., "Wheat dwarf virus vectors replicate and express foreign genes in cells of monocotyledonous plant," Plant Cell, 3(3):247-58, Mar. 1991.
McCormac et al., "Efficient co-transformation of Nicotiana tabacum by two independent T-DNAs, the effect of T-DNA size and implications for genetic separation," Transgenic Res., 10(2):143-55, Apr. 2001.
McCormac et al., "Regulation of HEMA1 expression by phytochrome and a plastid signal during de-etiolation in *Arabidopsis thaliana*," Plant J., 25(5):549-61, Mar. 2001.
McCormick et al., "Leaf disc transformation of cultivated tomato (*L. esculentum*) using Agrobacterium tumefaciens," Plant Cell Rep., 5(2):81-84, Apr. 1986.
Ménoret et al., "Homology-directed repair in rodent zygotes using Cas9 and TALEN engineered proteins," Scientific reports, 5:14410, Oct. 2015.
Miao et al., "Targeted mutagenesis in rice using CRISPR-Cas system," Cell research, 23(10):1233-1236, Oct. 2013.
Miller et al., "A TALE nuclease architecture for efficient genome editing," Nat. Biotechnol., 29:143-8, 2011.
Miller et al., "An improved zinc-finger nuclease architecture for highly specific genome editing," Nat. Biotechnol., 25:778-85, 2007.

(56) References Cited

OTHER PUBLICATIONS

Minczuk et al., "Development of a single-chain, quasi-dimeric zinc-finger nuclease for the selective degradation of mutated human mitochondrial DNA," Nucleic Acids Res., 36(12):3926-38, 2008.
Mino et al., "Efficient double-stranded DNA cleavage by artificial zinc-finger nucleases composed of one zinc-finger protein and a single-chain FokI dimer," J. Biotechnol., 140(3-4):156-61, 2009.
Moffat, "Geminiviruses emerge as a serious crop threat," Science, 286(5446): 1835, Dec. 1999.
Moore et al., "Transactivated and chemically inducible gene expression in plants," Plant J., 45:651-83, 2006.
Morbitzer et al., "Assembly of custom TALE-type DNA binding domains by modular cloning," Nucleic Acids Res., 39(13):5790-99, 2011.
Morbitzer et al., "Regulation of selected genome loci using de novo-engineered transcription activator-like effector (TALE)-type transcription factors," Proc. Natl. Acad. Sci. USA., 107(50):21617-22, 2010.
Moscow and Bogdanove, "A Simple Cipher Governs DNA Recognition by TAL Effectors," Science, 326(5959): 1501, 2009.
Muangsan and Robertson, "Geminivirus vectors for transient gene silencing in plants," Methods Mol Biol., 265:101-15, 2004.
Muller et al., "Processing of gene expression data generated by quantitative real-time RT-PCR," BioTechniques, 32(6):1372-9, Jun. 2002.
Murakami et al., "The repeat domain of the type III effector protein PthA shows a TPR-like structure and undergoes conformational changes upon DNA interaction," Proteins, 78:3386-95, 2010.
Murray et al., "Rapid isolation of high molecular weight plant DNA," Nucl. Acids Res, 8(19):4321-4325, Oct. 1980.
Mussolino et al. "A novel TALE nuclease scaffold enables high genome editing activity in combination with low toxicity," Nucl. Acids Res., 39(21): 9283-93, 2011.
Nagata et al., "Delivery of tobacco mosaic virus RNA into plant protoplasts mediated by reverse-phase evaporation vesicles (liposomes)," Mol. Gen. Genet., 184(2):161-165, Dec. 1981.
Nakagawa et al., "Development of series of gateway binary vectors, pGWBs, for realizing efficient construction of fusion genes for plant transformation," J. Biosci. Bioeng., 104:34-41, 2007.
Naqvi et al., "In silico analysis reveals that several tomato microRNA/microRNA* sequences exhibit propensity to bind to tomato leaf curl virus (ToLCV) associated genomes and most of their encoded open reading frames (ORFs)," Plant Physiol Biochem., 49(1):13-17, Epub Oct. 1, 2010.
Narsai et al., "Genome-wide analysis of mRNA decay rates and their determinants in *Arabidopsis thaliana*," Plant Cell, 19(11):3418-36, Nov. 2007.
Nekrasov et al., "Targeted mutagenesis in the model plant Nicotiana benthamiana using Cas9 RNA-guided endonuclease," Nat. Biotechnol., 31(8):691-3, Aug. 2013.
Niño-Liu et al., "Xanthomonas oryzae pathovars: model pathogens of a model crop," Mol. Plant Pathol., 7(5):303-24, 2006.
Nissan et al. "The type III effectors HsvG and HsvB of gall-forming Pantoea agglomerans determine host specificity and function as transcriptional activators," Mol. Microbio., 61(5): 1118-31, 2006.
Noël et al., "XopC and XopJ, two novel type III effector proteins from Xanthomonas campestris pv. vesicatoria," J. Bacteriol., 185(24):7092-102, 2003.
Notice of Opposition in European Application No. 14732023.8, dated Aug. 20, 2019, 10 pages.
Notice of Opposition in European Application No. 14732023.8, dated Aug. 26, 2019, 23 pages.
Notice of Opposition in European Application No. 14732023.8, dated Aug. 27, 2019, 50 pages.
Notice of Opposition in European Application No. 14732023.8, dated Aug. 28, 2019, 39 pages.
Ohlsson and Eriksson., "Transformation of *Brassica campestris* protoplasts with Agrobacterium tumefaciens," Hereditas., 108:173-177, May 1988.

Ovchinnikov et al., "PspXI, a novel restriction endonuclease that recognizes the unusual DNA sequence 5-VCTCGAGB-3," Bull Biotech Physio-Chemical Biol, 2005, 1(1):18-24, retrieved from the Internet: http://science.sibenzyme.com/articls8_article_3_1.phtml.
Pacher et al., "Two unlinked double-strand breaks can induce reciprocal exchanges in plant genomes via homologous recombination and nonhomologous end joining," Genetics, 175(1):21-9, Jan. 2007.
Padidam et al., "A phage single-stranded DNA (ssDNA) binding protein complements ssDNA accumulation of a geminivirus and interferes with viral movement," J. Virol., 73(2):1609-16, Feb. 1999.
Padidam, "Chemically regulated gene expression in plants," Cur. Opin. Plant Biol., 6:169-77, 2003.
Pandey et al., "A geminiviral amplicon (VA) derived from Tomato leaf curl virus (ToLCV) can replicate in a wide variety of plant species and also acts as a VIGS vector," Virol. J., 6:152, Sep. 2009.
Paplomatas et al., "Molecular characterization of a new sap-transmissible bipartite genome geminivirus infecting tomatoes in Mexico," Phytopathology, 84(10):1215-1223, Oct. 1, 1994.
Paques and Duchateau, "Meganucleases and DNA Double-Strand Break-Induced recombination: Perspectives for Gene Therapy," Curr. Gene Ther., 7:49-66, 2007.
Park et al., "Avirulence gene diversity of Xanthomonas axonopodis pv. Glycines isolated in Korea," J. Microbiol. Biotechnol., 18(9):1500-9, 2008.
Paszkowski et al., "Replication of the DNA a component of African cassava mosaic virus in a heterologous system," J. Gen. Virol., 74(12):2725-9, Dec. 1993.
Pattanayak et al., "Revealing off-target cleavage specificities of zinc-finger nucleases by in vitro selection," Nat. Methods, 8:765-70, 2011.
Paulus et al., "Silencing β1,2-xylosyltransferase in transgenic tomato fruits reveals xylose as constitutive component in IgE-binding epitopes," Fronties in Plant Science, 2:42, Aug. 2011.
Pavletich and Pabo, "Zinc finger-DNA recognition: crystal structure of a Zif268-DNA complex at 2.1 A," Science, 252:809-17, 1991.
Pearson, "The fate of fingers," Nature, 455:160-4, 2008.
Pennisi, "The Tale of the TALES," Science, 338(6113):1408-11, 2012.
Peretz et al., "A universal expression/silencing vector in plants," Plant Physiol. 145(4):1251-63, Dec. 2007.
Pham et al., "Mutant alleles of FAD2-1A and FAD2-1B combine to produce soybeans with the high oleic acid seed oil trait," BMC Plant Biol., 10:195, Dec. 2010.
Phillips, "Regulation of transcription and gene expression in eukaryotes," Nature Education, 1(1):199, 4 pages, 2008.
Pingoud and Silva, "Precision genome surgery," Nat. Biotechnol., 25(7):743-4, 2007.
Podevin et al., "Site-directed nucleases: a paradigm shift in predictable, knowledge-based plant breeding," Trends in biotechnology, 31(6):375-83, Jun. 2013.
Podhajska and Szybalski, "Conversion of the FokI endonuclease to a universal restriction enzyme: cleavage of phage M13mp7 DNA at predetermined sites," Gene, 40(2-3):175-82, 1985.
Pohl et al., "Temperature Dependence of the Activity of DNA-Modifying Enzymes: Endonucleases and DNA Ligase," Eur J Biochem., 123:141-152, 1982.
Polston et al., "Transmitting plant viruses using whiteflies," J Vis Exp., (81):e4332, Nov. 8, 2013.
Pomerantz et al., "Structure-based design of transcription factors," Science, 267(5194):93-6, 1995.
Porteus and Baltimore, "Chimeric nucleases stimulate gene targeting in human cells," Science, 300:763, 2003.
Porteus and Carroll, "Gene targeting using zinc finger nucleases," Nature Biotechnol, 23:967-73, 2005.
Porteus, "Zinc fingers on target," Nature, 459: 337-8, 2009.
Potenza et al., "Targeting transgene expression in research, agricultural, and environmental applications: Promoters used in plant transformation," In vitro Cell Dev. Biol., 40(1):1-22, 2004.

(56) References Cited

OTHER PUBLICATIONS

Press Release on PR Newswire. Oct. 19, 2010. https://www.prnewswire.com/news-releases/cellectis-plant-sciences-licenses-plant-transformation-technology-from-midwest-oilseeds-105234993.html.
Puchta et al., "Homologous recombination in plant cells is enhanced by in vivo induction of double strand breaks into DNA by a site-specific endonuclease," Nucl. Acids Res., 21(22):5034-40, Nov. 1993.
Puchta et al., "Two different but related mechanisms are used in plants for the repair of genomic double-strand breaks by homologous recombination," Proc. Natl. Acad. Sci. USA, 93(10):5055-60, May 14, 1996.
Qi et al., "Repurposing CRISPR as an RNA-guided platform for sequence-specific control of gene expression," Cell, 152(5):1173-1183, Feb. 28, 2013.
Radecke et al., "Zinc-finger nuclease-induced gene repair with oligodeoxynucleotides: wanted and unwanted target locus modifications," Mol. Ther., 18(4):743-53, 2010.
Reyes et al., "Peptide aptamers that bind to geminivirus replication proteins confer a resistance phenotype to tomato yellow leaf curl virus and tomato mottle virus infection in tomato," J Virol., 87(17):9691-9706, Sep. 1, 2013.
Reyon et al., "FLASH assembly of TALENs for high-throughput genome editing," Nat Biotechnol, 30(5):460-465, May 2012.
Roberts, "Fast-track applications: The potential for direct delivery of proteins and nucleic acids to plant cells for the discovery of gene function," Plant Meth, 1(1):12, Dec. 2005.
Rodriguez-Negrete et al., "RNA silencing against geminivirus: complementary action of posttranscriptional gene silencing and transcriptional gene silencing in host recovery," J. Virol., 83(3):1332-40, Feb. 2009.
Römer et al., "Plant pathogen recognition mediated by promoter activation of the pepper Bs3 resistance gene," Science, 318(5850):645-8, 2007.
Römer et al., "A single plant resistance gene promoter engineered to recognize multiple TAL effectors from disparate pathogens," Proc. Natl. Acad. Sci. USA, 106(48):20526-31, 2009.
Römer et al., "Promoter elements of rice susceptibility genes are bound and activated by specific TAL effectors from the bacterial blight pathogen, Xanthomonas oryzae pv. oryzae," New Phytol., 187:1048-57, 2010.
Römer et al., "Recognition of AvrBs3-Like Proteins Is Mediated by Specific Binding to Promoters of Matching Pepper Bs3 Alleles," Plant Physiol., 150:1697-712, 2009.
Romero et al., "Temperature Sensitivity of the Hypersensitive Response of Bell Pepper to Xanthomonas axonopodis pv. vesicatoria," Phytopathology, 92(2):197-203, 2002.
Rossier et al., "HrpB2 and HrpF from Xanthomonas are type III-secreted proteins and essential for pathogenicity and recognition by the host plant," Mol. Microbiol., 38(4):828-38, 2000.
Rossier et al., "The Xanthomonas Hrp type III system secretes proteins from plant and mammalian bacterial pathogens," Proc. Natl. Acad. Sci. USA, 96(16):9368-73, 1999.
Rouet et al., "Expression of a site-specific endonuclease stimulates homologous recombination in mammalian cells," Proc. Natl. Acad. Sci. USA, 91(13):6064-8, 1994.
Rouet et al., "Introduction of double-strand breaks into the genome of mouse cells by expression of a rare-cutting endonuclease," Mol. Cell Biol., 14(12):8096-106, 1994.
Ruijter et al., "Amplification efficiency: linking baseline and bias in the analysis of quantitative PCR data," Nucleic Acids Res., 37(6):e45, Apr. 2009.
Rybak et al., "Identification of *Xanthomonas citri* ssp. *citri* host specificity genes in a heterologous expression host," Mol. Plant Pathol., 10(2):249-62, 2009.

Rybicki and Martin, "Virus-derived ssDNA vectors for the expression of foreign proteins in plants," Curr Top Microbiol Immunol., 375:19-45, 2014.

Salomon and Puchta, "Capture of genomic and T-DNA sequences during double-strand break repair in somatic plant cells," EMBO J., 17:6086-95, Oct. 1998.

Sander et al., "Selection-free zinc-finger-nuclease engineering by context-dependent assembly (CoDA)," Nat. Methods 8(1):67-9, Jan. 2011.

Sandhu et al., "Enhanced oleic acid content in the soybean mutant M23 is associated with the deletion in the Fad2-1a gene encoding a fatty acid desaturase," JAOCS, 84(3):229-235, Mar. 2007.

Santiago et al., "Targeted gene knockout in mammalian cells by using engineered zinc-finger nucleases," Proc. Natl. Acad. Sci .USA, 105(15):5809-14, 2008.

Sapp, "The Prokarvote-Eukaryote Dichotomy: Meanings and Mythology," Microbiol Mol Biol Rev, 69(2):292-305, 2005.

Schiml et al., "The CRISPR/Cas svstem can be used as nuclease for in plants gene targeting and as paired nickases for directed mutagenesis in *Arabidopsis* resulting in heritable progeny," Plant J., 80:1139-50, Oct. 2014.

Schneider et al., "NIH Image to ImageJ: 25 years of image analysis," Nat. Methods, 9(7):671-5, Jul. 2012.

Scholze and Boch, "TAL effectors are remote controls for gene activation," Curr. Opin. Microbiol., 14:47-53, 2011.

Scholze and Boch. "TAL effector-DNA specificity," Virulence, 1(5):428-32, 2010.

Schornack et al., "Characterization of AvrHah1, a novel AvrBs3-like effector from Xanthomonas gardneri with virulence and avirulence activity," New Phytol., 179:546-56, 2008.

Schornack et al., "Expression levels of avrBs3-like genes affect recognition specificity in tomato Bs4—but not in pepper BS3-mediated perception," Mol. Plant Microbe Interact., 18(11):1215-25, 2005.

Schornack et al., "Gene-for-gene mediated recognition of nuclear-targeted AvrBs3-like bacterial effector proteins," J. Plant Physiol., 163:256-72, 2006.

Schornack et al., "The tomato resistance protein Bs4 is a predicted non-nuclear TIR-NB-LRR protein that mediates defense responses to severely truncated derivatives of AvrBs4 and overexpressed AvrBs3," Plant J., 37(1):46-60, 2004.

Schwarze et al., "In vivo protein transduction: delivery of a biologically active protein into the mouse," Science, 285(5433):1569-72, Sep. 1999.

Seemanpillai et al., "Transcriptional silencing of geminiviral promoter-driven transgenes following homologous virus infection," Mol. Plant Microbe Interact., 161(5):429-38, May 2003.

Segal et al., "Endonuclease-induced, targeted homologous extrachromosomal recombination in Xenopus oocytes," Proc. Natl. Acad. Sci. USA, 92(3):806-10, 1995.

Senthil-Kumar and Mysore, "RNAi in plants: Recent developments and applications in agriculture," In: Gene Silencing: Theory, Techniques and Applications, 183-199, 2010, Nova Science Publishers, Inc., Ed. Catalano.

Sera, "Inhibition of virus DNA replication by artificial zinc finger proteins," J. Virol., 79(4):2614-9, 2005.

Shan et al., "Genome editing in rice and wheat using the CRISPR/Cas system" Nat. Protoc. 9(10):2395-410, Oct. 2014.

Shan et al., "Targeted genome modification of crop plants using a CRISPR-Cas system," Nat Biotechnol., 31(8):686-8, Aug. 2013.

Shen and Hohn, "Amplification and expression of the β-glucuronidase gene in maize plants by vectors based on maize streak virus," Plant J., 5(2):227-36, Oct. 1993.

Shen and Hohn, "Vectors based on maize streak virus can replicate to high copy numbers in maize plants," J. Gen. Virol., 76(Pt4):965-9, Apr. 1995.

Shen et al., "Generation of gene-modified mice via Cas9/RNA-mediated gene targeting," Cell Res. 23(5):720-723, May 2013.

Shepard and Totten, "Mesophyll cell protoplasts of potato: isolation, proliferation, and plant regeneration," Plant Physiol, 60(2):313-316, Aug. 1977.

Shepherd et al., "Transgenic strategies for developing crops resistant to geminiviruses," Plant Science 176(1): 1-11, 2009.

Shevelev et al., "The TREX2 3'à5' exonuclease physically interacts with DNA polymerase delta and increases its accuracy," ScientificWorldJournal, 2:275-81, Feb. 2002.

(56) References Cited

OTHER PUBLICATIONS

Shivprasad et al., "Heterologous sequences greatly affect foreign gene expression in tobacco mosaic virus-based vectors," Virol., 255:312-23, Mar. 1999.
Shukla et al., "Precise genome modification in the crop species *Zea mays* using zinc-finger nucleases," Nature, 459(7245):437-41, Apr. 2009.
Simon et al., "Targeting DNA with triplex-forming oligonucleotides to modify gene sequence," Biochimie., 90:1109-16, 2008.
Skipper, "Technology: The holy grail for plant biologists," Nat. Rev. Genetics, 10(6):350, 2009.
Sparkes et al., "Rapid, transient expression of fluorescent fusion proteins in tobacco plants and generation of stably transformed plants," Nat Prtoc., 1(4):2019-2025, 2006.
Stanley., "Geminiviruses: plant viral vectors," Current Opinion in Genetics and Development., 3(1):91-96, Feb. 1993.
Steinert et al., "Homology-based double-strand break-induced genome engineering in plants," Plant Cell Rep., 35(7):1429-38, Jul. 2016.
Strasser et al., "Generation of glycol-engineered Nicotiana bethamiana for the production of monoclonal antibodies with a homogeneous human-like N-glycan structure," Plant Biotechnology Journal, 6(4):392-402, May 2008.
Studholme et al., "Genome-wide sequencing data reveals virulence factors implicated in banana Xanthomonas wilt," FEMS Microbiol. Lett., 310(2):182-92, 2010.
Suarez-Lopez and Gutierrez, "DNA replication of wheat dwarf geminivirus vectors: effects of origin structure and size," Virol., 227(2):389-99, Jan. 1997.
Sugio et al., "Two type III effector genes of Xanthomonas oryzae pv. oryzae control the induction of the host genes OsTFIIAγ1 and OsTFX1 during bacterial blight of rice," Proc. Natl. Acad. Sci. USA, 104:10720-5, 2007.
Svitashev et al., "Genome editing in maize directed by CRISPR-Cas9 ribonucleoprotein complexes," Nature communications, 7:13274, Nov. 2016.
Swarup et al., "An Xanthomonas citri pathogenicity gene, pthA, pleiotropically encodes gratuitous avirulence on nonhosts," Mol. Plant Microbe Interact., 5(3):204-13, 1992.
Szurek et al. "Type III-dependent translocation of the Xanthomonas AvrBs3 protein into the plant cell," Mol. Microbiol., 46(1): 13-23, 2002.
Szurek et al., "Eukaryotic features of the Xanthomonas type III effector AvrBs3: protein domains involved in transcriptional activation and the interaction with nuclear import receptors from pepper," Plant J., 26(5):523-34, 2001.
Takenaka et al., "Inhibition of tomato yellow leaf curl virus replication by artificial zinc-finger proteins," Nucl. Acids Symposium Series, 51(1):429-30, 2007.
Tan et al., "Imidazolinone-tolerant crops: history, current status and future," Pest Manag. Sci., 61(3):246-257, Mar. 2005.
Tang et al., "Efficient delivery of small interfering RNA to plant cells by a nanosecond pulsed laser-induced stress wave for post-transcriptional gene silencing," Plant Sci., 171(3):375-381, Sep. 2006.
Tatineni et al., "Efficient and stable expression of GFP through Wheat streak mosaic virus-based vectors in cereal hosts using a range of cleavage sites: formation of dense fluorescent aggregates for sensitive virus tracking," Virol., 410:268-81, Feb. 2011.
Thieme et al., "New type III effectors from Xanthomonas campestris pv. vesicatoria trigger plant reactions dependent on a conserved N-myristoylation motif," Mol. Plant Microbe Interact., 20(10):1250-61, 2007.
Thierry et al., "Cleavage of yeast and bacteriophage T7 genomes at a single site using the rare cutter endonuclease I-Sce I," Nucl. Acids Res., 19(1):189-90, 1991.
Third Party Observations Pursuant to ART. 115 EPC—EP 2 379 583 (Appl.: Bonas, Boch, Schornack, Lahaye)—Title: Modular DNA-binding domains and methods of use, EPO-Munich, 6 pages, 2012.

Thykjaer et al., "Gene targeting approaches using positive-negative selection and large flanking regions," Plant Mol. Biol., 35(4):523-30, Nov. 1997.
Timmermans et al., "Trans replication and high copy numbers of wheat dwarf virus vectors in maize cells," Nucleic Acids Res., 20(15):4047-54, Aug. 1992.
Timmermans et al., "Geminiviruses and their uses as extrachromosomal replicons," Annu. Rev. Plant Physiol. Plant Mol. Biol., 45:79-112, 1994.
Tovkach et al., "A toolbox and procedural notes for characterizing novel zinc finger nucleases for genome editing in plant cells," Plant J., 57:747-57, 2009.
Townsend et al., "High-frequency modification of plant genes using engineered zinc-finger nucleases," Nature, 459(7245):442-5, May 2009.
Ugaki et al., Replication of a geminivirus derived shuttle vector in maize endosperm cells, Nucleic Acids Res., 19(2):371-7, Jan. 1991.
UniProtKB No. Q03J16, "CRISPR-associated endonuclease Cas9 2," Mar. 6, 2013, 3 pages.
UniProtKB No. Q99ZW2, "CRISPR-associated endonuclease Cas9/Csn1," Jul. 11, 2012, 6 pages.
Unnamalai et al., "Cationic oligopeptide-mediated delivery of dsRNA for post-transcriptional gene silencing in plant cells," FEBS Lett., 566(1-3):307-310, May 2004.
Upadhyay et al., "RNA-guided genome editing for target gene mutations in wheat," G3 (Bethesda)., 3(12):2233-2238, Dec. 9, 2013.
Urnov et al., "Genome editing with engineered zinc finger nucleases," Nat. Rev. Genet., 11(9):636-46, Sep. 2010.
Urnov et al., "Highly efficient endogenous human gene correction using designed zinc-finger nuclease," Nature, 435(7042):646-51, 2005.
Van den Ackerveken et al., "Recognition of the bacterial avirulence protein AvBs3 occurs inside the host plant cell," Cell, 87(7):1307-16, 1996.
Van Den Elzen et al., "A chimaeric hygromycin resistance gene as a selectable marker in plant cells," Plant Molecular Biology, 5(5):299-302 Sep. 1985.
Vanderschuren et al., "Engineering resistance to geminiviruses-review and perspectives," Plant Biotechnol J., 5(2):207-220, Mar. 1, 2007.
Vanitharani et al., "Geminiviruses and RNA silencing," Trends Plant Sci., 10(3):144-51, Mar. 2005.
Vergunst et al., "VirB/D4-Dependent Protein Translocation from Agrobacterium into Plant Cells," Science, 290:979-82, 2000.
Voytas et al., "Plant science. DNA binding made easy," Science, 326(5959):1491-2, 2009.
Voytas, "Plant genome engineering with sequence-specific nucleases," Annual Review of Plant Biology, 2013, 64:327-350, Mar. 2013.
Wah et al., "Structure of FokI has implications for DNA cleavage," Proc. Natl. Acad. Sci. USA, 95(18):10564-9, 1998.
Wah et al., "Structure of the multimodular endonuclease FokI bound to DNA," Nature, 388(3):97-100, 1997.
Wang et al., "Hairpin RNAs derived from RNA polymerase II and polymerase III promoter-directed transgenes are processed differently in plants," RNA., 14(5):903-913, Epub Mar. 26, 2008.
Wang et al., "One-step generation of mice carrying mutations in multiple genes by CRISPR/Cas-mediated genome engineering," Cell, 153(4):910-918, May 2013.
Wang et al., "Chemically regulated expression systems and their applications in transgenic plants," Transgenic Res., 12:529-40, 2003.
Wang et al., "Improved cytoplasmic delivery to plant protoplasts via ph-sensitive liposomes," Plant Physiology, 82(1):179-184, Sep. 1986.
Watson et al., "RNA silencing platforms in plants," FEBS Lett., 579(26):5982-7, Oct. 2005.
Weber et al., "The type III-dependent Hrp pilus is required for productive interaction of Xanthomonas campestris pv. vesicatoria with pepper host plants," J. Bacteriol., 187(7):2458-68, 2005.
Wei et al., "TALEN or Cas9-Rapid, efficient and specific choices for genome modifications," Journal of Genetics and Genomics, 40(6):281-289, Jun. 2013.

(56) References Cited

OTHER PUBLICATIONS

Weigel et al., "Transformation of Agrobacterium Using Electroporation," Cold Spring Harb Protoc., 2006(7):1-3, 2006.
Weigel et al., "Transformation of Agrobacterium Using the Freeze-Thaw Method," Cold Spring Harbor Protocols, 2006(7):1031-6, 2006.
Wendt et al., "Production of Phytophthora infestans-resistant potato (*Solanum tuberosum*) utilising Ensifer adhaerens OV14," Transgenic Res., 21(3):567-578, Jun. 2012.
Wendt et al., "TAL effector nucleases induce mutations at a preselected location in the genome of primary barley transformants," Plant Mol. Biol., 83(3)279-85, Oct. 2013.
White and Yang, "Host and pathogen factors controlling the rice/ Xanthomonas oryzae interaction," Plant Physiol., 150:1677-86, 2009.
White et al., "The type III effectors of Xanthomonas," Mol. Plant Pathol., 10:749-66, 2009.
Woo et al., "DNA-free genome editing in plants with preassembled CRISPR-Cas9 ribonucleoproteins," Nature biotechnology, 33(11):1162, Nov. 2015.
Wright et al., "Efficient biolistic transformation of maize (*Zea mays* L.) and wheat (*Triticum aestivum* L.) using the phosphomannose isomerase gene, pmi, as the selectable marker," Plant Cell Rep., 20(5):429-436, Jun. 2001.
Wright et al., "High-frequency homologous recombination in plants mediated by zinc-finger nucleases," Plant J., 44(4):693-705, Nov. 2005.
Wu et al., "Direct delivery of bacterial avirulence proteins into resistant *Arabidopsis protoplasts* leads to hypersensitive cell death," The Plant Journal, 33(1):131-7, Jan. 2003.
Wu et al., "Tn5 transposase-assisted transformation of indica rice," Plant J, 68(1):186-200, Oct. 2011.
Xiang et al., "Temperature effect on CRISPR-Cas9 mediated genome editing," J Gene Genom., 44:199-205, 2017.
Xiao et al., "Chromosomal deletions and inversions mediated by TALENs and CRISPR/Cas in zebrafish," Nucleic acids research, 41(14):e141, Jun. 2013.
Xie and Yang, "RNA-guided genome editing in plants using a CRISPR-Cas system," Molecular Plant, 6(6):1975-1983, Nov. 2013.
Yadav and Chattopadhyay, "Enhanced viral intergenic region-specific short interfering RNA accumulation and DNA methylation correlates with resistance against a geminivirus," Mol. Plant Microbe. Interac., 24(10):1189-97, Oct. 2011.
Yang and White, "Diverse members of the AvrBs3/PthA family of type III effectors are major virulence determinants in bacterial blight disease of rice," Mol. Plant Microbe Interact., 17(11):1192-1200, 2004.
Yang et al. "The virulence factor AvrXa7 of Xanthomonas oryzae of Oryzae is a type III secretion pathway-dependent nuclear-localized double stranded DNA binding protein," Proc. Natl. Acad. Sci. USA, 97(17): 9807-12, 2000.
Yang et al., "Avoidance of host recognition by alterations in the repetitive and C-terminal regions of AvrXa7, a type III effector of Xanthomonas oryzae pv. oryzae," Mol. Plant Microbe Interact., 18(2):142-9, 2005.
Yang et al., "Os8N3 is a host disease-susceptibility gene for bacterial blight of rice," Proc. Natl. Acad. Sci. USA, 103:10503-8, 2006.
Yin et al., "A geminivirus-based guide RNA delivery system for CRISPR/Cas9 mediated plant genome editing," Sci. Rep., 5:14926, Oct. 2015.
Yoo et al., "*Arabidopsis mesophyll* protoplasts: a versatile cell system for transient gene expression analysis," Nat Protoc., 2(7):1565-1572, Jul. 2007.
Yuan et al., "Characterization of Xanthomonas oryzae-responsive cis-acting element in the promoter of rice race-specific susceptibility gene Xa13," Mol. Plant, 4(2):300-9, 2011.
Zhang et al., "Resistance to cassava mosaic disease in transgenic cassava expressing antisense RNAs targeting virus replication genes," Plant Biotechnol J., 3(4):385-397, Jul. 2005.

Zhang et al., "Transcription activator-like effector nucleases enable efficient plant genome engineering," Plant Physiol., 161(1):20-7, Jan. 2013.
Zhang et al., "Efficient construction of sequence-specific TAL effectors for modulating mammalian transcription," Nat. Biotechnol., 29(2):149-53, 2011.
Zhang et al., "High frequency targeted mutagenesis in *Arabidopsis thaliana* using zinc finger nucleases," Proc. Natl. Acad. Sci. USA, 107(26):12028-33, May 2010.
Zhang et al., "RNAi effects on regulation of endogenous acid invertase activity in potato (*Solanum tuberosum* L.) tubers," Chin J Agric. Biotechnol, 5(2):107-111, Aug. 2008.
Zhu et al., "The C terminus of AvrXa10 can be replaced by the transcriptional activation domain of VP16 from the herpes simplex virus," Plant Cell, 11(9):1665-74, 1999.
Zhu et al., "AvrXa10 Contains an Acidic Transcriptional Activation Domain in the Functionally Conserved C Terminus," Mol. Plant Microbe Interac., 11(8): 824-32, 1998.
Zhu et al., "The rsma-like gene rsmA(XOO) of Xanthomonas orvzae pv. orvzae regulates bacterial virulence and production of diffusible signal factor," Mol. Plant Pathol., 12(3):227-37, 2011.
Zou et al., "Identification of an avirulence gene, avrxa5, from the rice pathogen Xanthomonas oryzae pv. oryzae," Sci. China Life Sci., 53(12):1440-9, 2010.
Zrenner et al., "Soluble acid invertase determines the hexose-to sucrose ratio in cold-stored potato tubers," Planta, 198(2):246-252, Feb. 1996.
Zuo and Chua, "Chemical-inducible systems for regulated expression of plant genes," Curr. Opin. Biotechnol., 11:146-51, 2000.
Zuo et al., "Technical advance: An estrogen receptor-based transactivator XVE mediates highly inducible gene expression in transgenic plants," Plant J., 24(2):265-273, Oct. 2000.
U.S. Appl. No. 14/629,859, filed Feb. 24, 2015, Daniel F. Voytas.
U.S. Appl. No. 15/025,690, filed Mar. 29, 2016, Daniel F. Voytas.
U.S. Appl. No. 16/344,496, filed Apr. 24, 2019, Javier Gil Humanes.
U.S. Appl. No. 17/022,421, filed Sep. 16, 2020, Daniel F. Voytas.
Datla et al., "A bifunctional fusion between beta-glucuronidase and neomycin phosphotransferase: a broad-spectrum marker enzyme for plants," Gene, 101(2):239-246, May 30, 1991.
Ebinuma et al., "Selection of marker-free transgenic plants using the isopentenyl transferase gene," Proc. Natl. Acad. Sci. USA, 94(6):2117-2121, Mar. 18, 1997.
Ellis et al., "Gene targeting with retroviral vectors: recombination by gene conversion into regions of nonhomology," Mol. Cell Biology, 9(4):1621-1627, Apr. 1989.
GenBank Accession No. AY279344.1, "Gene silencing vector pCPCbLCVB.002, complete sequence," dated Jun. 15, 2003, 3 pages.
GenBank Accession No. AY279345.1, "Gene silencing vector pCPCbLCVA.007, complete sequence," dated Jun. 15, 2003, 2 pages.
GenBank Accession No. AY279346.1, "Gene silencing vector pMTCbLCVA.008, complete sequence," dated Jun. 15, 2003, 3 pages.
Gilbertson et al., "Limitations on Geminivirus Genome Size Imposed by Plasmodesmata and Virus-Encoded Movement Protein: Insights into DNA Trafficking," Plant Cell, 15(11):2578-2591, Nov. 2003.
Hanin et al., "Plant genome modification by homologous recombination," Curr. Opin. Plant Biology, 6(2):157-162, Apr. 2003.
Hung et al., "Functional equivalence of late gene promoters in bean golden mosaic virus with those in tomato golden mosaic virus," J. Gen. Virology, 82(3):667-672, Mar. 2011.
Jin et al., "A single amino acid change in a geminiviral Rep protein differentiates between triggering a plant defence response and initiating viral DNA replication," J. Gen. Virology, 89(10):2636-2641, Oct. 2008.
Klug, "From Virus Structure to Chromatin: X-ray Diffraction to Three-Dimensional Electron Microscopy," Ann. Rev. Biochemistry, 79:1-35, Jan. 27, 2010.
Klug, "The Discovery of Zinc Fingers and Their Applications in Gene Regulation and Genome Manipulation," Ann. Rev. Biochemistry, 79:213-231, Jan. 4, 2010.

(56) References Cited

OTHER PUBLICATIONS

Martin et al., "New Vectors for Stable and Safe Gene Modification," Gene Therapy—Developments and Future Perspectives, Jun. 22, 2011, 1:3-30.
Nagar et al., "A geminivirus induces expression of a host DNA synthesis protein in terminally differentiated plant cells," Plant Cell, 7(6):705-719, Jun. 1995.
Palmer et al., "Investigation of the potential of maize streak virus to act as an infectious gene vector in maize plants," Arch. Virology, 146(6):1089-1104, Jun. 2001.
Russell et al., "Human gene targeting by viral vectors," Nat. Genetics, 18:325-330, Apr. 1, 1998.
Rybicki et al., "Virus-derived ssDNA vectors for the expression of foreign proteins in plants," Curr. Top. Microbiol. Immunology, 375:19-45, Oct. 29, 2011.
Stenger et al., "Replicational Release of Geminivirus Genomes from Tandemly Repeated Copies: Evidence for Rolling-Circle Replication of a Plant Viral DNA," Proc. Natl. Acad. Sci. USA, 88(18):8029-8033, Sep. 15, 1991.
Swoboda et al., "Identification of pronpl, a tobacco profilin gene activated in tip-growing cells," Plant Mol. Biology, 46:531-538, Jul. 2001.
Turnage et al., "Geminivirus-based vectors for gene silencing in Arabidopsis," Plant Journal, 30(1):107-114, Apr. 2002.
Wang et al., "Correction of a deletion mutant by gene targeting with an adenovirus vector," Mol. Cell. Biology, 13(2):918-927, Feb. 1993.
Zhang et al., "Bean Yellow Dwarf Virus replicons for high-level transgene expression in transgenic plants and cell cultures," Biotech. Bioengineering, 93(2):271-279, Feb. 5, 2006.

\* cited by examiner

Setaria calli

```
                        SEQUENCE LISTING

<160> NUMBER OF SEQ ID NOS: 94

<210> SEQ ID NO 1
<211> LENGTH: 18
<212> TYPE: DNA
<213> ORGANISM: Artificial Sequence
<220> FEATURE:
<223> OTHER INFORMATION: synthetic oligonucleotide

<400> SEQUENCE: 1
gagctcagta ctgcatgc                                                    18

<210> SEQ ID NO 2
<211> LENGTH: 45
<212> TYPE: DNA
<213> ORGANISM: Artificial Sequence
<220> FEATURE:
<223> OTHER INFORMATION: primer

<400> SEQUENCE: 2
gcggtaccct cgagtctaga tctgtctttt tccaaatatt tattg                      45

<210> SEQ ID NO 3
<211> LENGTH: 39
<212> TYPE: DNA
<213> ORGANISM: Artificial Sequence
<220> FEATURE:
<223> OTHER INFORMATION: primer

<400> SEQUENCE: 3
gcggtaccct cgagtctaga tttttgtggt ggttgcagc                             39

<210> SEQ ID NO 4
<211> LENGTH: 40
<212> TYPE: DNA
<213> ORGANISM: Artificial Sequence
<220> FEATURE:
<223> OTHER INFORMATION: primer

<400> SEQUENCE: 4
gcggtaccct cgagtctaga caagattctc ttcacttctc                            40

<210> SEQ ID NO 5
<211> LENGTH: 39
<212> TYPE: DNA
<213> ORGANISM: Artificial Sequence
<220> FEATURE:
```

<223> OTHER INFORMATION: primer

<400> SEQUENCE: 5
aggctagcga gctcagatct ccttgtcaag aggagcatc                    39

<210> SEQ ID NO 6
<211> LENGTH: 43
<212> TYPE: DNA
<213> ORGANISM: Artificial Sequence
<220> FEATURE:
<223> OTHER INFORMATION: primer

<400> SEQUENCE: 6
aggctagcga gctcagatct tttgccatta atggagaatc ttg               43

<210> SEQ ID NO 7
<211> LENGTH: 39
<212> TYPE: DNA
<213> ORGANISM: Artificial Sequence
<220> FEATURE:
<223> OTHER INFORMATION: primer

<400> SEQUENCE: 7
aggctagcga gctcagatct caatgacgac actccccac                    39

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
gcatgcagta ctgagctcgc cgaagatacg tggaaac                      37

<210> SEQ ID NO 9
<211> LENGTH: 37
<212> TYPE: DNA
<213> ORGANISM: Artificial Sequence
<220> FEATURE:
<223> OTHER INFORMATION: primer

<400> SEQUENCE: 9
gagctcagta ctgcatgcgc tggagggtaa tagaaac                      37

<210> SEQ ID NO 10
<211> LENGTH: 24
<212> TYPE: DNA
<213> ORGANISM: Artificial Sequence
<220> FEATURE:
<223> OTHER INFORMATION: primer

<400> SEQUENCE: 10
gattaggcta gcgagctcag atct                                    24

<210> SEQ ID NO 11
<211> LENGTH: 24
<212> TYPE: DNA
<213> ORGANISM: Artificial Sequence
<220> FEATURE:
<223> OTHER INFORMATION: primer

<400> SEQUENCE: 11
cggacagatt attcgatgca aagg                                    24

```
<210> SEQ ID NO 12
<211> LENGTH: 25
<212> TYPE: DNA
<213> ORGANISM: Artificial Sequence
<220> FEATURE:
<223> OTHER INFORMATION: primer

<400> SEQUENCE: 12
gacaaaccac aactgacaat acaga                                              25

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gcggtaccct cgagtctaga                                                    20

<210> SEQ ID NO 14
<211> LENGTH: 24
<212> TYPE: DNA
<213> ORGANISM: Artificial Sequence
<220> FEATURE:
<223> OTHER INFORMATION: primer

<400> SEQUENCE: 14
tcaccatcgt gaatcatccc tcct                                               24

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15
tcgagtctag acacaatcac acaaaactaa caaaag                                  36

<210> SEQ ID NO 16
<211> LENGTH: 33
<212> TYPE: DNA
<213> ORGANISM: Artificial Sequence
<220> FEATURE:
<223> OTHER INFORMATION: primer

<400> SEQUENCE: 16
gctcagatct gcaccaagac caaaaatggc aac                                     33

<210> SEQ ID NO 17
<211> LENGTH: 39
<212> TYPE: DNA
<213> ORGANISM: Artificial Sequence
<220> FEATURE:
<223> OTHER INFORMATION: primer

<400> SEQUENCE: 17
gcatgcagta ctgagctcac gtggaaacaa cggtgtttg                               39

<210> SEQ ID NO 18
<211> LENGTH: 38
<212> TYPE: DNA
<213> ORGANISM: Artificial Sequence
<220> FEATURE:
<223> OTHER INFORMATION: primer
```

<400> SEQUENCE: 18
gagctcagta ctgcatgcta atagaaacac taatcttc        38

<210> SEQ ID NO 19
<211> LENGTH: 24
<212> TYPE: DNA
<213> ORGANISM: Artificial Sequence
<220> FEATURE:
<223> OTHER INFORMATION: primer

<400> SEQUENCE: 19
tgccacgtgg acgaatacta gcaa        24

<210> SEQ ID NO 20
<211> LENGTH: 24
<212> TYPE: DNA
<213> ORGANISM: Artificial Sequence
<220> FEATURE:
<223> OTHER INFORMATION: primer

<400> SEQUENCE: 20
gcttgaatca tggcctgaac gctt        24

<210> SEQ ID NO 21
<211> LENGTH: 16
<212> TYPE: DNA
<213> ORGANISM: Artificial Sequence
<220> FEATURE:
<223> OTHER INFORMATION: primer

<400> SEQUENCE: 21
gagctcagta ctgcat        16

<210> SEQ ID NO 22
<211> LENGTH: 16
<212> TYPE: DNA
<213> ORGANISM: Artificial Sequence
<220> FEATURE:
<223> OTHER INFORMATION: primer

<400> SEQUENCE: 22
gcatgcagta ctgagc        16

<210> SEQ ID NO 23
<211> LENGTH: 24
<212> TYPE: DNA
<213> ORGANISM: Artificial Sequence
<220> FEATURE:
<223> OTHER INFORMATION: primer

<400> SEQUENCE: 23
ttacggtttt tcaccgaagt tcat        24

<210> SEQ ID NO 24
<211> LENGTH: 39
<212> TYPE: DNA
<213> ORGANISM: Artificial Sequence
<220> FEATURE:
<223> OTHER INFORMATION: primer

<400> SEQUENCE: 24
ttcggtgaaa aaccgtaaac cgacctgtcc ggtgccctg        39

<210> SEQ ID NO 25
<211> LENGTH: 32

```
<212> TYPE: DNA
<213> ORGANISM: Artificial Sequence
<220> FEATURE:
<223> OTHER INFORMATION: primer

<400> SEQUENCE: 25
actgatctag acactggcgg aagcaacgcg ta                              32

<210> SEQ ID NO 26
<211> LENGTH: 32
<212> TYPE: DNA
<213> ORGANISM: Artificial Sequence
<220> FEATURE:
<223> OTHER INFORMATION: primer

<400> SEQUENCE: 26
tcagtagatc tgccatgatg gatactttct cg                              32

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
gccatgatgg atactttctc g                                          21

<210> SEQ ID NO 28
<211> LENGTH: 95
<212> TYPE: DNA
<213> ORGANISM: Artificial Sequence
<220> FEATURE:
<223> OTHER INFORMATION: primer

<400> SEQUENCE: 28
caacttttgt atacaaagtt ggcattataa aaaagcattg ctcatcaatt tgttgcaacg    60
aacaggtcac tatcagtcaa aataaaatca ttatt                               95

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
aagctcgggc ccaataatga ttttattttg                                 30

<210> SEQ ID NO 30
<211> LENGTH: 48
<212> TYPE: DNA
<213> ORGANISM: Artificial Sequence
<220> FEATURE:
<223> OTHER INFORMATION: primer

<400> SEQUENCE: 30
ctttgtatac aaaagttgcc gagctcgcgg ccgcattagg caccccag              48

<210> SEQ ID NO 31
<211> LENGTH: 46
<212> TYPE: DNA
<213> ORGANISM: Artificial Sequence
<220> FEATURE:
<223> OTHER INFORMATION: primer
```

<400> SEQUENCE: 31

```
aactttgtac aagaaagctg ggtcgtcgac ctgcagactg gctgtg           46
```

<210> SEQ ID NO 32
<211> LENGTH: 497
<212> TYPE: DNA
<213> ORGANISM: Artificial Sequence
<220> FEATURE:
<223> OTHER INFORMATION: primer

<400> SEQUENCE: 32

```
aggaagtgag acggaaattt aataacggcg agataaactt ttaataggac gtccgatcgt    60
tcaaacattt ggcaataaag tttcttaaga ttgaatcctg ttgccggtct tgcgatgatt   120
atcatataat ttctgttgaa ttacgttaag catgtaataa ttaacatgta atgcatgacg   180
ttatttatga gatgggtttt tatgattaga gtcccgcaat tatacattta atacgcgata   240
gaaaacaaaa tatagcgcgc aaactaggat aaattatcgc gcgcggtgtc atctatgtta   300
ctagatcggg aattgatccc ccctcgacag cttccgaaa gggcgaattc gcaactttgt   360
atacaaaagt tgaacgagaa acgtaaaatg atataaatat caatatatta aattagattt   420
tgcataaaaa acagactaca taatactgta aaacacaaca tatccagtca ctatgccatc   480
cagctgatat cccctat                                                  497
```

<210> SEQ ID NO 33
<211> LENGTH: 500
<212> TYPE: DNA
<213> ORGANISM: Artificial Sequence
<220> FEATURE:
<223> OTHER INFORMATION: primer

<400> SEQUENCE: 33

```
cgacggccag tcttaagctc gggccccaaa taatgatttt attttgactg atagtgacct    60
gttcgttgca acaaattgat gagcaatgct ttttataat gccaactttg tacaaaaaag   120
caggctccga attcatgcct tctgctagta agaacttcag actccaatct aaatatgttt   180
tccttaccta tcccaagtgc tcatctcaaa gagatgattt attccagttt ctctgggaga   240
aactcacacc ttttcttatt ttcttccttg gtgttgcttc tgagcttcat caagatggca   300
ctacccacta tcatgctctt ctccagcttg ataaaaaacc ttgtattagg gatccttctt   360
ttttcgattt tgaaggaaat caccctaata tccagccagc tagaaactct aaacaagtcc   420
ttgattacat atcaaaggac ggagatatta aaccagagg agatttccga gatcataagg   480
tctctcctcg caaatctgac                                               500
```

<210> SEQ ID NO 34
<211> LENGTH: 500
<212> TYPE: DNA
<213> ORGANISM: Artificial Sequence
<220> FEATURE:
<223> OTHER INFORMATION: primer

<400> SEQUENCE: 34

```
attaaaacca gaggagattt ccgagatcat aaggtctctc ctcgcaaatc tgacgcacga    60
tggagaacta ttatccagac tgcaacgtct aaggaggaat atcttgacat gatcaaggaa   120
gaattccctc atgaatgggc aacaaagctt caatggctgg aatattcagc caacaaatta   180
ttccctccac aacctgaacc gtatgtgtcg cccttcacag aatcagatct tcgctgccac   240
gaagatctac actcctggag ggaaacccat ctataccatg taagcataga cgcttatact   300
```

```
tacatacatc ctgtctcata ccaacaagct caatctgacc ttgaatggat ggccgattta      360
accaggacaa tggaaggaat ggaatccgac accccagcct ctacatctgc ggaccaactc      420
gtaccggaaa gaccacctgg gctagaagtc tcggacgaca caactattgg aacggtacca      480
tcgatttcac caactacgat                                                  500

<210> SEQ ID NO 35
<211> LENGTH: 500
<212> TYPE: DNA
<213> ORGANISM: Artificial Sequence
<220> FEATURE:
<223> OTHER INFORMATION: primer

<400> SEQUENCE: 35
attaaaacca gaggagattt ccgagatcat aaggtctctc ctcgcaaatc tgacgcacga       60
tggagaacta ttatccagac tgcaacgtct aaggaggaat atcttgacat gatcaaggaa      120
gaattccctc atgaatgggc aacaaagctt caatggctgg aatattcagc caacaaatta      180
ttccctccac aacctgaacc gtatgtgtcg cccttcacag aatcagatct tcgctgccac      240
caagatctac actcctggag ggaaacccat ctataccatg taagcataga cgcttatact      300
tacatacatc ctgtctcata ccaacaagct caatctgacc ttgaatggat ggccgattta      360
accaggacaa tggaaggaat ggaatccgac accccagcct ctacatctgc ggaccaactc      420
gtaccggaaa gaccacctgg gctagaagtc tcggacgaca caactattgg aacggtacca      480
tcgatttcac caactacgat                                                  500

<210> SEQ ID NO 36
<211> LENGTH: 500
<212> TYPE: DNA
<213> ORGANISM: Artificial Sequence
<220> FEATURE:
<223> OTHER INFORMATION: primer

<400> SEQUENCE: 36
gtaccggaaa gaccacctgg gctagaagtc tcggacgaca caactattgg aacggtacca       60
tcgatttcac caactacgat gaacacgcca cctataatat catcgacgac atcccccttca    120 agttcgtccc attgtggaag caattaatag gttgccagtc tgatttcact gtcaaccta      180 aatatgaaa aagaagaaa ataaaggtg ggatcccttc tataattctt tgcaatcctg        240
acgaagactg gatgttatca atgacaagtc aacagaagga ttactttaaa gataattgcg      300
tcacccacta catgtgtgac ggggagactt ttttgctcg ggaatcgtcg agtcactgaa       360
cgtgcctgaa ttcgacccag ctttcttgta caaagttggc attataaaaa ataattgctc      420
atcaatttgt tgcaacgaac aggtcactat cagtcaaaat aaaatcatta tttgccatcc      480
agctgatatc ccctatagtg                                                  500

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
cgacggccag tcttaagctc                                                   20

<210> SEQ ID NO 38
```

```
<211> LENGTH: 20
<212> TYPE: DNA
<213> ORGANISM: Artificial Sequence
<220> FEATURE:
<223> OTHER INFORMATION: primer

<400> SEQUENCE: 38
cactataggg gatatcagct                                              20

<210> SEQ ID NO 39
<211> LENGTH: 33
<212> TYPE: DNA
<213> ORGANISM: Artificial Sequence
<220> FEATURE:
<223> OTHER INFORMATION: primer

<400> SEQUENCE: 39
agcttggtac ccctgcaggt agcagaaggc atg                               33

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
ataagcacaa gttttatccg gc                                           22

<210> SEQ ID NO 41
<211> LENGTH: 27
<212> TYPE: DNA
<213> ORGANISM: Artificial Sequence
<220> FEATURE:
<223> OTHER INFORMATION: primer

<400> SEQUENCE: 41
ggatcctcta gattacgccc cgcctgc                                      27

<210> SEQ ID NO 42
<211> LENGTH: 31
<212> TYPE: DNA
<213> ORGANISM: Artificial Sequence
<220> FEATURE:
<223> OTHER INFORMATION: primer

<400> SEQUENCE: 42
cgtaatctag aggatccggc ttactaaaag c                                 31

<210> SEQ ID NO 43
<211> LENGTH: 32
<212> TYPE: DNA
<213> ORGANISM: Artificial Sequence
<220> FEATURE:
<223> OTHER INFORMATION: primer

<400> SEQUENCE: 43
tgttgaccga gctcctgcag aagcttctcg ag                                32

<210> SEQ ID NO 44
<211> LENGTH: 487
<212> TYPE: DNA
<213> ORGANISM: Artificial Sequence
<220> FEATURE:
<223> OTHER INFORMATION: primer

<400> SEQUENCE: 44
```

```
cctgcaggta gcagaaggca tgttgttgtg actccgaggg gttgcctcaa actctatctt      60
ataaccggcg tggaggcatg gaggcagggg tattttggtc attttaatag atagtggaaa     120
atgacgtgga atttacttaa agacgaagtc gagacctttg cgactctaga ggtctcaaat     180
ttaatattac cggcgtggcc ccccttatc gcgagtgctt tagcacgagc ggtccagatt      240
taaagtagaa aatttcccgc ccactagggt taaaggtgtt cacactataa agcatatac     300 gatgtgatgg tatttgatgg agcgtatatt gtatcaggta tttccgttgg atacgaatta     360
ttcgtacgac cctccctaag attcttgatt gtttataaaa ccaaatctca ttgtctttgt     420
tgtgtattgt ttgcaggacg tcgagagttc tcaacacaac atatacaaaa caaacgaatc     480
tcaagca                                                              487
```

<210> SEQ ID NO 45
<211> LENGTH: 482
<212> TYPE: DNA
<213> ORGANISM: Artificial Sequence
<220> FEATURE:
<223> OTHER INFORMATION: primer

<400> SEQUENCE: 45

```
acaaaacaaa cgaatctcaa gcaatcaagc attctacttc tattgcagca atttaaatca     60
tttctacaag tttgtacaaa aaagctgaac gagaaacgta aaatgatata aatatcaata    120
tattaaatta gattttgcat aaaaaacaga ctacataata ctgtaaaaca caacatatcc    180
agtcactatg gcggccgcat taggcaccc aggctttaca cttttatgctt ccggctcgta    240 taatgtgtgg attttgagtt aggatccgtc gagattttca ggagctaagg aagctaaaat    300
ggagaaaaaa atcactggat ataccaccgt tgatatatcc caatggcatc gtaaagaaca    360
ttttgaggca tttcagtcag ttgctcaatg tacctataac cagaccgttc agctggatat    420
tacggccttt ttaaagaccg taagaaaaaa taagcacaag ttttatccgg cctttattca    480
ca                                                                   482
```

<210> SEQ ID NO 46
<211> LENGTH: 27
<212> TYPE: DNA
<213> ORGANISM: Artificial Sequence
<220> FEATURE:
<223> OTHER INFORMATION: primer

<400> SEQUENCE: 46

```
ctatggtcga cctgcagact ggctgtg                                         27
```

<210> SEQ ID NO 47
<211> LENGTH: 35
<212> TYPE: DNA
<213> ORGANISM: Artificial Sequence
<220> FEATURE:
<223> OTHER INFORMATION: primer

<400> SEQUENCE: 47

```
gggatcccac tcgagggtca acatggtgga gcacg                                35
```

<210> SEQ ID NO 48
<211> LENGTH: 21
<212> TYPE: DNA
<213> ORGANISM: Artificial Sequence
<220> FEATURE:
<223> OTHER INFORMATION: primer

<400> SEQUENCE: 48
ctagagtcga ggtcctctcc a                                             21

<210> SEQ ID NO 49
<211> LENGTH: 500
<212> TYPE: DNA
<213> ORGANISM: Artificial Sequence
<220> FEATURE:
<223> OTHER INFORMATION: primer

<400> SEQUENCE: 49
aggtggctcc tacaaatgcc atcattgcga taaaggaaag gccatcgttg aagatgcctc    60
tgccgacagt ggtcccaaag atggacccccc acccacgagg agcatcgtgg aaaaagaaga  120
cgttccaacc acgtcttcaa agcaagtgga ttgatgtgat atctccactg acgtaaggga   180
tgacgcacaa tcccactatc cttcgcaaga cccttcctct atataaggaa gttcatttca   240
tttggagagg acctcgactc tagccttcct ctatataagg aagttcattt catttggaga   300
ggtaagtttc acttcacaca ttattactgt cttctaatac aaggttttt atcaagctgg    360 agaagagcat gatagtgggt agtgccatct tgatgaagct cagaagcaac accaaggaag   420
aaaataagaa aaggtgtgag tttctcccag agaaactgga ataaatcatc tctttgagat   480
gagcacttgg gataggtaag                                              500

<210> SEQ ID NO 50
<211> LENGTH: 500
<212> TYPE: DNA
<213> ORGANISM: Artificial Sequence
<220> FEATURE:
<223> OTHER INFORMATION: primer

<400> SEQUENCE: 50
tgagatgagc acttgggata ggtaaggaaa acatatttag attggagtct gaagttctta    60
ctagcagaag gcatgttgtt gtgactccga ggggttgcct caaactctat cttataaccg   120
gcgtggaggc atggaggcag gggtattttg gtcattttaa tagatagtgg aaaatgacgt   180
ggaatttact taaagacgaa gtcgagacct ttgcgactct agaggtctca atttaatatt   240
accggcgtgg ccccccctta tcgcgagtgc tttagcacga gcggtccaga tttaaagtag   300
aaaatttccc gcccactagg gttaaaggtg ttcacactat aaaagcatat acgatgtgat   360
ggtatttgat ggagcgtata ttgtatcagg tatttccgtt ggatacgaat tattcgtacg   420
accctcatag tttaaactga aggcgggaaa cgacaatctg atccaagctc aagctaagct   480
tgcatgcctg caggatatcg                                              500

<210> SEQ ID NO 51
<211> LENGTH: 28
<212> TYPE: DNA
<213> ORGANISM: Artificial Sequence
<220> FEATURE:
<223> OTHER INFORMATION: primer

<400> SEQUENCE: 51
cgatatcctg caggcatgca agcttagc                                      28

<210> SEQ ID NO 52
<211> LENGTH: 31
<212> TYPE: DNA
<213> ORGANISM: Artificial Sequence
<220> FEATURE:
<223> OTHER INFORMATION: primer

<400> SEQUENCE: 52
aagtctttgc gacaaggggg ggcccacgcc g                          31

<210> SEQ ID NO 53
<211> LENGTH: 31
<212> TYPE: DNA
<213> ORGANISM: Artificial Sequence
<220> FEATURE:
<223> OTHER INFORMATION: primer

<400> SEQUENCE: 53
aattcggcgt gggcccccc ttgtcgcaaa g                           31

<210> SEQ ID NO 54
<211> LENGTH: 500
<212> TYPE: DNA
<213> ORGANISM: Artificial Sequence
<220> FEATURE:
<223> OTHER INFORMATION: primer

<400> SEQUENCE: 54
cacagccagt ctgcaggtcg accatagtga ctggatatgt tgtgttttac agtattatgt      60
agtctgtttt ttatgcaaaa tctaatttaa tatattgata tttatatcat tttacgtttc     120
tcgttcagct tccttgtaca aagtggtgag tgtacttcaa gtcagtggga aatcaataaa     180
atgattattt tatgaatata tttcattgtg caagtagata gaaattacat atgttacata     240
acacacgaaa taaacaaaaa aagacaatcc aaaaacaaac accccaaaaa aaataatcac     300
tttagataaa ctcgtatgag gagaggcacg ttcagtgact cgacgattcc cgagcaaaaa     360
aagtctcccc gtcacacatg tagtgggtga cgcaattatc tttaaagtaa tccttctgtt     420
gacttgtcat tgataacatc cagtcttcgt caggattgca agaattata gaagggatcc      480 cactcgagaa gcttctgcag                                              500

<210> SEQ ID NO 55
<211> LENGTH: 39
<212> TYPE: DNA
<213> ORGANISM: Artificial Sequence
<220> FEATURE:
<223> OTHER INFORMATION: primer

<400> SEQUENCE: 55
acctcgactc tagaatgaag actaatcttt ttctctttc                          39

<210> SEQ ID NO 56
<211> LENGTH: 39
<212> TYPE: DNA
<213> ORGANISM: Artificial Sequence
<220> FEATURE:
<223> OTHER INFORMATION: primer

<400> SEQUENCE: 56
gaacgatcgg acgtcttaaa gctcatcatg tttgtatag                          39

<210> SEQ ID NO 57
<211> LENGTH: 37
<212> TYPE: DNA
<213> ORGANISM: Artificial Sequence
<220> FEATURE:
<223> OTHER INFORMATION: primer

<400> SEQUENCE: 57

```
gcccttcacc atggcttcct cccctccaaa gaaaaag                                   37
```

<210> SEQ ID NO 58
<211> LENGTH: 40
<212> TYPE: DNA
<213> ORGANISM: Artificial Sequence
<220> FEATURE:
<223> OTHER INFORMATION: primer

<400> SEQUENCE: 58

```
gaacgatcgg acgtcctatt aaaagtttat ctcaccgtta                               40
```

<210> SEQ ID NO 59
<211> LENGTH: 24
<212> TYPE: DNA
<213> ORGANISM: Artificial Sequence
<220> FEATURE:
<223> OTHER INFORMATION: primer

<400> SEQUENCE: 59

```
tgccgccgtg ttccggctgt cagc                                                24
```

<210> SEQ ID NO 60
<211> LENGTH: 24
<212> TYPE: DNA
<213> ORGANISM: Artificial Sequence
<220> FEATURE:
<223> OTHER INFORMATION: primer

<400> SEQUENCE: 60

```
aaggtgcacg ggaatatttc gcgc                                                24
```

<210> SEQ ID NO 61
<211> LENGTH: 24
<212> TYPE: DNA
<213> ORGANISM: Artificial Sequence
<220> FEATURE:
<223> OTHER INFORMATION: primer

<400> SEQUENCE: 61

```
gtttcacttc acacattatt actg                                                24
```

<210> SEQ ID NO 62
<211> LENGTH: 24
<212> TYPE: DNA
<213> ORGANISM: Artificial Sequence
<220> FEATURE:
<223> OTHER INFORMATION: primer

<400> SEQUENCE: 62

```
tgttgagaac tctcgacgtc ctgc                                                24
```

<210> SEQ ID NO 63
<211> LENGTH: 24
<212> TYPE: DNA
<213> ORGANISM: Artificial Sequence
<220> FEATURE:
<223> OTHER INFORMATION: primer

<400> SEQUENCE: 63

```
gtgtgaacaa cgaactgaac tggc                                                24
```

<210> SEQ ID NO 64
<211> LENGTH: 23
<212> TYPE: DNA
<213> ORGANISM: Artificial Sequence

```
<220> FEATURE:
<223> OTHER INFORMATION: primer

<400> SEQUENCE: 64
agagcgccca atacgcaaac cgc                                        23

<210> SEQ ID NO 65
<211> LENGTH: 24
<212> TYPE: DNA
<213> ORGANISM: Artificial Sequence
<220> FEATURE:
<223> OTHER INFORMATION: primer

<400> SEQUENCE: 65
cagcgagtca gtgagcgagg aagc                                       24

<210> SEQ ID NO 66
<211> LENGTH: 33
<212> TYPE: DNA
<213> ORGANISM: Artificial Sequence
<220> FEATURE:
<223> OTHER INFORMATION: primer

<400> SEQUENCE: 66
agctagtcta gaatgttacg tcctgtagaa acc                             33

<210> SEQ ID NO 67
<211> LENGTH: 31
<212> TYPE: DNA
<213> ORGANISM: Artificial Sequence
<220> FEATURE:
<223> OTHER INFORMATION: primer

<400> SEQUENCE: 67
gtacgtgacg tctcattgtt tgcctccctg c                               31

<210> SEQ ID NO 68
<211> LENGTH: 21
<212> TYPE: DNA
<213> ORGANISM: Artificial Sequence
<220> FEATURE:
<223> OTHER INFORMATION: primer

<400> SEQUENCE: 68
gacggtgcag aaagtgaagt a                                          21

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
tatggcccag gagtgtctaa                                            20

<210> SEQ ID NO 70
<211> LENGTH: 48
<212> TYPE: DNA
<213> ORGANISM: Artificial Sequence
<220> FEATURE:
<223> OTHER INFORMATION: primer

<400> SEQUENCE: 70
caagctaagc ttgcatgcct gcagggtgtt tgacaggata tattggcg             48
```

-continued

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
tccatgccgc ctcctttagc                                                      20

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
gctaaaggag gcggcatgga                                                      20

<210> SEQ ID NO 73
<211> LENGTH: 22
<212> TYPE: DNA
<213> ORGANISM: Artificial Sequence
<220> FEATURE:
<223> OTHER INFORMATION: primer

<400> SEQUENCE: 73
accacttcaa gaactctgta gc                                                   22

<210> SEQ ID NO 74
<211> LENGTH: 23
<212> TYPE: DNA
<213> ORGANISM: Artificial Sequence
<220> FEATURE:
<223> OTHER INFORMATION: primer

<400> SEQUENCE: 74
gctacagagt tcttgaagtg gtg                                                  23

<210> SEQ ID NO 75
<211> LENGTH: 47
<212> TYPE: DNA
<213> ORGANISM: Artificial Sequence
<220> FEATURE:
<223> OTHER INFORMATION: primer

<400> SEQUENCE: 75
aggcacgttc agtgactcga cgaagtagat gccgaccgga tctgtcg                        47

<210> SEQ ID NO 76
<211> LENGTH: 46
<212> TYPE: DNA
<213> ORGANISM: Artificial Sequence
<220> FEATURE:
<223> OTHER INFORMATION: primer

<400> SEQUENCE: 76
gaagttctta ctagcagaag gcatcggatc tgcgaaagct cgagag                         46

<210> SEQ ID NO 77
<211> LENGTH: 50
<212> TYPE: DNA
<213> ORGANISM: Artificial Sequence
<220> FEATURE:
<223> OTHER INFORMATION: primer

<400> SEQUENCE: 77

| | | |
|---|---|---|
| gtcacaacaa catgccttct gctacctgca ggcgtaatca tggtcatagc | | 50 |

<210> SEQ ID NO 78
<211> LENGTH: 3971
<212> TYPE: DNA
<213> ORGANISM: Artificial Sequence
<220> FEATURE:
<223> OTHER INFORMATION: plasmid

<400> SEQUENCE: 78

| | | |
|---|---|---|
| aagcagaagg catgttgttg tgactccgag gggttgcctc aaactctatc ttataaccgg | | 60 |
| cgtggaggca tggaggcagg ggtattttgg tcattttaat agatagtgga aaatgacgtg | | 120 |
| gaatttactt aaagacgaag tctttgcgac aaggggggc ccacgccgaa tttaatatta | | 180 |
| ccggcgtggc ccccccttat cgcgagtgct ttagcacgag cggtccagat ttaaagtaga | | 240 |
| aaatttcccg cccactaggg ttaaaggtgt tcacactata aaagcatata cgatgtgatg | | 300 |
| gtatttgatg gagcgtatat tgtatcaggt atttccgttg gatacgaatt attcgtacga | | 360 |
| ccctccctaa gattcttgat tgtttataaa accaaatctc attgtctttg ttgtgtattg | | 420 |
| tttgcaggac gtcgagagtt ctcaacacaa catatacaaa acaaacgaat ctcaagcaat | | 480 |
| caagcattct acttctattg cagcaattta aatcatttct acaagtttgt acaaaaaagc | | 540 |
| tgaacgagaa acgtaaaatg atataaatat caatatatta aattagattt tgcataaaaa | | 600 |
| acagactaca taatactgta aaacacaaca tatccagtca ctatggcggc cgcattaggc | | 660 |
| accccaggct ttacacttta tgcttccggc tcgtataatg tgtggatttt gagttaggat | | 720 |
| ccgtcgagat tttcaggagc taaggaagct aaaatggaga aaaaaatcac tggatatacc | | 780 |
| accgttgata tatcccaatg gcatcgtaaa gaacattttg aggcatttca gtcagttgct | | 840 |
| caatgtacct ataaccagac cgttcagctg gatattacgg cctttttaaa gaccgtaaag | | 900 |
| aaaaataagc acaagtttta tccggccttt attcacattc ttgcccgcct gatgaatgct | | 960 |
| catccggaat tccgtatggc aatgaaagac ggtgagctgg tgatatggga tagtgttcac | | 1020 |
| ccttgttaca ccgttttcca tgagcaaact gaaacgtttt catcgctctg gagtgaatac | | 1080 |
| cacgacgatt tccggcagtt tctacacata tattcgcaag atgtggcgtg ttacggtgaa | | 1140 |
| aacctggcct atttccctaa agggtttatt gagaatatgt ttttcgtctc agccaatccc | | 1200 |
| tgggtgagtt tcaccagttt tgatttaaac gtggccaata tggacaactt cttcgccccc | | 1260 |
| gttttcacca tgggcaaata ttatacgcaa ggcgacaagg tgctgatgcc gctggcgatt | | 1320 |
| caggttcatc atgccgtttg tgatggcttc catgtcggca gaatgcttaa tgaattacaa | | 1380 |
| cagtactgcg atgagtggca ggcggggcgt aatctagagg atccggctta ctaaaagcca | | 1440 |
| gataacagta tgcgtatttg cgcgctgatt tttgcggtat aagaatatat actgatatgt | | 1500 |
| atacccgaag tatgtcaaaa agaggtatgc tatgaagcag cgtattacag tgacagttga | | 1560 |
| cagcgacagc tatcagttgc tcaaggcata tatgatgtca atatctccgg tctggtaagc | | 1620 |
| acaaccatgc agaatgaagc ccgtcgtctg cgtgccgaac gctggaaagc ggaaaatcag | | 1680 |
| gaagggatgg ctgaggtcgc ccggtttatt gaaatgaacg gctctttgc tgacgagaac | | 1740 |
| aggggctggt gaaatgcagt ttaaggttta cacctataaa agagagagcc gttatcgtct | | 1800 |
| gtttgtggat gtacagagtg atattattga cacgccggg cgacggatgg tgatcccct | | 1860 |
| ggccagtgca cgtctgctgt cagataaagt ccccccgtgaa ctttacccgg tggtgcatat | | 1920 |

```
cggggatgaa agctggcgca tgatgaccac cgatatggcc agtgtgccgg tctccgttat    1980
cggggaagaa gtggctgatc tcagccaccg cgaaaatgac atcaaaaacg ccattaacct    2040
gatgttctgg ggaatataaa tgtcaggctc cctTatacac agccagtctg caggtcgacc    2100
atagtgactg gatatgttgt gttttacagt attatgtagt ctgttttttA tgcaaaatct    2160
aatttaatat attgatattt atatcatttt acgtttctcg ttcagctttc ttgtacaaag    2220
tggtgagtgt acttcaagtc agtgggaaat caataaaatg attattttat gaatatattt    2280
cattgtgcaa gtagatagaa attacatatg ttacataaca cacgaaataa acaaaaaaag    2340
acaatccaaa aacaaacacc ccaaaaaaaa taatcacttt agataaactc gtatgaggag    2400
aggcacgttc agtgactcga cgattcccga gcaaaaaaag tctccccgtc acacatgtag    2460
tgggtgacgc aattatcttt aaagtaatcc ttctgttgac ttgtcattga taacatccag    2520
tcttcgtcag gattgcaaag aattatagaa gggatcccac tcgagggtca acatggtgga    2580
gcacgacaca cttgtctact ccaaaaatat caaagataca gtctcagaag accaaagggc    2640
aattgagact tttcaacaaa gggtaatatc cggaaacctc ctcggattcc attgcccagc    2700
tatctgtcac tttattgtga agatagtgga aaggaaggt ggctcctaca aatgccatca    2760
ttgcgataaa ggaaaggcca tcgttgaaga tgcctctgcc gacagtggtc ccaaagatgg    2820
acccccaccc acgaggagca tcgtggaaaa agaagacgtt ccaaccacgt cttcaaagca    2880
agtggattga tgtgataaca tggtggagca cgacacactt gtctactcca aaatatcaa    2940
agatacagtc tcagaagacc aaagggcaat tgagactttt caacaaaggg taatatccgg    3000
aaacctcctc ggattccatt gcccagctat ctgtcacttt attgtgaaga tagtggaaaa    3060
ggaaggtggc tcctacaaat gccatcattg cgataaagga aaggccatcg ttgaagatgc    3120
ctctgccgac agtggtccca agatggaccc ccacccacg aggagcatcg tggaaaaaga    3180
agacgttcca accacgtctt caaagcaagt ggattgatgt gatatctcca ctgacgtaag    3240
ggatgacgca caatcccact atccttcgca agacccttcc tctatataag gaagttcatt    3300
tcatttggag aggacctcga ctctagagga tccccttcc tctatataag gaagttcatt    3360
tcatttggag aggtaagttt cacttcacac attattactg tcttctaata caaggttttt    3420
tatcaagctg gagaagagca tgatagtggg tagtgccatc ttgatgaagc tcagaagcaa    3480
caccaaggaa gaaataaga aaaggtgtga gtttctccca gagaaactgg aataaatcat    3540
ctctttgaga tgagcacttg ggataggtaa ggaaaacata tttagattgg agtctgaagt    3600
tcttactagc agaaggcatg ttgttgtgac tccgaggggt tgcctcaaac tctatcttat    3660
aaccggcgtg gaggcatgga ggcaggggta ttttggtcat tttaatagat agtggaaaat    3720
gacgtggaat ttacttaaag acgaagtctt tgcgacaagg gggggcccac gccgaattta    3780
atattaccgg cgtggccccc ccttatcgcg agtgctttag cacgagcggt ccagatttaa    3840
agtagaaaat tccccgccca ctagggttaa aggtgttcac actataaaag catatacgat    3900
gtgatggtat ttgatggagc gtatattgta tcaggtattt ccgttggata cgaattattc    3960
gtacgaccct c                                                        3971
```

<210> SEQ ID NO 79
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 79

```
cgcccacgca ttaaagcgtg ggcgaaccga cctg                          34
```

<210> SEQ ID NO 80
<211> LENGTH: 30
<212> TYPE: DNA
<213> ORGANISM: Artificial Sequence
<220> FEATURE:
<223> OTHER INFORMATION: synthetic oligonucleotide

<400> SEQUENCE: 80

```
cgcccacgca tgcgtgggcg aaccgacctg                               30
```

<210> SEQ ID NO 81
<211> LENGTH: 29
<212> TYPE: DNA
<213> ORGANISM: Artificial Sequence
<220> FEATURE:
<223> OTHER INFORMATION: synthetic oligonucleotide

<400> SEQUENCE: 81

```
cgcccacgca gcgtgggcga accgacctg                                29
```

<210> SEQ ID NO 82
<211> LENGTH: 26
<212> TYPE: DNA
<213> ORGANISM: Artificial Sequence
<220> FEATURE:
<223> OTHER INFORMATION: synthetic oligonucleotide

<400> SEQUENCE: 82

```
cgcccacgcg tgggcgaacc gacctg                                   26
```

<210> SEQ ID NO 83
<211> LENGTH: 33
<212> TYPE: DNA
<213> ORGANISM: Nicotiana tabacum

<400> SEQUENCE: 83

```
tcatgaatgt gcaggagcta gcaactatta agg                           33
```

<210> SEQ ID NO 84
<211> LENGTH: 35
<212> TYPE: DNA
<213> ORGANISM: Artificial Sequence
<220> FEATURE:
<223> OTHER INFORMATION: synthetic oligonucleotide

<400> SEQUENCE: 84

```
tcatgaatgt gcaggagcgc tagcaactat taagg                         35
```

<210> SEQ ID NO 85
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 85

```
tcatgaatgt gcaggagtag caactattaa gg                            32
```

<210> SEQ ID NO 86
<211> LENGTH: 29
<212> TYPE: DNA
<213> ORGANISM: Artificial Sequence
<220> FEATURE:

<223> OTHER INFORMATION: synthetic oligonucleotide

<400> SEQUENCE: 86
tcatgaatgt gcaggagcaa ctattaagg        29

<210> SEQ ID NO 87
<211> LENGTH: 28
<212> TYPE: DNA
<213> ORGANISM: Artificial Sequence
<220> FEATURE:
<223> OTHER INFORMATION: synthetic oligonucleotide

<400> SEQUENCE: 87
tcatgaatgt gcagggcaac tattaagg        28

<210> SEQ ID NO 88
<211> LENGTH: 17
<212> TYPE: DNA
<213> ORGANISM: Artificial Sequence
<220> FEATURE:
<223> OTHER INFORMATION: synthetic oligonucleotide

<400> SEQUENCE: 88
tcatgcaact attaagg        17

<210> SEQ ID NO 89
<211> LENGTH: 15
<212> TYPE: DNA
<213> ORGANISM: Artificial Sequence
<220> FEATURE:
<223> OTHER INFORMATION: synthetic oligonucleotide

<400> SEQUENCE: 89
tcatgaatgt gcagg        15

<210> SEQ ID NO 90
<211> LENGTH: 16
<212> TYPE: DNA
<213> ORGANISM: Artificial Sequence
<220> FEATURE:
<223> OTHER INFORMATION: synthetic oligonucleotide

<400> SEQUENCE: 90
tcatgaatgt gcagga        16

<210> SEQ ID NO 91
<211> LENGTH: 36
<212> TYPE: DNA
<213> ORGANISM: Nicotiana tabacum

<400> SEQUENCE: 91
ggatcggttc tataaggcta acagagcaca cacata        36

<210> SEQ ID NO 92
<211> LENGTH: 32
<212> TYPE: DNA
<213> ORGANISM: Artificial Sequence
<220> FEATURE:
<223> OTHER INFORMATION: synthetic oligonucleotide

<400> SEQUENCE: 92
ggatcggtta aggctaacag agcacacaca ta        32

<210> SEQ ID NO 93
<211> LENGTH: 29

```
<212> TYPE: DNA
<213> ORGANISM: Artificial Sequence
<220> FEATURE:
<223> OTHER INFORMATION: synthetic oligonucleotide

<400> SEQUENCE: 93
ggatataagg ctaacagagc acacacata                                      29

<210> SEQ ID NO 94
<211> LENGTH: 25
<212> TYPE: DNA
<213> ORGANISM: Artificial Sequence
<220> FEATURE:
<223> OTHER INFORMATION: synthetic oligonucleotide

<400> SEQUENCE: 94
ataaggctaa cagagcacac acata                                          25
```

GENE TARGETING IN PLANTS USING DNA VIRUSES

CROSS-REFERENCE TO RELATED APPLICATIONS

This application is a continuation of U.S. application Ser. No. 14/409,148, field Dec. 18, 2014, which is a National Stage Application under 35 U.S.C. § 371 and claims the benefit of International Application No. PCT/US2013/046495, filed Jun. 19, 2013, which claims benefit of priority from U.S. Provisional Application Ser. No. 61/790,581, filed on Mar. 15, 2013, U.S. Provisional Application Ser. No. 61/772,704, filed on Mar. 5, 2013, and U.S. Provisional Application No. 61/661,542, filed on Jun. 19, 2012, all of which are incorporated herein by reference in their entirety.

STATEMENT AS TO FEDERALLY SPONSORED RESEARCH

This invention was made with government support under DBI-0923827 awarded by the National Science Foundation. The government has certain rights in the invention.

TECHNICAL FIELD

This document relates to materials and methods for gene targeting in plants, and particularly to methods for gene targeting that include using geminiviruses and customizable endonucleases.

BACKGROUND

The precise modification of higher eukaryotic genomes, including plant genomes, is a highly sought after technology for basic research and biotechnology applications. Precise genome modification—referred to herein as gene targeting (GT)—relies on the DNA-repair machinery of the target cell, and on an exogenously supplied repair template (also referred to as a "donor sequence"). Through the activity of the homologous recombination (HR) pathway, homologous sequences carried by the repair template can recombine with a chromosomal target. Consequently, any modified sequence carried by the repair template will be stably integrated into the genome. Attempts to implement GT in plants often are plagued by extremely low HR frequencies. The majority of the time, donor DNA molecules integrate illegitimately via non-homologous end joining (NHEJ). This process occurs regardless of the size of the homologous "arms," as increasing the length of homology to approximately 22 kb results in no significant enhancement in GT (Thykjaer et al., *Plant Mol. Biol.*, 35:523-530, 1997).

Other studies have aimed at increasing the efficiency of GT in plants. Some methods are based on the use of customizable endonucleases, such as zinc finger nucleases (ZFNs), meganucleases (MNs), and transcription activator-like (TAL) effector nucleases (TALE nucleases). A targeted DNA double-strand break (DSB) can stimulate recombination by a factor of 100 between transforming T-DNA and a native chromosomal locus (Puchta et al., *Proc. Natl. Acad. Sci. USA*, 93:5055-5060, 1996). Through the coordinated delivery of a repair template and a customizable endonuclease, high-frequency GT may be achieved in plants (Townsend et al., *Nature*, 459:442-445, 2009). Such methods are designed for use in protoplasts, which enables direct delivery of repair templates and nuclease-expressing plasmids to individual cells though PEG transformation or electroporation. However, the ability to practice GT is limited to labs with the expertise and equipment for tissue culturing and plant regeneration.

SUMMARY

Gene targeting in plant cells has been performed primarily by two techniques: (1) direct transfer of DNA into plant cells by either electroporation/PEG transformation of protoplasts, or by biolistic bombardment of DNA into various plant tissues; and (2) by *Agrobacterium*-mediated transformation. In these methods, the exogenously supplied DNA is either T-DNA, PCR-derived, or plasmid-derived.

This document is based in part on the development of a novel and effective in planta method for gene targeting that combines the use of geminiviral-based gene targeting vectors and a targeted DNA double strand break engineered by a co-delivered endonuclease. This is the first account demonstrating concurrent use of these techniques as a gene targeting methodology, which is likely to have vast implications in all areas of plant biology. For example, this technology can be used to accelerate the rate of functional genetic studies in plants. The technology also can be used to engineer plants with improved characteristics, including enhanced nutritional quality, increased resistance to disease and stress, and heightened production of commercially valuable compounds.

There are several benefits to using geminiviruses and endonucleases for gene targeting in plants, including (i) the ability of the virus to stably propagate the gene targeting vector from cell-to-cell within the plant, (ii) the ability of the virus to replicate the gene targeting vector to high copy numbers within plant cell nuclei (on average 1000 copies per cell, but numbers can reach up to 30,000), and (iii) the circular nature of the geminivirus genome, as circular DNA is thought to participate less frequently in illegitimate recombination. These properties contribute to an effective, reliable and reproducible procedure for gene targeting in plant cells.

The methods provided herein enable practitioners to achieve high frequency gene targeting by creating a chromosome break in a target locus while simultaneously using the viral replication machinery to make repair templates to achieve gene targeting. The viral repair templates can be generated either by infecting plants with engineered viruses or by using deconstructed viral vectors. The latter vectors replicate viral DNA and thereby produce the repair template, but they do not generate a productive infection.

In a first aspect, this disclosure features a method for modifying the genetic material of a plant cell. The method can include (a) introducing into the cell a virus nucleic acid comprising a repair template that is heterologous to the virus and is targeted to a first sequence that is endogenous to the plant cell; and (b) inducing a double strand break at or near the sequence to which the repair template is targeted, wherein said double strand break is generated by an endonuclease targeted to a second endogenous plant sequence at or near the first sequence that is targeted by the repair template, wherein homologous recombination occurs between the first endogenous plant sequence and the repair template.

The virus nucleic acid can be a plant DNA virus nucleic acid. The virus nucleic acid can be a geminivirus nucleic acid. The endonuclease can be a zinc finger nuclease, a transcription activator-like effector nuclease, a meganuclease, or a CRISPR/Cas system endonuclease. The endonuclease can be encoded by a transgene sequence stably integrated into the genetic material of the plant, or can be expressed transiently. When the endonuclease is encoded by a transgene, the transgene can be operably linked to a promoter that is constitutive, cell specific, inducible, or activated by alternative splicing of a suicide exon. The virus nucleic acid can include a sequence encoding the endonuclease. The method can further include introducing into the plant cell an RNA virus nucleic acid comprising a nucleotide sequence encoding the endonuclease. The RNA virus nucleic acid can be introduced into the plant cell after or simultaneous with step (a). The RNA virus nucleic acid can be from a tobacco rattle virus, a potato virus X, a pea early browning virus, or a barley stripe mosaic virus. The plant can be a monocotyledonous plant (e.g., wheat, maize, a grass such as purple false brome (*Brachypodium distachyon*), *Haynaldia villosa*, or *Setaria*), or a dicotyledonous plant (e.g., tomato, soybean, tobacco, potato, or *Arabidopsis*).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
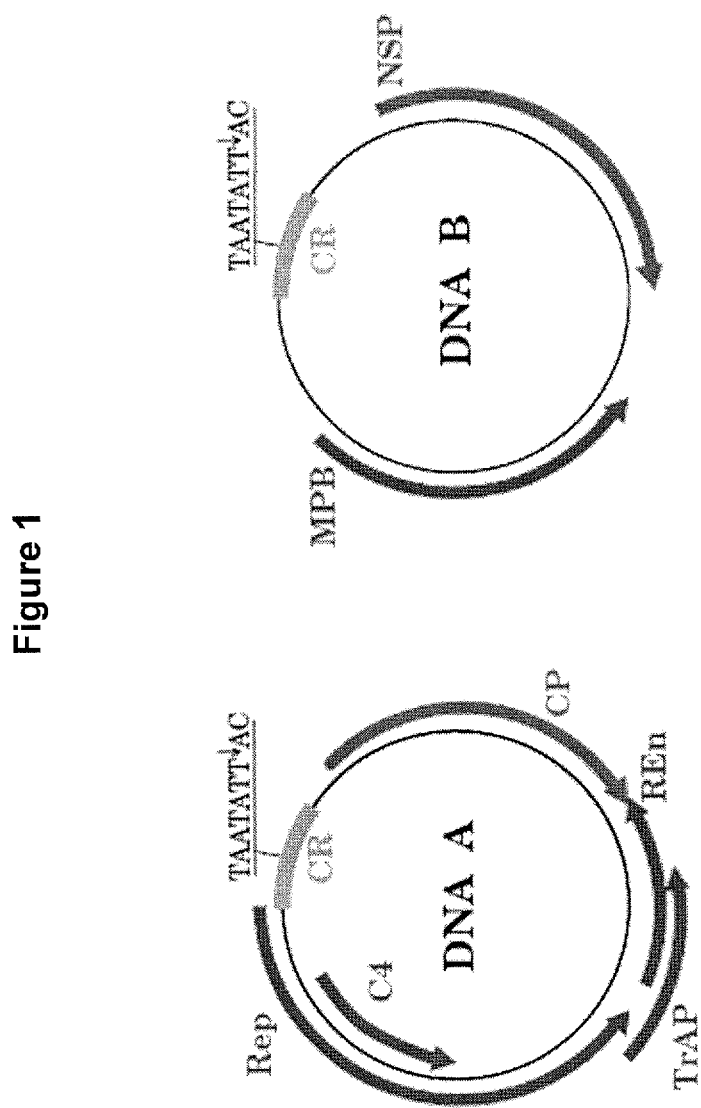
FIG. 1 is an illustration of the cabbage leaf curl virus (CaLCuV) genome. CaLCuV contains a bipartite genome, with the DNA A component encoding proteins necessary for viral replication and encapsidation, and the DNA B component encoding proteins necessary for cell-to-cell movement. The coat protein nucleotide sequence (CP) can be replaced by up to 800 nucleotides of repair template DNA sequence. See, Gutierrez, *Physiol. Mol. Plant Pathol.* 6060:219-230, 2002.

This document provides a highly efficient, virus-based system and methods for targeted modification of plant genomes. The in planta system and methods for GT include the use of customizable endonucleases in combination with plant DNA viruses. Plant DNA viruses, including geminiviruses, have many attributes that may be advantageous for in planta GT, including their ability to replicate to high copy numbers in plant cell nuclei. Importantly, these viruses can be modified to encode a desired nucleotide sequence, such as a repair template sequence targeted to a particular sequence in a plant genome. First generation geminiviruses, or "full viruses" (viruses that retain only the useful "blocks" of sequence), can carry up to about 800 nucleotides (nt), while deconstructed geminiviruses (viruses that encode only the proteins needed for viral replication) have a much larger cargo capacity. This document describes how customizable nucleases and plant DNA viruses enable in planta GT, and provides materials and methods for achieving such GT. The methods can be used with both monocotyledonous plants (e.g., banana, grasses (e.g., *Brachypodium distachyon*), wheat, oats, barley, maize, *Haynaldia villosa*, palms, orchids, onions, pineapple, rice, and sorghum) and dicotyledonous plants (e.g., *Arabidopsis*, beans, *Brassica*, carnations, chrysanthemums, citrus plants, coffee, cotton, *eucalyptus*, *impatiens*, melons, peas, peppers, *Petunia*, poplars, potatoes, roses, soybeans, squash, strawberry, sugar beets, tobacco, tomatoes, and woody tree species).

In general, the system and methods described herein include two components: a plant DNA virus (e.g., geminivirus) vector containing a repair template targeted to an endogenous plant sequence, and an endonuclease that also is targeted to a site near or within the target sequence. The endonuclease can be activated to create targeted DNA double-strand breaks at the desired locus, and the plant cell can repair the double-strand break using the repair template present in the geminivirus, thereby incorporating the modification stably into the plant genome.

Geminiviruses are a large family of plant viruses that contain circular, single-stranded DNA genomes. Examples of geminiviruses include the cabbage leaf curl virus, tomato golden mosaic virus, bean yellow dwarf virus, African cassava mosaic virus, wheat dwarf virus, *miscanthus* streak mastrevirus, tobacco yellow dwarf virus, tomato yellow leaf curl virus, bean golden mosaic virus, beet curly top virus, maize streak virus, and tomato pseudo-curly top virus. As described herein, geminivirus sequences can be used as gene targeting vectors. For example, the geminivirus genome can be engineered to contain a desired modification flanked by sequences of homology to a target locus. In some cases, this can be accomplished by replacing non-essential geminivirus nucleotide sequence (e.g., CP sequence) with a desired repair template. Other methods for adding sequence to viral vectors include, without limitation, those discussed in Peretz et al. (*Plant Physiol.*, 145:1251-1263, 2007).

The repair template contains homology to a particular sequence within the genome of a plant. Typically, a repair template includes a nucleic acid that will replace an endogenous target sequence within the plant, flanked by sequences homologous to endogenous sequences on either side of the target. When a non-essential (e.g., CP) sequence within a geminivirus vector is replaced with a repair template, the repair template can have a length up to about 800 nt (e.g., 100 nt, 200 nt, 300 nt, 400 nt, 500 nt, 600 nt, 700 nt, 800 nt, or any length between about 100 nt and about 800 nt). Within the repair template, the flanking homologous sequences can have any suitable length (e.g., about 25 nt, 50 nt, 75 nt, 100 nt, 150 nt, 200 nt, 250 nt, 300 nt, 350 nt, 400 nt, or any length between about 25 nt and about 400 nt). Repair templates and DNA virus plasmids can be prepared using techniques that are standard in the art, including those described below.

The second component of the system and methods described herein is an endonuclease that can be customized to target a particular nucleotide sequence and generate a double strand break at or near that sequence. Examples of such customizable endonucleases include ZFNs, MNs, and TALE nucleases, as well as Clustered Regularly Interspersed Short Palindromic Repeats/CRISPR-associated (CRISPR/Cas) systems. See, for example, Sander et al., *Nature Methods*, 8:67-69, 2011; Jacoby et al., *Nucl. Acids Res.*, 10.1093/ nar/gkr1303, 2012); Christian et al., *Genetics,* 186:757-761, 2010; U.S. Publication No. 2011/0145940; Cong et al., *Science* 339:819-823, 2013; and Mali et al., *Science* 339: 823-826, 2013, for a discussion of each. In particular, CRISPR/Cas molecules are components of a prokaryotic adaptive immune system that is functionally analogous to eukaryotic RNA interference, using RNA base pairing to direct DNA or RNA cleavage. Directing DNA DSBs requires two components: the Cas9 protein, which functions as an endonuclease, and CRISPR RNA (crRNA) and tracer RNA (tracrRNA) sequences that aid in directing the Cas9/ RNA complex to target DNA sequence (Makarova et al., *Nat Rev Microbiol,* 9(6):467-477, 2011). The modification of a single targeting RNA can be sufficient to alter the nucleotide target of a Cas protein. In some cases, crRNA and tracrRNA can be engineered as a single cr/tracrRNA hybrid to direct Cas9 cleavage activity (Jinek et al., *Science,* 337(6096):816-821, 2012). Like TALE nucleases, for example, the components of a CRISPR/Cas system (the Cas9 endonuclease and the crRNA and tracrRNA, or the cr/tracrRNA hybrid) can be delivered to a cell in a geminivirus construct.

Figure 2:
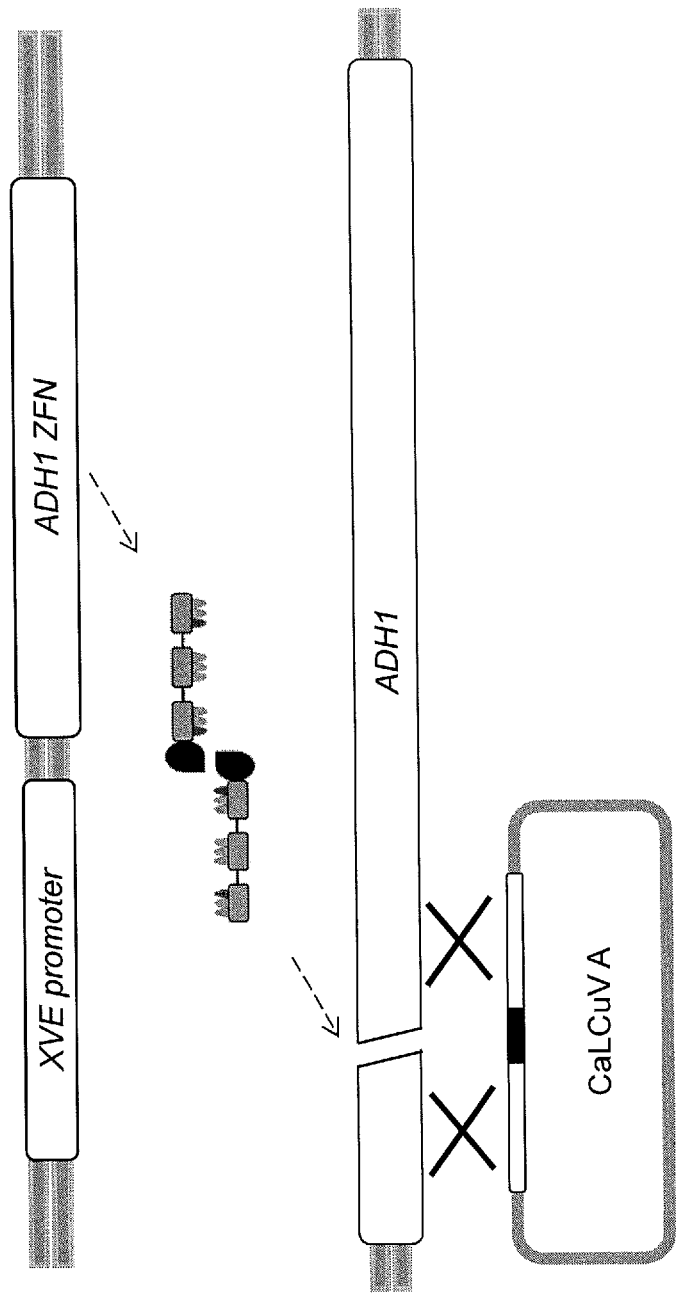
FIG. 2 is a schematic of an experimental approach for gene targeting using engineered geminiviruses and transgenic *Arabidopsis* plants encoding a stably integrated zinc finger nuclease (ZFN) transgene. Repair of the ZFN-induced DSB using a repair template on the CaLCuV A genome results in the stable incorporation of a unique 18 bp sequence into the ADH1 gene.

In some embodiments of the systems and methods provided herein, the sequence encoding the endonuclease can be stably integrated into the plant genome that will be also infected with a geminivirus containing a repair template. See, for example, FIG. 2, which depicts a plant genome into which a sequence encoding an ADH1 targeted ZFN has been stably integrated. The coding sequence can be operably linked to a promoter that is inducible, constitutive, cell specific, or activated by alternative splicing of a suicide exon. For example, as shown in FIG. 2, the ADH1 ZFN coding sequence is operably linked to an XVE promoter, which can be activated by estradiol. The plant can be infected with a geminivirus containing a repair template (indicated by the black bar flanked by white bars in the "CaLCuV"), and expression of the ZFN can be activated by treating the plant with estradiol. The ZFN protein then can cleave the DNA at the target sequence, facilitating HR on either side of the repair template to be integrated.

Alternatively, the endonuclease coding sequence can be contained in the same geminivirus construct as the repair template, or can be present in a second plasmid that is separately delivered to the plant, either sequentially or simultaneously with the geminivirus construct. For example, in some embodiments, plants can be transfected or infected with a second viral vector, such as an RNA virus vector (e.g., a tobacco rattle virus (TRV) vector, a potato virus X vector, a pea early browning virus vector, or a barley stripe mosaic virus vector) that encodes the endonuclease. As an example, TRV is a bipartite RNA plant virus that can be used to transiently deliver protein coding sequences to plant cells. For example, the TRV genome can be modified to encode a ZFN or TALE nuclease by replacing TRV nucleotide sequence with a subgenomic promoter and the ORF for the endonuclease. The inclusion of a TRV vector can be useful because TRV infects dividing cells and therefore can modify germ line cells specifically. In such cases, expression of the endonuclease encoded by the TRV can occur in germ line cells, such that HR at the target site is heritable.

In embodiments in which a geminivirus vector contains both a repair template and an endonuclease encoding sequence, it is noted that that the geminivirus can be deconstructed such that it encodes only the proteins needed for viral replication. Since a deconstructed geminivirus vector has a much larger capacity for carrying sequences that are heterologous to the virus, it is noted that the repair template may be longer than 800 nt. An exemplary system using a deconstructed vector is described in the Example below.

The construct(s) containing the repair template and, in some cases, the endonuclease encoding sequence, can be delivered to a plant cell using, for example, biolistic bombardment. Alternatively, the repair template and endonuclease sequences can be delivered using *Agrobacterium*-mediated transformation, insect vectors, grafting, or DNA abrasion, according to methods that are standard in the art, including those described herein.

Figure 3:
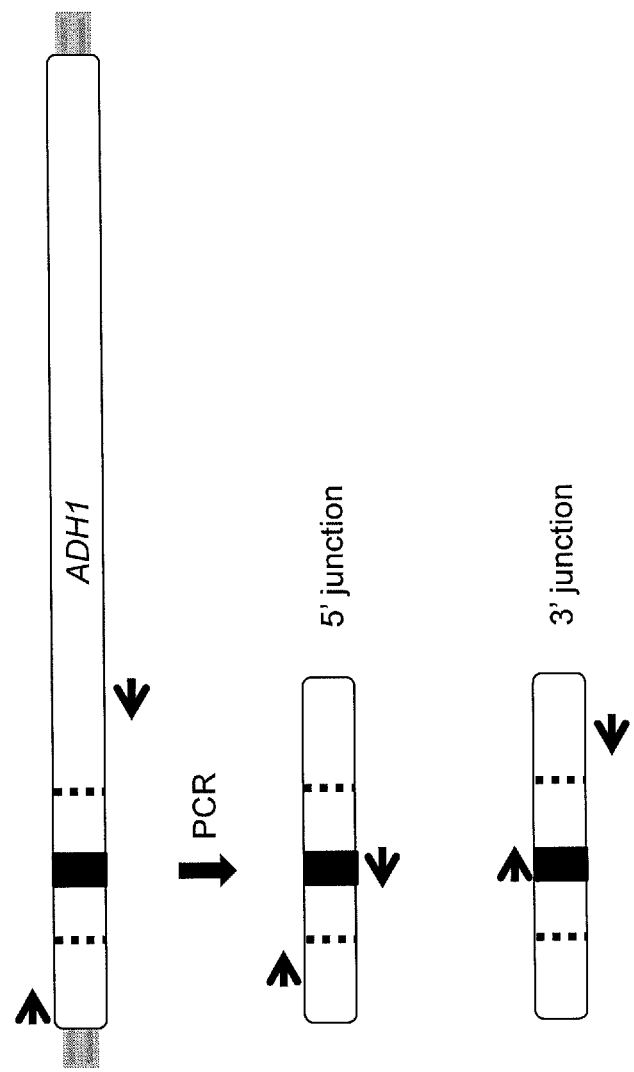
FIG. 3 is an illustration of a nested PCR method that can be used to detect gene-targeted ADH1 alleles. Genomic DNA from somatic *Arabidopsis* cells—exposed to estradiol and infected with CaLCuV—is used as a template for PCR amplification of the ADH1 locus. Amplicons are gel purified and used as templates for a second PCR, with one primer specific for the GT modification. Dashed lines represent the outer limit of homology carried by the repair template.

After a plant is infected or transfected with a repair template (and, in some cases, an endonuclease encoding sequence), any suitable method can be used to determine whether GT has occurred at the target site. In some embodiments, a phenotypic change can indicate that a repair template sequence has been integrated into the target site. Such is the case for the gus::nptII plants that were repaired with a geminivirus containing a GUS sequence, as described below. PCR-based methods also can be used to ascertain whether a genomic target site contains a repair template sequence, and/or whether precise recombination has occurred at the 5' and 3' ends of the repair template. A schematic depicting an example of such a technique is provided in FIG. 3, and the work described below also demonstrates GT in *Arabidopsis* using PCR-based techniques. In some of these experiments, plants expressing a ZFN were infected with geminiviruses producing repair templates (also referred to herein as donor molecules), and recombination between the repair template and the target gene on the plant chromosome was observed in somatic cell genomic DNA from infected plants expressing an active endonuclease. In particular, following systemic infection of an engineered geminivirus containing a unique 18 bp modification flanked by 400 bases of homology to the ADH1 target locus, ZFN expression was induced. Following ZFN expression, genomic DNA from somatic cells was extracted and assessed for GT events. Results from the enrichment PCR suggested successful GT of the ADH1 loci using geminiviruses and ZFNs. Additional experiments are described that involve quantifying the frequency of gene targeting in somatic cells, and demonstrating gene targeting by phenotypic analysis.

The invention will be further described in the following examples, which do not limit the scope of the invention described in the claims.

Examples

Cloning of Genetic Elements into pCPCbLCVA.007

The cabbage leaf curl virus (CaLCuV) is a bipartite, circular single-stranded DNA virus that can infect *Arabidopsis* plants when delivered by microprojectile bombardment. Initiating viral infection requires the delivery of two plasmids containing sequence for both genomes (A and B components; FIG. 1). The viral sequences are partially duplicated, containing two direct repeats of the origin of replication flanking the viral genome. Consequently, delivery of these plasmids to plant cell nuclei results in replicational release of full-length, circular geminivirus genomes.

To construct CaLCuV A components encoding repair template sequence, the coat protein (AR-1) coding sequence was replaced with desired sequence. AR-1 is required for insect-transmission of the virus, but it is not required for viral amplification and systemic spreading. Because of this, approximately 800 nucleotides can be added to the A component genome without preventing its ability to infect.

Figure 4A:
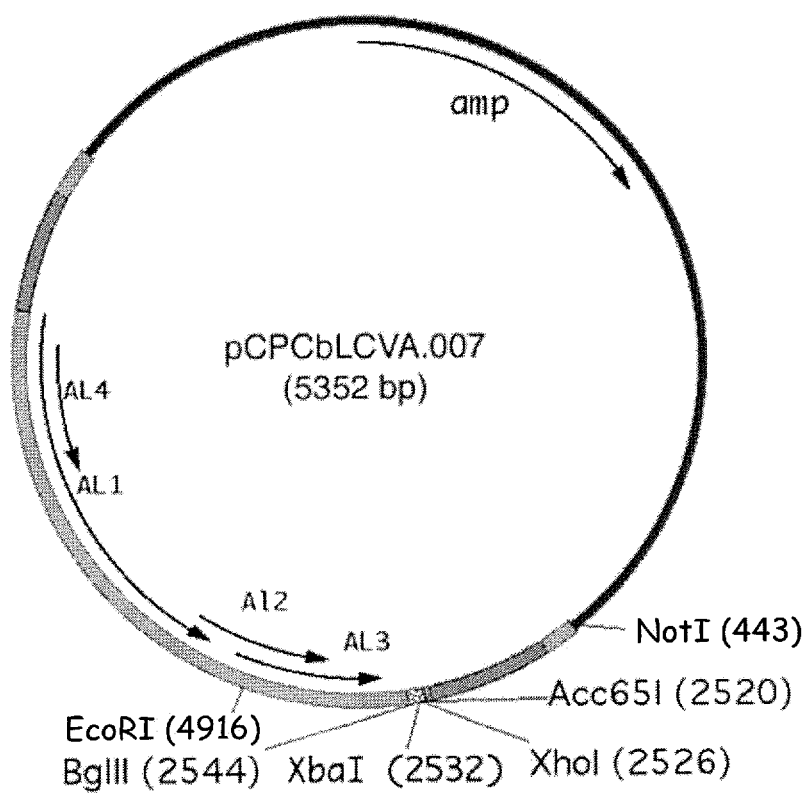
FIG. 4A is a diagram of pCPCbLCVA.007, which contains the entire genome of the CaLCuV A component flanked by direct repeats of the common region for viral excision from the plasmid. To modify pCPCbLVCA.007 for carrying gene fragments, the coding region of the coat protein gene, AR1, was replaced with a polylinker. The AR1 promoter, the translational start (ATG) and the putative polyadenylation sites are retained. To initiate infection, this plasmid is co-transformed with pCPCbLCVB.002. Virus derived from these vectors moves from cell-to-cell within *Arabidopsis* plants but, without the coat protein gene, it is not transmissible.
Figure 4B:
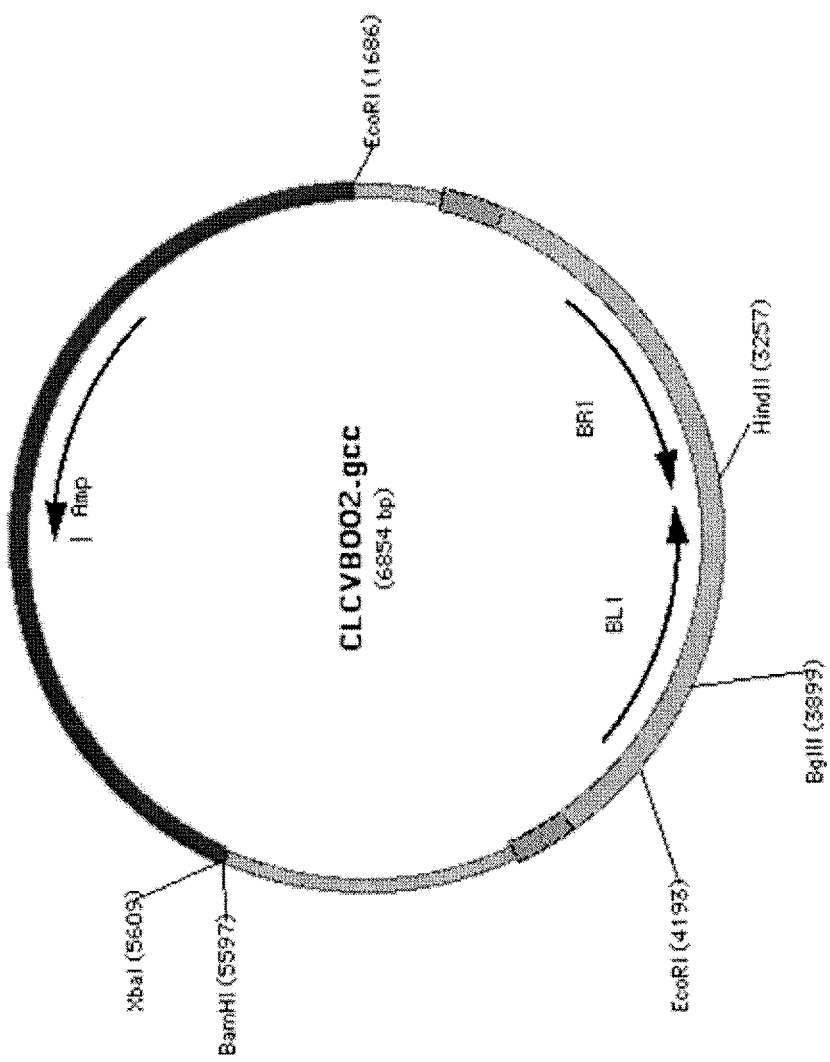
FIG. 4B is a diagram of pCPCbLCVB.002, which contains the entire genome of the CaLCuV B component flanked by direct repeats of the common region for viral excision from the plasmid. Bombardment of the B component alone can be used as a negative control for DNA contamination (no virus should be replicated). See, Muangsan and Robertson, *Meth. Mol. Biol.* 265:101-15, 2004.

Viral vectors encoding repair templates targeting the ADH1 and gus::nptII loci use the pCPCbLCVA.007 backbone. pCPCbLCVA.007 is a plasmid initially designed for viral induced gene silencing (VIGS). It encodes a partially duplicated A component with the AR-1 nucleotide sequence replaced with a multicloning site (MCS). Co-bombardment of *Arabidopsis* plants with pCPCbLCVA.007 (FIG. 4A) and pCPCbLCVB.002 (FIG. 4B) (encoding a partially duplicated B genome) results in a high-frequency of successful infection (75-100%).

Constructing First Generation Viral Vectors with Repair Templates Targeting ADH1

An ADH1-targeting repair template was constructed for ligation into pCPCbLCVA.007. The template for amplifying the ADH1 repair template was genomic DNA from *Arabidopsis thaliana* (ecotype Columbia). To isolate genomic DNA, about 100 mg of leaf tissue was frozen in liquid nitrogen and ground to a fine powder. 500 µl of CTAB buffer (2.0 g hexadecyl trimethyl-ammonium bromide (CTAB)), 10 mL 1M tris pH 8.0, 4 mL 0.5M ethylenediaminetetraacetic acid di-sodium salt (EDTA), 28 mL 5M NaCl, 40 mL dH$_2$O, pH adjusted to 5.0 per 100 mL of solution) was added and the samples were incubated at 65° C. for 20 min. Samples were centrifuged for 5 minutes at 12,000 RPM and the supernatant was transferred to a clean microfuge tube. 500 µl of chloroform was added and the samples were inverted for 5 minutes at room temperature. Samples were centrifuged for 1 minute at 12,000 RPM and the supernatant was transferred to a clean microfuge tube. 800 µl of ice-cold 100% ethanol was added and the samples were centrifuged for 1 minute at 15,000 RPM. The supernatant was decanted and the genomic DNA pellet was washed once in 75% ethanol. Samples were centrifuged for 30 seconds at 13,000 RPM and the supernatant was completely removed. Last, the genomic DNA was resuspended in 50 µl of dH$_2$O. Repair templates targeting ADH1 were designed to encode a unique 18 bp modification sequence (5'-GAGCTCAGTACTGC ATGC-3'; SEQ ID NO:1) flanked by arms of homology to the ADH1-ZFN target site. Several repair templates were constructed with varying lengths of homology for each arm. In total, four repair templates were made with 491, 391, 291, or 191 nucleotides of homology in each arm. Notably, the modification was designed to remove the native ZFN binding site, which prevents cleavage of the repair template before and after GT. To generate ADH1 repair templates for cloning into pCPCbLCVA.007, left and right homology sequences were amplified from *Arabidopsis* genomic DNA using primers NB177+NB128 and NB178+NB129 for 491 bp homology arms, NB104+NB128 and NB112+NB129 for 391 bp homology arms, NB105+NB207 and NB113+NB208 for 291 bp homology arms, and NB106+NB207 and NB114+NB208 for 191 bp homology arms, respectively. Primer sequences are provided in Table 1. Importantly, the reverse primers for the left homology arm and the forward primers for the right homology arm contained complementary 18 bp linkers encoding the modification sequence. Also, the forward primers for the left homology arm and the reverse primer for the right homology arm contained linkers encoding XbaI and BglII restriction enzyme sites, respectively. PCR reactions were performed in a 25 µl PCR mix composed of 2.5 µl of 10×NEB Standard Taq buffer, 0.5 µl of 10 mM dNTPs, 0.5 µl of 10 µM primer 1, 0.5 µl of 10 µM primer 2, 18.8 µl of dH$_2$O, 0.2 µl of Taq polymerase, and 2 µl of genomic DNA (~200 ng). The PCR conditions were 5 minutes at 94° C. followed by 30 cycles of 30 seconds at 94° C., 30 seconds at 55° C., and 1 minute at 72° C. The resulting amplicons were resolved by agarose electrophoresis using a 1% gel. DNA bands of expected sizes were excised from the agarose gel and purified using the QIAquick Gel Extraction Kit (Qiagen) following manufacturer's protocols. Purified DNA fragments containing the left and right homology arms were then fused together in an overlap-extension PCR (OE-PCR). Fusion reactions were performed in a 24 µl PCR mix composed of 2.5 µl of 10× cloned Pfu buffer, 0.5 µl of 10 mM dNTPs, 14.5 µl of dH$_2$O, 0.5 µl of Pfu enzyme, and 3 µl each of the purified amplicons. Fusion conditions were 5 minutes at 94° C. followed by 10 cycles of 30 seconds at 94° C., 30 seconds at 50° C., and 1 minute at 72° C. Following the fusion PCR, 0.5 µl of 10 µM primer 1 and 0.5 µl of 10 µM primer 2 were added and the samples were run in another PCR. The PCR conditions were 5 minutes at 94° C. followed by 30 cycles of 30 seconds at 94° C., 30 seconds at 56° C., and 1 minute at 72° C. Following OE-PCR, 10 µl of the PCR solution and 1 µg of pCPCbLCVA.007 were digested with XbaI and BglII following standard procedures. The resulting digested amplicons and vector were resolved by agarose electrophoresis using a 1% gel. DNA bands of expected sizes were excised from the agarose gel and purified and ligated together in a 10 µl reaction using T4 DNA ligase (New England Biolabs) following the manufacturer's procedures. DH5a *E. coli* were transformed with 2 µl of the ligation mix following standard procedures and plated onto LB media containing 50 µg/ml of carbenicillin. DNA sequences of resulting clones were confirmed by sequencing to encode the expected repair template. These vectors are henceforth referred to as CaLCuVA.ADH1-1000, CaLCuVA.ADH1-800, CaLCuVA.ADH1-600, and CaLCuVA.ADH1-400.

Constructing First Generation Viral Vectors with Repair Templates Targeting gus::nptII The following describes methods for constructing GUS-FIX repair templates for ligation into pCPCbLCVA.007. The chromosomal target for the repair template is a GUS transgene with ~300 bp of nucleotide sequence removed from the 3' end and replaced with a Zif268 target site. GUS-FIX repair templates were designed to contain flanking arms of homology to the target locus (200 bp each) and a 300 bp modification sequence. As a consequence of GT, the coding sequence of GUS is restored. Cells actively expressing GUS can be phenotypically detected by an enzymatic assay. To generate GUS-FIX repair templates for cloning into pCPCbLCVA.007, the left homology arm (also containing the 300 bp of GUS-FIX sequence) and the right homology arm were amplified from pDW1269 plasmid DNA using primers NB274+NB271 and NB272+NB275, respectively. Importantly, the left and right homology arms contained complementary sequences to enable their fusion in OE-PCR. PCR reactions to generate the fragments were performed in a 25 µl mix composed of 2.5 µl of 10×NEB Standard Taq buffer, 0.5 µl of 10 mM dNTPs, 0.5 µl of 10 µM primer 1, 0.5 µl of 10 µM primer 2, 18.8 µl of dH$_2$O, 0.2 µl of Taq polymerase, and 2 µl of genomic DNA (~200 ng). The PCR conditions were 5 minutes at 94° C. followed by 30 cycles of 30 seconds at 94° C., 30 seconds at 55° C., and 1 minute at 72° C. The resulting amplicons were resolved by agarose electrophoresis using a 1% gel. DNA bands of expected sizes were purified and ligated together in an OE-PCR. Fusion reactions were performed in a 24 µl mix composed of 2.5 µl of 10× cloned Pfu buffer, 0.5 µl of 10 mM dNTPs, 14.5 µl of dH$_2$O, 0.5 µl of Pfu enzyme, and 3 µl each of the purified amplicons. Fusion conditions were 5 minutes at 94° C. followed by 10 cycles of 30 seconds at 94° C., 30 seconds at 50° C., and 1 minute at 72° C. Next, 0.5 µl of 10 µM primer NB274 and 0.5 µl of 10 µM primer NB275 were directly added to the fusion reactions and immediately run in another PCR. The PCR conditions were 5 minutes at 94° C. followed by 30 cycles of 30 seconds at 94° C., 30 seconds at 56° C., and 1 minute at 72° C. Following OE-PCR, 10 µl of solution and 1 µg of pCPCbLCVA.007 were digested with XbaI and Bg/II following standard procedures. The resulting digested amplicons and vector were resolved by agarose electrophoresis using a 1% gel. DNA bands of expected sizes were purified and ligated in a 10 µl reaction using T4 DNA ligase. DH5a *E. coli* were transformed with 2 µl of the ligation mix following standard procedures, and plated onto LB media containing 50 µg/ml of carbenicillin. The DNA sequence of a resulting clone was confirmed to encode the GUS-FIX repair template sequence. This vector is referred to as CaLCuVA.GUS-FIX.

Growing *Arabidopsis* Plants

To prepare *Arabidopsis* plants for biolistic bombardment, 500-1,000 *Arabidopsis* seeds (10-20 mg) were stratified in 0.1% agarose for 3 days at 4° C. Seeds were dispensed onto the surface of BM2 soil (J.R. Johnson Supply; Minneapolis, Minn.) in each of the four corners of 2.5×2.5 inch pots. Pots were placed in a plastic flat and 1 L of 10-20-10 Peters Professional (Scotts) fertilizer solution was added. Flats were covered with a clear plastic dome and moved to a growth chamber under 12 h light/12 h dark conditions. Plants were grown at 22-24° C. for 2 weeks before removing the dome, and then grown for an additional 1-2 weeks with watering when needed. Watering was stopped approximately 7 days before bombardment. Plants were bombarded when they reached the five- to six-leaf-stage (approximately four weeks).

Infecting *Arabidopsis* Plants by Biolistic Bombardment

Biolistic bombardment was carried out closely following the protocol described by Muangsan et al., *Meth. Mol. Biol.*, 265:101-115, 2004. Briefly, to prepare microprojectile particles for five bombardments, 5 µg of each plasmid (CaL-CuVA and CaLCuVB) was added to a tube containing 50 µl of 60 mg/mL gold beads and briefly vortexed. 50 µl of 2.5 M $CaCl_2$ was directly added to the samples and immediately pipetted in and out of a tip to break up conglomerates. 20 µl of 0.1 M spermidine was added and the samples were immediately vortexed for 5 min. The samples were centrifuged at 10,000 RPM for 10 seconds and the supernatant was removed. The gold-bead pellet was resuspended in 250 µl of 100% ethanol and then centrifuged at 10,000 rpm for 10 sec. Supernatants were removed and the samples were resuspended in 65 µl of 100% ethanol. The particles were then stored on ice until bombardment. To prepare the assembly for the microprojectile particles, macrocarrier holders and macrocarriers were soaked in 95% ethanol, air-dried, and assembled. 10 µl of resuspended particles were then spotted onto the center of the macrocarrier and allowed to air-dry.

Biolistic bombardment was carried out in a horizontal laminar flow hood using a PDS-1000 He system (Bio-Rad). To prepare the PDS-1000 He system, a non-sterile rupture disk (1100 psi) was dipped in 100% isopropanol and placed into the upper assembly. The macrocarrier launch assembly (MCLA) was then prepared by dipping a metal stopping screen in 95% ethanol, and then placing the dried screen onto the opening of the lower assembly. The macrocarrier and macrocarrier holder were inverted and placed above the stopping screen. The retaining ring was screwed in, and the MCLA was placed into the top rack of the chamber. A single pot containing four plants was then placed in the chamber directly beneath the MCLA. A vacuum of 28 in was created, and helium was added to the upper chamber until the rupture disk burst. Bombarded plants were then removed from the chamber and returned to a covered flat. Between bombardments of different constructs, the chamber was cleaned with 70% ethanol. This procedure was repeated for additional infections. By following these methods, infection was successfully initiated in majority of the bombarded plants (75-100%).

Growing Infected *Arabidopsis* Plants

Immediately after bombardment, infected *Arabidopsis* plants were placed in a flat with approximately 1 L of fertilizer solution and moved back to the growth chamber. A clear plastic dome was used to cover the plants for seven days post infection. Infection was noticeable 8-10 dpi by curling of rosette leaves. At 14 dpi, plants containing an XVE ADH1-ZFN transgene were induced by exposure to β-estradiol (Sigma E2758) by spraying and watering. The spray contained 0.01% Silwet L-77 (Vac-In-Stuff) and 20 µM β-estradiol, while the water contained only 20 µM β-estradiol. Induction was carried out by continuously spraying (approximately once a day) and watering (approximately twice a week) for 10-14 days.

Isolating genomic DNA from infected *Arabidopsis* plants

About two weeks after induction, genomic DNA was extracted from somatic plant tissue. A single rosette leaf and cauline leaf were collected from each infected plant. Care was taken when choosing leaves in order to minimize the likelihood of detecting recombination between plasmid molecules and genomic DNA. Criteria for choosing rosette leaves were 1) healthy leaf tissue with no obvious necrotic lesions, and 2) leaves growing on the periphery of the pot—away from damage caused by biolistic bombardment. Plant genomic DNA was extracted following the CTAB procedure as described above.

Assessing β-Estradiol Induction of the ADH1-ZFN Transgene

To determine if induction of nuclease expression by β-estradiol was successful, enrichment PCR was performed on purified genomic DNA. Enrichment PCR is designed to detect ZFN-induced NHEJ mutations at the ADH1 target locus—an indirect assay for verifying nuclease activity. This procedure relies on a restriction enzyme site positioned in or near the target site spacer sequence. In essence, if the nuclease is not active, then target site amplicons will be completely digested by the restriction enzyme. On the other hand, if the nuclease is active there will be a population of target site amplicons with destroyed restriction enzymes sites that will not be digested by the restriction enzyme. Thus, detection of a digestion-resistant band suggests that the nuclease was actively creating DSBs.

Figure 5:
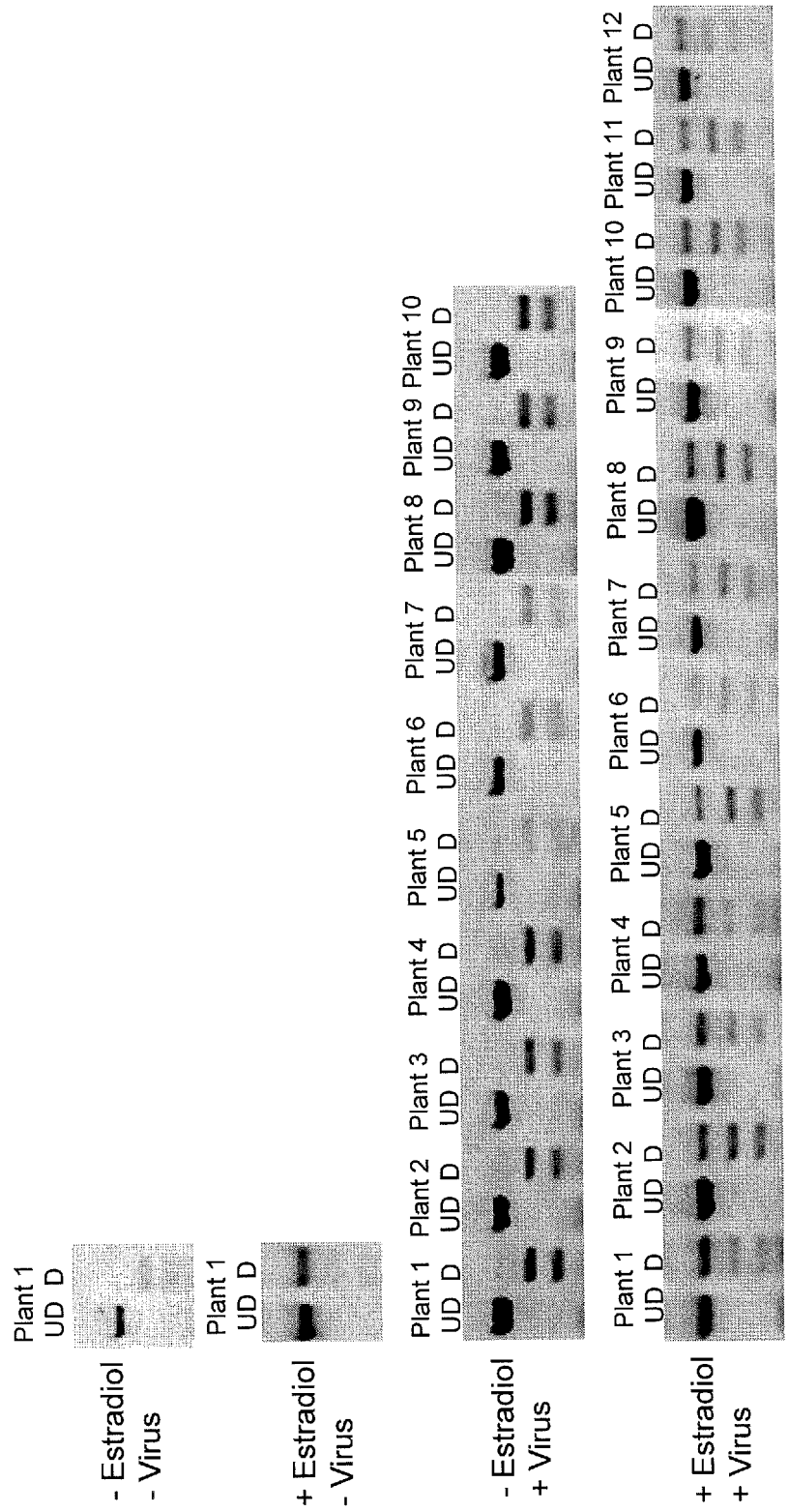
FIG. 5 is a picture of gels with amplicons generated from an enrichment PCR designed to detect ZFN-induced mutations at the ADH1 gene after induction by β-estradiol. DNA was assessed for NHEJ mutations from (i) non-induced and non-infected plants (−Estradiol, −Virus), (ii) induced and non-infected plants (+Estradiol, −Virus), (iii) non-induced and infected plants (−Estradiol, +Virus), and (iv) induced and infected plants (+Estradiol, +Virus). D, digested; UD, undigested.

For these assays, 1 µg of genomic DNA from induced and non-induced plants was digested with BstXI (NEB) in a 10 µl solution following standard procedures. Immediately following digestion, 2 µl of the solution was used as a template for PCR in a reaction containing of 2.5 µl of 10×NEB Standard Taq buffer, 0.5 µl of 10 mM dNTPs, 0.5 µl of 10 µM primer NB161, 0.5 µl of 10 µM primer NB154, 18.8 µl of $dH_2O$, 0.2 µl of Taq polymerase, and 2 µl of the digested solution (~200 ng genomic DNA). The PCR conditions were 5 minutes at 94° C. followed by 35 cycles of 30 seconds at 94° C., 30 seconds at 55° C., and 1 minute at 72° C. 10 µl of the PCR reaction was then digested with BstXI. The entire digested sample and the corresponding PCR sample were loaded side-by-side onto a 1.2% agarose gel. In general, plants that were not exposed to estradiol had very faint, or undetectable, digestion-resistant amplicons (FIG. 5, bottom row, digested ("D") lanes). Conversely, plants exposed to β-estradiol had much stronger resistant bands (FIG. 5, top row, digested ("D") lanes). From these data, it was concluded that the timing of ADH1-targeted DSBs was controlled by β-estradiol.

Assessing Repair Template Stability in Infected Plants

Figure 6:
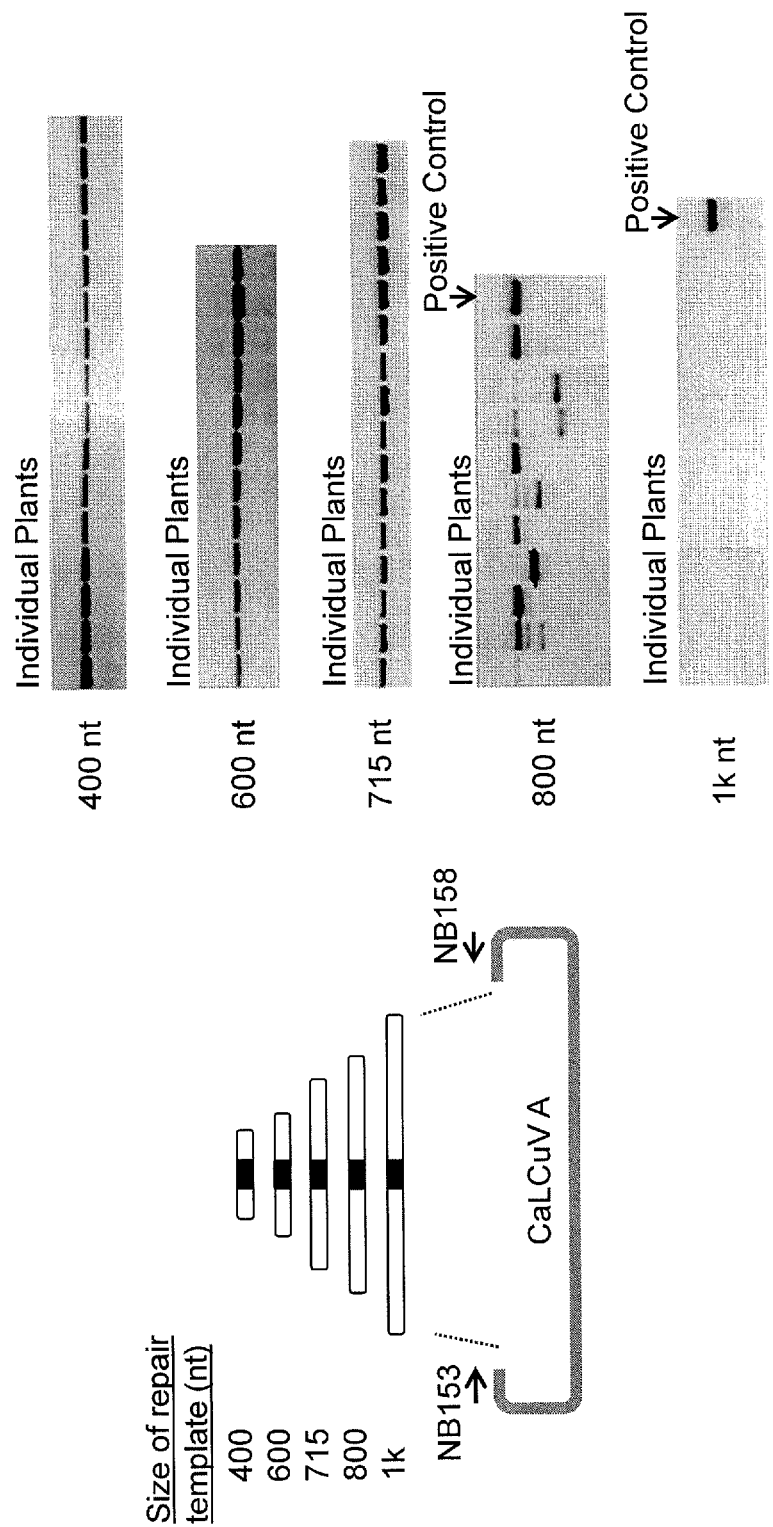
FIG. 6 is a diagram of the CaLCuV A plasmid (left panel) and a series of pictures of gels showing the stability of repair template sequences in infected plants (right panels). Genomic DNA from infected plants was used as a template for PCR amplification of the repair template sequence. Primers NB153 and NB158 (left panel) recognize sequences in the viral genome and amplify across the repair template. Five differently sized repair templates were analyzed. Repair templates with sizes 400 nt, 600 nt, 800 nt, and 1000 nt contained ADH1 homology sequences, while 715 nt contained gus::nptII homology sequence. PCR amplicons (right panel) were run out on a 1% agarose gel. Controls for 1000 nt and 800 nt used plasmid DNA as a template for PCR (CaLCuVA.ADH1-1000 and CaLCuVA.ADH1-800, respectively).

To ensure that the repair template was stably replicated in infected plants, PCR was performed on purified genomic DNA. Notably, DNA isolated from infected plants is a mixture of plant genomic DNA and virus genomic DNA. Primers were designed to recognize viral sequence (non-repair template sequence) in the CaLCuV A plasmid (FIG. 6, left panel), and to amplify across the entire repair template sequence. PCR reactions contained 2.5 µl of 10×NEB Standard Taq buffer, 0.5 µl of 10 mM dNTPs, 0.5 µl of 10 µM primer NB153, 0.5 µl of 10 µM primer NB158, 18.8 µl of dH$_2$O, 0.2 µl of Taq polymerase, and 2 µl of purified genomic DNA (~200 ng). The PCR conditions were 5 minutes at 94° C. followed by 35 cycles of 30 seconds at 94° C., 30 seconds at 55° C., and 1 minute at 72° C. 10 µl of the PCR sample was loaded onto a 1.0% agarose gel. FIG. 6 (right panel) shows the resulting amplicons from infected plants carrying repair templates ranging from 400 nt to 1000 nt. These results suggested that repair templates equal to or less than 715 bp were stably replicated in plant cells. For this reason, only viruses carrying repair templates equal or less than 715 bp were assessed in the subsequent experiments. Based on these experiments, it was concluded that first generation geminiviral vectors effectively amplified and disseminated repair templates in *Arabidopsis* plants.

Detecting GT at the ADH1 Locus

Figure 7:
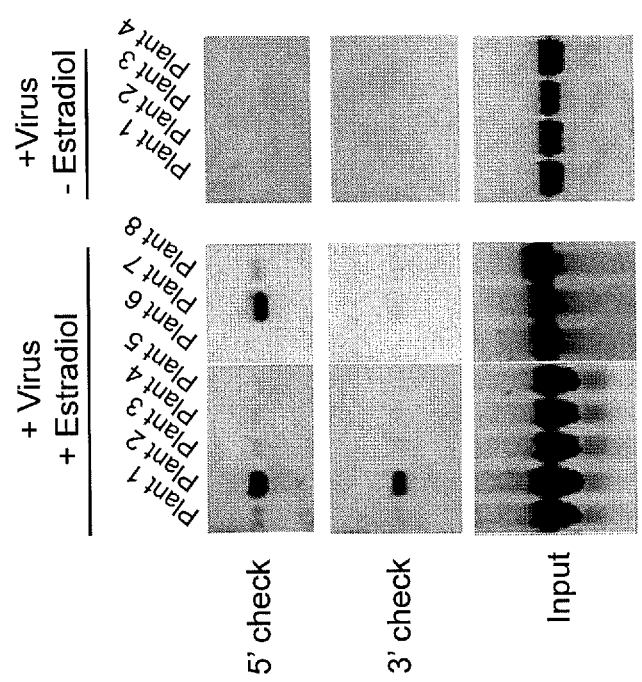
FIG. 7 is a series of pictures of agarose gels showing PCR detection of amplicons from modified ADH1 loci. Genomic DNA from infected plants exposed to β-estradiol (left panels; +Virus, +Estradiol) or not exposed to β-estradiol (right panel; +Virus, −Estradiol) was subjected to nested PCR using primers designed to detect the 5' modification junction (5' check), the 3' modification junction (3' check), and amplification of the starting template (input).

Nested PCR was performed to detect modified ADH1 loci. Primers were designed to amplify the ADH1 locus approximately 700 bp upstream and downstream of the ZFN target sequence. The resulting amplicons were then used as a template for a nested PCR, with primers that specifically recognize the unique 18 bp modification sequence and ADH1 sequence outside the homology arms carried by the virus. In detail, the ADH1 locus was amplified in a PCR reaction containing 2.5 µl of 10×NEB Standard Taq buffer, 0.5 µl of 10 mM dNTPs, 0.5 µl of 10 µM primer NB257, 0.5 µl of 10 µM primer NB258, 18.8 µl of dH$_2$O, 0.2 µl of Taq polymerase, and 2 µl of purified genomic DNA (~200 ng). The PCR conditions were 5 minutes at 94° C. followed by 15 cycles of 30 seconds at 94° C., 30 seconds at 55° C., and 1 minute at 72° C. Amplicons were column purified using the QIAquick Gel Extraction Kit. Purified amplicons were then used as templates for three nested PCRs. The first PCR checked for the 5' modification junction using primers NB154 and NB264. The second PCR checked for the 3' modification junction using primers NB263 and NB155. The third PCR was a control for template amplification and used primers NB155 and NB154. To minimize template switching, PCR was performed using Expand Long Template PCR system (Roche) in a reaction containing 2.5 µl buffer 1, 0.5 µl 10 mM dNTPs, 0.5 µl of 10 µM primer 1, 0.5 µl of 10 µM primer 2, 0.2 µl of the Taq/Tgo polymerase mix, 17.8 µl dH$_2$O, and 3 µl of purified amplicons. The PCR conditions were 5 minutes at 94° C. followed by 30 cycles of 30 seconds at 94° C., 30 seconds at 55° C., and 1 minute at 72° C. Amplicons were run on a 1% agarose gel. In select plants (KU70–/–, ADH1-ZFN+/+ background) that were infected with virus and exposed to β-estradiol, a noticeable amplicon band was present in both the 5' and 3' junction PCRs (FIG. 7). Importantly, plants (Columbia background) that were only infected with the virus did not have detectable amplicons for the 5' and 3' junction PCR. From these results it was concluded that geminiviruses and ZFNs can stimulate GT at an endogenous locus in somatic leaf tissue.

Delivery of Zif268-ZFN for GT at the gus::nptII Locus

GT was stimulated at the gus::nptII transgene. To detect GT by phenotype, plants containing a stably integrated gus::nptII transgene were infected with CaLCuVA.GUS-FIX and CaLCuVB following the procedures described above. Notably, immediately following the truncated GUS nucleotide sequence was a target site for Zif268. For these experiments, Zif268::FokI was transiently delivered to plants 8 dpi by TRV. TRV is a bipartite RNA plant virus that can be used to transiently deliver protein coding sequences to plant cells. In the present experiments, TRV was modified to express Zif268::FokI by replacing the 2b and 2c nucleotide sequences with a subgenomic promoter and the ORF for the Zif268::FokI. Infection was carried out by syringe infiltration of *Agrobacterium* carrying T-DNA coding for both TRV genomes. Briefly, GV3101 *Agrobacterium* carrying T-DNA encoding for TRV1 and TRV2-Zif268 were grown overnight at 28° C. in 3 mL of LB medium containing 50 µg/mL kanamycin and 50 µg/mL gentamycin. One mL of the culture was transferred to 100 mL LB medium containing 50 µg/mL kanamycin and 50 µg/mL gentamycin and grown overnight at 28° C. until they reached an OD of approximately 1.0. Solutions were then centrifuged at 7000 RPM for 10 minutes and resuspended in 50 mL of MMAi solution (0.5 g MS salts, 0.195 g MES, 2 g sucrose, 100 µl of 200 mM acetosyringone per 100 mL at pH 5.6) followed by shaking at 50 rpm for 2 hours. Solutions of *Agrobacterium* containing TRV1 and TRV2-Zif268 were mixed in a 1:1 ratio and syringe infiltrated into three rosette leaves per plant. TRV and geminivirus infected plants were moved to a growth chamber under 12 h light/12 h dark conditions at 22-24° C. for 15 days.

Detecting GT at the gus::nptII Locus

Figure 8:
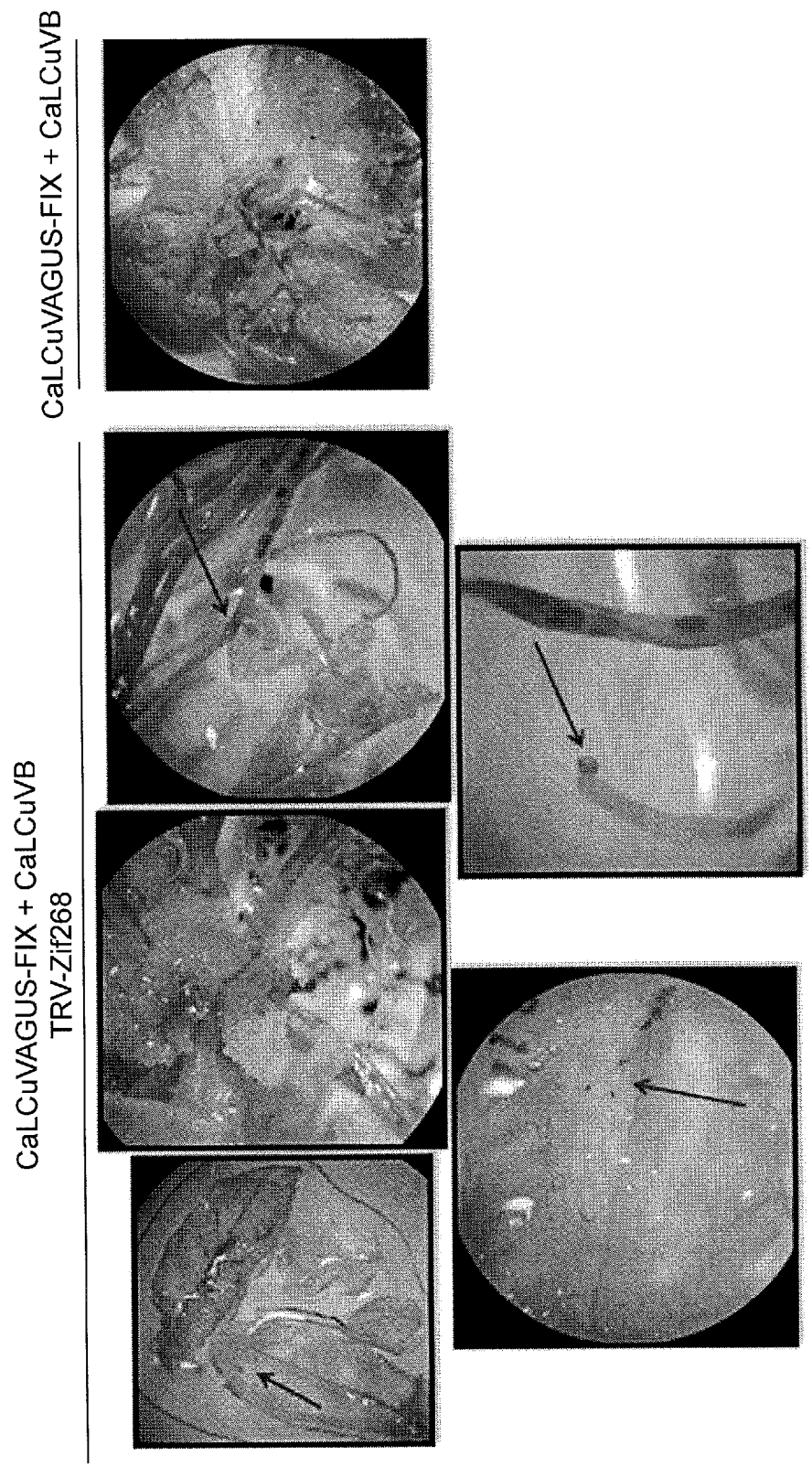
FIG. 8 is a series of pictures showing evidence of GT at the gus::nptII gene. Co-infected plants (CaLCuVA.GUS-FIX and CaLCuVB with TRV-Zif268) were stained in X-Gluc and chlorophyll was removed. Images of selected plants are shown. Arrows point to blue-staining cells.

To detect evidence for GT at the gus::nptII locus, plants were analyzed for cells expressing functional GUS protein. Fifteen days after TRV infection and 23 days after geminivirus infection, plants were stained overnight at 37° C. in an X-Gluc solution (0.052 g X-Gluc (GoldBio), 5 mL 1M sodium phosphate, 0.1 mL Triton X per 100 mL). Plants were removed from the stain and incubated in 75% ethanol for 2-3 days to remove chlorophyll (which helped with visualizing the blue staining). Plants were visualized using a stereoscope. If GT occurred, spots of blue were observed where one or multiple cells had reconstituted GUS expression. Such blue spots also were observed in tissue that developed after biolistic bombardment. FIG. 8 shows images of plants co-infected with CaLCuVA.GUS-FIX and CaLCuVB (or with either plasmid alone) that were stained in X-gluc. The spotty patches of blue staining in the rosette leaves and in the newly developed tissue suggested that GT had occurred. These results indicated that geminiviruses and ZFNs can stimulate GT at a gus::nptII transgene in plant somatic tissue.

Approach for Generating Bean Yellow Dwarf Virus Replicon Vectors

Figure 9:
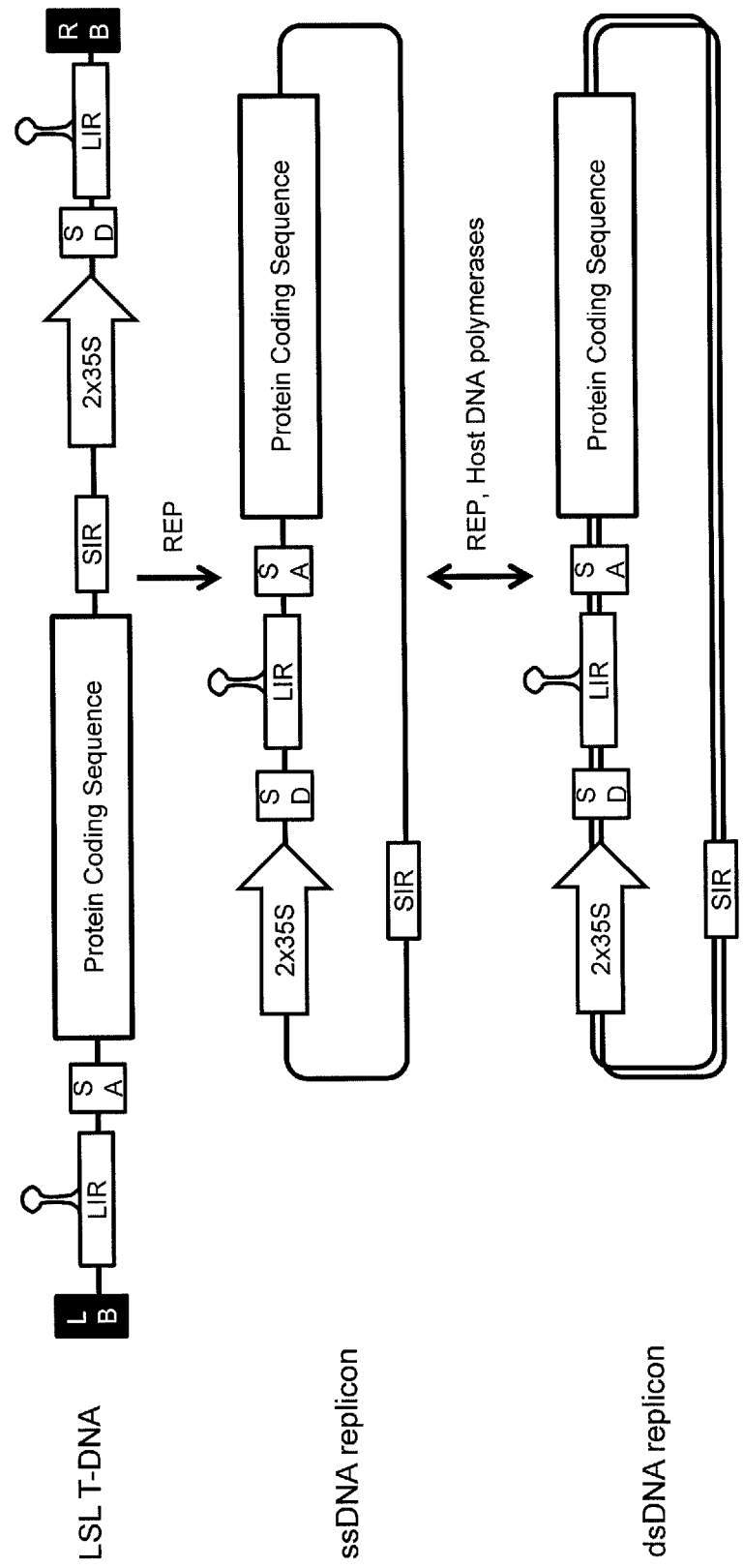
FIG. 9 is an illustration of a strategy for creating a geminivirus replicon (GVR) system for transient protein expression, and subsequently transient genome editing, in plants. LSL T-DNA functions as a template for Rep-assisted replicative release of replicons (top). LIR, SIR, and Rep/RepA nucleotide sequences were derived from Bean yellow dwarf virus (BeYDV, GenBank accession number DQ458791.1). Following delivery of LSL T-DNA to plant cell nuclei by *Agrobacterium*, Rep protein mediates replicational release of single-stranded DNA (ssDNA) replicons (middle). Complementary strand synthesis is carried out by host polymerases, resulting in transcriptionally-competent double-stranded DNA (dsDNA) replicons (bottom). Transcription of protein coding sequence is driven by the nearby LIR and further promoted with an upstream 2×35S promoter. SD, DEM2 splice donor; SA, DEM2 splice acceptor; LB, left border; RB, right border.

An exemplary method for generating bean yellow dwarf virus (BeYDV) replicons in plant cells involves delivery of one or two plasmids or T-DNA molecules that encode the trans-acting replication-associated proteins, Rep/RepA, and direct duplications of the large intergenic region (LIR) flanking sequence encoding the small intergenic region (SIR; FIGS. 9-10). Normally, virus replication is initiated by Rep protein binding to LIR sequence on a circular dsDNA genome. However, if the geminivirus genome is linearized and contains flanking LIR sequences (also referred to as an LSL vector), Rep proteins bind to the LIR sequences and release circularized, single-stranded geminiviral replicons (GVRs). Replicons can then be used as a template for replicase-mediated genome amplification. Consequently, any sequence present inside the flanking LIRs will be present in the replicon. Eliminating coat protein and movement protein sequence abolishes cell-cell movement, but significantly lessens genome-size restraints imposed by plasmodesmata. To compensate for loss of cell-cell movement, *Agrobacterium* was used to direct GVR production in specific cells. To facilitate cloning of endonuclease and repair template sequence into an LSL destination vector, MultiSite Gateway cloning technology (Invitrogen) was implemented.

Constructing an LSL Destination T-DNA Plasmid

Figure 10A:
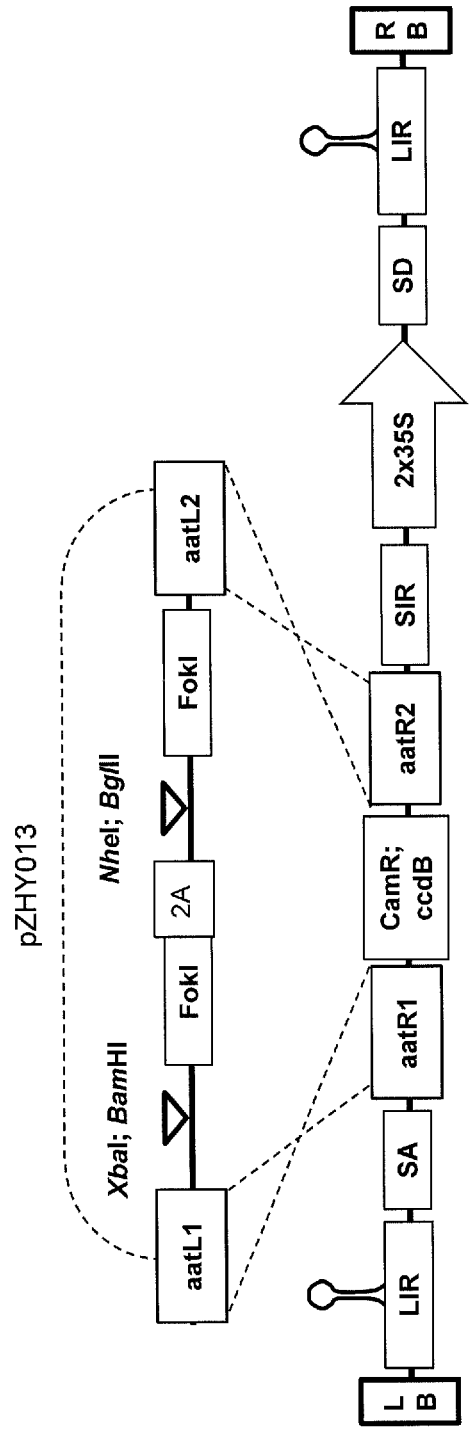
FIG. 10A is an illustration of an approach for cloning customizable endonucleases into pLSL. The pZHY013 entry vector, encodes unique restriction enzyme sites (XbaI, BamHI, NheI and BglII) for sequential cloning of nucleotide sequences for TALE or ZF binding domains.
Figure 10B:
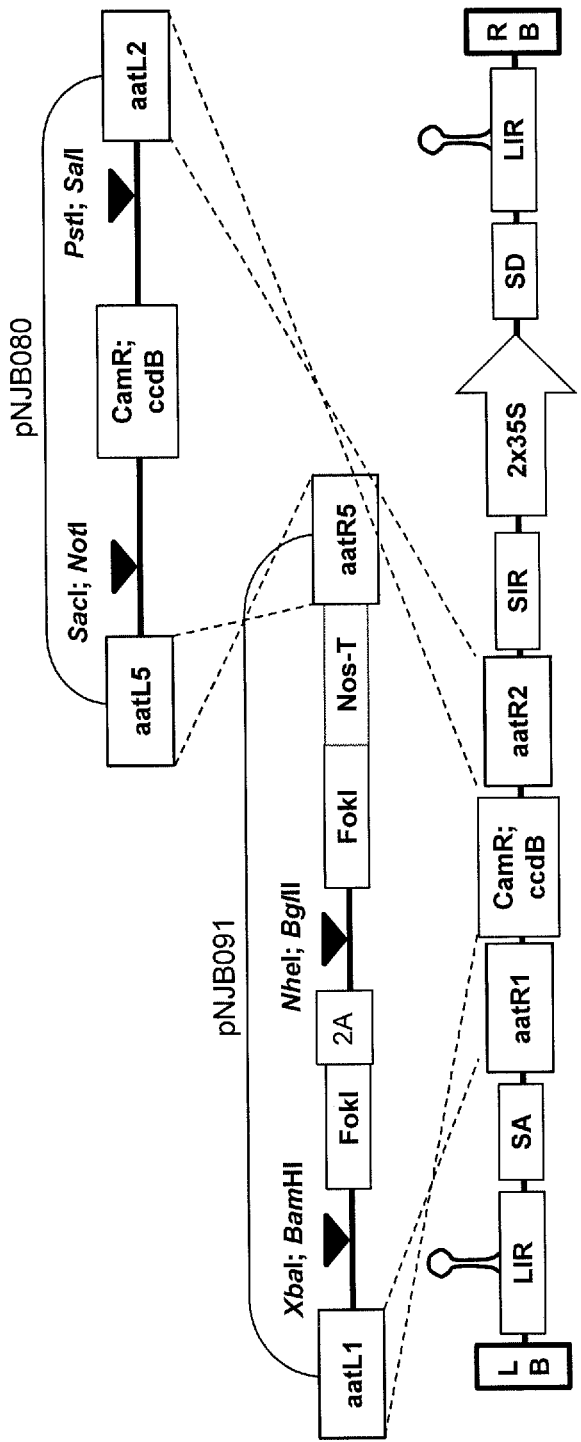
FIG. 10B is an illustration of vectors for Gateway cloning of customizable endonucleases and repair templates into pLSL. FokI nucleotide sequences encode obligate heterodimeric proteins (EL-KK). Noteworthy, an AatII enzyme site permits cloning of Cas9 or MN nucleotide sequences upstream of Nos terminator sequence (Nos-T).
Figure 10C:
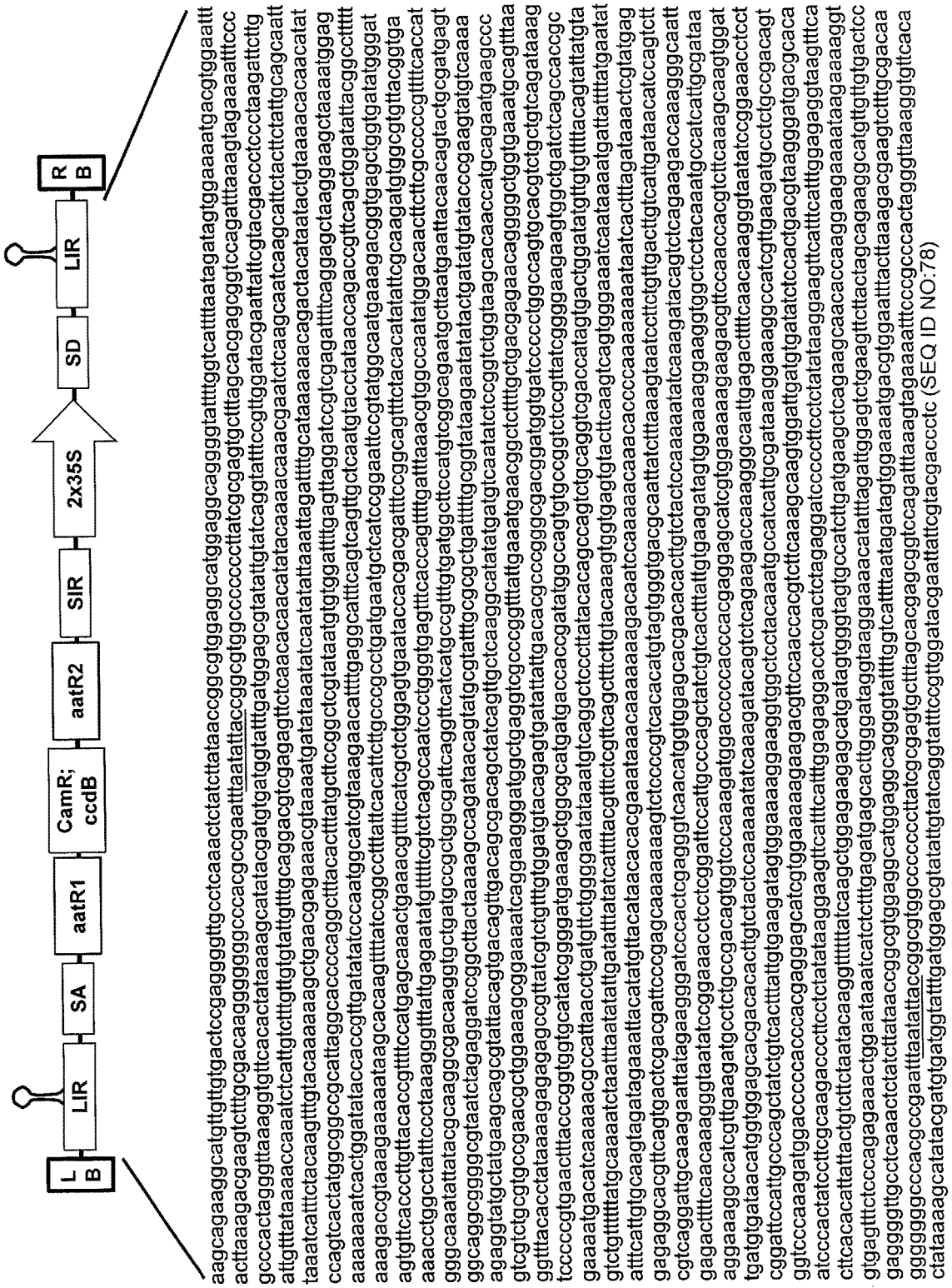
FIG. 10C is the full sequence of the LSL region (SEQ ID NO:78) located between the left and right T-DNA borders in pLSL. The hygromycin resistance gene, located between the left border and the upstream LIR, is not shown. The highly-conserved nonanucleotide sequence (TAATATTAC), required for Rep-initiated rolling circle replication, is underlined in both LIR elements.

The following describes methods for constructing a BeYDV-derived LSL destination T-DNA plasmid (pLSL; FIGS. 9-10). Assembly of the complete LSL nucleotide sequence was accomplished by cloning smaller "blocks" of LSL sequence into pBluescript KS+ plasmids before cloning into a pCAMBIA1300 T-DNA backbone. The first block was designed to contain LIR::DEM2 splice acceptor (last 62 nt of the DEM2 intron)::tobacco etch virus (TEV) 5' UTR (last 93 nt of the TEV 5' UTR) attR1 chloramphenicol resistance gene (CmR). The second block contained ccdB attR2 SIR. The third block contained 2×355 TEV 5' UTR (first 38 nt of the TEV 5' UTR)::DEM2 splice donor (first 32 nt of the DEM2 intron)::LIR. LIR and SIR sequences were obtained from the mild BeYDV isolate (GenBank accession number DQ458791.1). To generate attR1::CmR sequence for block 1, pFZ19 was used as a template for PCR amplification using primers NB326 and NB327. PCR solutions contained 2.5 µl of 10× cloned Pfu buffer, 0.5 µl of 10 mM dNTPs, 0.5 µl of 10 µM primer NB326, 0.5 µl of 10 µM primer NB327, 18.5 µl of dH$_2$O, 0.5 µl of Pfu enzyme, and 2 µl of plasmid DNA (~20 ng). PCR cycling included 5 minutes at 94° C., followed by 30 cycles of 30 seconds at 94° C., 30 seconds at 55° C., and 2 minutes at 72° C. PCR amplicons were column purified using the QIAquick gel extraction kit. Purified amplicons were then used in an OE-PCR with NB330 and NB331 to generate the complete nucleotide sequence for block 1. OE-PCR solutions contained 2.5 µl of 10× cloned Pfu buffer, 0.5 µl of 10 mM dNTPs, 0.5 µl of 10 µM primer NB327, 0.5 µl of 10 µM primer NB325, 14.5 µl of dH$_2$O, 0.5 µl of Pfu enzyme, and 2 µl of purified amplicons, NB330 (2 ng) and NB331 (2 ng). PCR cycling consisted of 5 minutes at 94° C., followed by 30 cycles of 30 seconds at 94° C., 30 seconds at 55° C., and 4 minutes at 72° C. Amplicons and 1 µg of pBluescript KS+ vector were digested with KpnI and XbaI. Digested fragments were purified and ligated following standard procedures. The resulting ligation was transformed into DH5a *E. coli* cells following standard procedures. Herein, the sequence verified plasmid containing block 1 is termed pBlock1. Blocks 2 and 3 were constructed using similar methods. Construction of Block 2 first required amplification and purification of ccdB attR2 from pFZ19 using primers NB328 and NB332. Purified amplicons were added to an OE-PCR with NB344 and primers NB328+NB329 to generate the complete nucleotide sequence for block 2. Purified amplicons were ligated into pBluescript KS+ with XbaI and SacI and transformed into ccdB-resistant XL-1 Blue cells to generate pBlock2. Construction of block 3 first required PCR amplification of 2×35S sequence from pMDC32 using primers NB333+NB334. To generate the complete nucleotide sequence for block 3, purified amplicons were used in an OE-PCR with NB335 and NB336 using primers NB333 and NB337. Purified amplicons were ligated into pBluescript KS+ with XhoI and SacI, and transformed into DH5a cells to generate pBlock3. Nucleotide sequences for the two LIR elements in pBlock1 and pBlock3 were designed to contain inverted homodimeric BsaI to facilitate cloning of the conserved hairpin structure. To complete the hairpin structure, pBlock1 and pBlock3 were digested with BsaI and gel purified. Primers NB338 and NB339 were dephosphorylated, annealed, ligated into pBlock1 and pBlock3 vector backbones, and transformed into DH5a to generate pBlock1HP and pBlock3HP. To construct the final LSL vector, pBlock1HP, pBlock2, pBlock3HP, pCAMBIA1300 were digested with SbfI+XbaI, XbaI+XhoI, XhoI+SbfI, and SbfI, respectively. Fragments of the expected sizes were gel purified, ligated, and transformed into ccdB-resistant XL-1 Blue cells following standard protocols for 4-way ligations. The resulting plasmid (pLSL, FIG. 10C) was sequence verified and used as a destination vector for MultiSite Gateway cloning.

Constructing a Nuclease-Entry Plasmid

A nuclease-entry vector was constructed for MultiSite Gateway cloning into pLSL (pNJB091; FIG. 10B). Four unique restriction enzyme sites immediately upstream of two FokI coding sequences allows for sequential cloning of custom-designed DNA binding domains. To construct pNJB091, pZHY013 (a modified pCR8 entry vector encoding FokI heterodimer sequences; FIG. 10A) and NB318 were digested with BsmI and EcoRV. Digested fragments were gel purified, ligated and transformed into DH5a cells following standard protocols.

Constructing a Donor-Entry Plasmid

A donor-entry vector was constructed for MultiSite Gateway cloning into pLSL (pNJB080; FIG. 10B). Two unique pairs of restriction enzyme sites flanking ccdB and CmR selection markers permit efficient cloning of repair templates. To construct pNJB80, sequence encoding the CmR and ccdB genes was amplified by PCR from pFZ19 using NB316+NB317 primers. Amplicons were purified and used in an OE-PCR with NB314 and primers NB315 and NB317. PCR solutions contained 2.5 µl of 10× cloned Pfu buffer, 0.5 µl of 10 mM dNTPs, 0.5 µl of 10 µM NB315, 0.5 µl of 10 µM NB317, 16.5 µl of dH$_2$O, 0.5 µl of Pfu enzyme, 2 µl of purified amplicons, and 2 µl of 10 µM NB314. PCR cycling included 5 minutes at 94° C., followed by 30 cycles of 30 seconds at 94° C., 30 seconds at 55° C., and 3 minutes at 72° C. Resulting amplicons were gel purified following standard procedures. Amplicons and pZHY558 were digested with ApaI and BsrGI, ligated, and transformed into ccdB-resistant cells following standard procedures. MultiSite Gateway recombination with pNEL1R5 into pLSL positions repair template sequence between two transcriptional-termination sequences (upstream Nos-T sequence and downstream SIR sequence). The studies herein may benefit from flanking termination sequences. For example, transcriptional gene silencing is facilitated through production of RNA molecules with homology to an endogenous gene. Reducing read-through transcription of repair template sequence may decrease unintentional silencing of targeted genes.

Constructing Replicase-Expressing T-DNA Plasmids

To initiate replicational release of GVRs from LSL T-DNA, trans-acting Rep/RepA proteins must be expressed. Here, two Rep/RepA T-DNA expression plasmids were constructed. The first plasmid encodes the Rep/RepA coding sequence downstream of an estradiol-inducible XVE promoter (pXVEREP), such that when integrated into the plant genome, Rep/RepA expression can be induced by exposing plant tissue to β-estradiol. The second plasmid encodes Rep/RepA downstream of a 2×35S promoter (p35SREP). For each plasmid, WT RepA and mutant RepA (RepA LxCxQ; Liu et al., Virology 256:270-279, 1999) versions are created (pXVEREPLxCxQ and p35SREPLxCxQ). Normally, RepA interacts with the host cell's retinoblastoma (RB) protein, sequestering its repressive activity on E2F. This promotes entry into S phase, and, in turn, provides the invading geminivirus with replication machinery needed to amplify its genome. The studies described herein may benefit from a RepA protein that does not interact with RB. For example, in actively dividing meristem cells or germline cells, factors required for replicon amplification should already be present. Thus, there may be little need to inactivate RB in these cell types. Furthermore, expression of RepA LxCxQ may result in decreased toxicity in these cell types—which may facilitate recovery of modified seeds.

Figure 11:
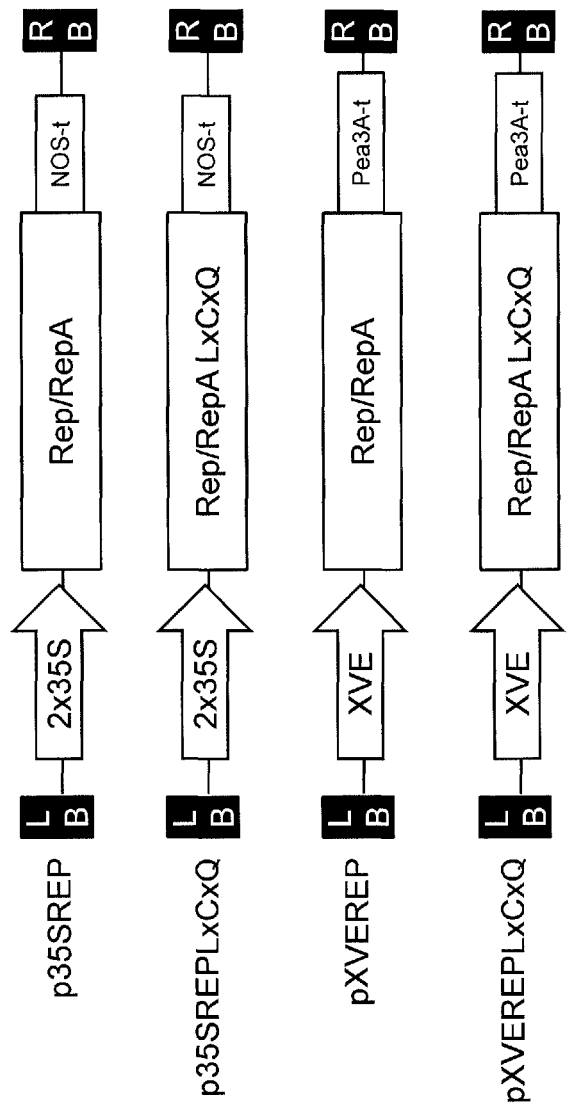
FIG. 11 is an illustration showing the general structure of the replicase expressing T-DNA plasmids used in the experiments described herein. Rep/RepA nucleotide sequences (both wild type and LxCxQ) were cloned into pMDC32 (2×355 promoter) or pFZ19 (XVE promoter).

To generate pXVEREP, p35SREP, pXVEREPLxCxQ, and p35SREPLxCxQ (FIG. 11), WT and mutant Rep/RepA coding sequences were amplified by OE-PCR using NB319, NB320, and NB322, and primers NB323 and NB324 (WT Rep/RepA), or using NB319, NB321, and NB322, and primers NB323 and NB324 (mutant Rep/RepA). PCR solutions consisted of 2.5 µl of 10× cloned Pfu buffer, 0.5 µl of 10 mM dNTPs, 0.5 µl of 10 µM NB323, 0.5 µl of 10 µM NB324, 14.5 µl of dH$_2$O, 0.5 µl of Pfu enzyme, and 2 µl of each DNA component. PCR cycling included 5 minutes at 94° C., followed by 30 cycles of 30 seconds at 94° C., 30 seconds at 55° C., and 3 minutes at 72° C. Resulting amplicons were purified using the QIAquick gel extraction kit. One µl of purified amplicons was combined with 150 ng of pFZ19 or pMDC32 (2×35S Ti-DNA vector) and recombination was stimulated using LR clonase (Invitrogen) as described by the manufacturer's protocol. Plasmid from the resulting solution was transformed into DH5a, and cells were plated on LB plates containing 50 µg/mL kanamycin.

Figure 12:
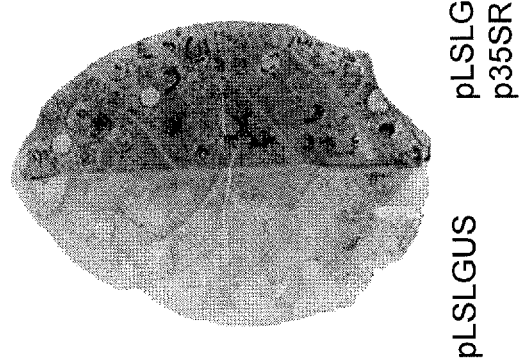
FIG. 12 is an image of plant tissue expressing GUS enzyme. LSL T-DNA, encoding NLS-tagged beta-glucuronidase (pLSLGUS), was delivered to Nicotiana tabacum var. xanthi leaf tissue with p35SREP (right side of leaf) or without p35SREP (left side of leaf) by syringe infiltration of Agrobacterium. Transformed leaf tissue was stained seven days post infiltration (dpi) with X-Gluc, and chlorophyll was removed to better visualize staining.
Figure 13:
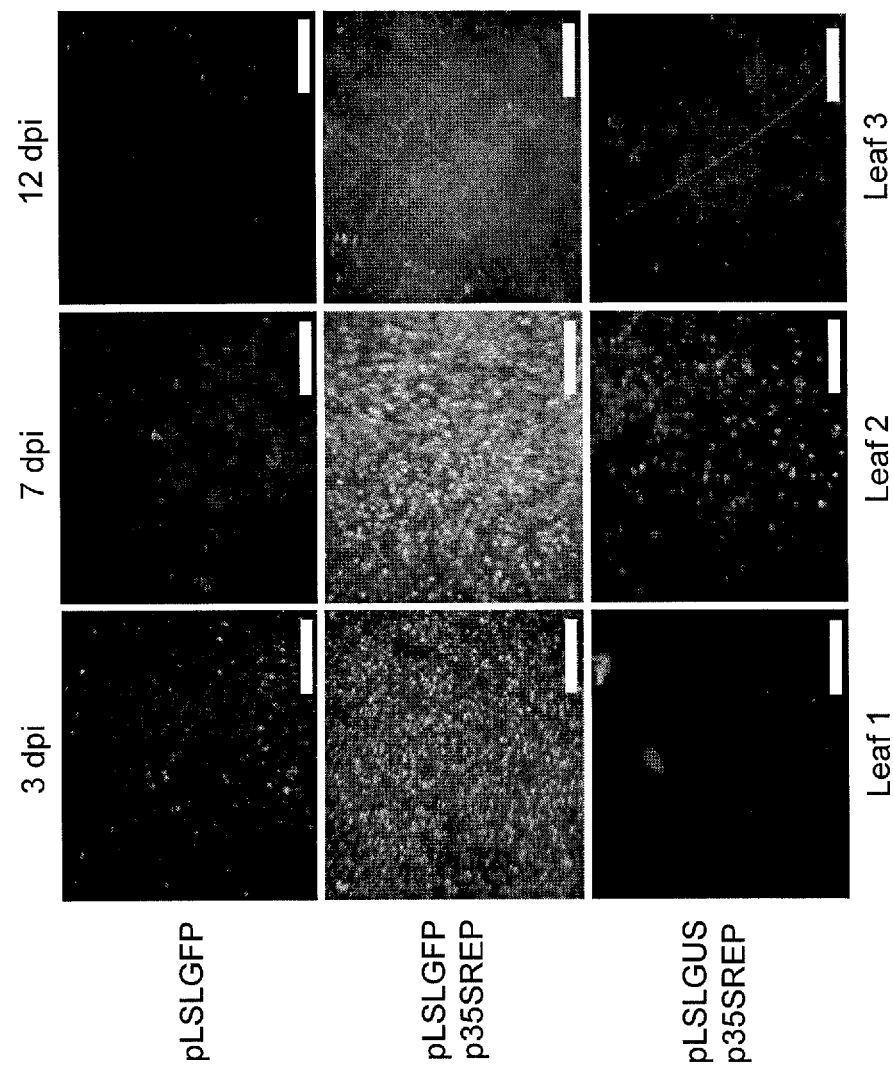
FIG. 13 is a series of images of plant tissue expressing GFP. Leaf tissue transformed with pLSLGFP, with and without delivery of p35SREP, or transformed with pLSL-GUS with delivery of p35SREP, was visualized 3, 7, and 12 dpi.
Figure 14:
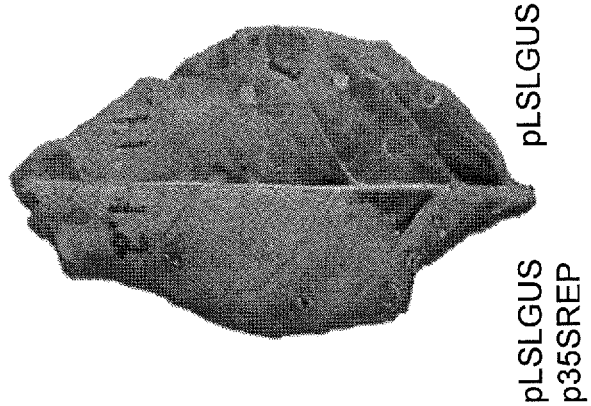
FIG. 14 is an image of a representative leaf seven dpi, demonstrating tissue health. Leaf tissue from WT Nicotiana tabacum plants was syringe infiltrated with Agrobacterium containing pLSLGUS (right), or coinfiltrated with Agrobacterium containing pLSLGUS and p35SREP. Leaf tissue was removed from the plant seven dpi and imaged. Slight browning in tissue transformed with p35SREP was observed.
Figure 15:
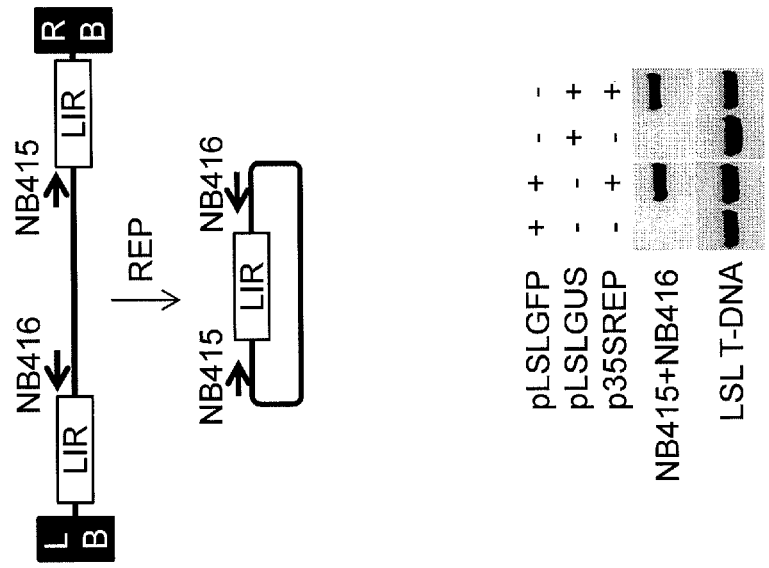
FIG. 15 is an illustration (top) and example (bottom) of detecting GVRs encoding GUS and GFP nucleotide sequences in plant cells. To assay for the presence of GVRs, genomic DNA was extracted three dpi and used as template for PCR. Primers were designed to amplify LIR sequence contained on the replicon. Amplicons were present only when p35SREP was co-transformed with pLSL, suggesting the presence of GVRs.

Demonstrating Transient Delivery of Reporter Proteins in *Nicotiana tabacum* Leaf Tissue Using GVRs Functionality of the system was tested by attempting to transiently express reporter proteins in somatic leaf tissue. To this end, pLSL was modified to encode NLS-tagged green fluorescent protein (pLSLGFP) or beta-glucuronidase (pLSLGUS). GFP and GUS nucleotide sequence were amplified from, respectively, pTC23 and pNB67 using primers NB362 and NB363, and primers NB448 and NB449. Forward and reverse primers contained XbaI and AatII restriction enzyme sites, respectively for cloning into pNB091. The resulting vectors were used in a MultiSite Gateway recombination reaction with pLSL and pNB098 (a modified version of pNB080 with a repair template to correct a non-functional gus::nptII transgene) to generate pLSLGFP and pLSLGUS. These vectors were sequence verified and transformed into *Agrobacterium tumefaciens* GV3101 by the freeze-thaw method. Single colonies of transformed *Agrobacterium* were grown overnight in a shaker at 28° C. in 5 mL of LB starter culture with 50 µg/ml kanamycin and 50 µg/ml gentamicin. The next day, 1 ml was used to inoculate 50 mL of LB culture with 50 µg/ml kanamycin and 50 µg/ml gentamicin. After reaching an OD$_{600}$ of 1 (approximately 16 hours), cells were pelleted, and resuspended to an OD$_{600}$ of 0.2 in infiltration buffer (10 mM 2-(N-morpholino) ethanesulfonic acid (MES), and 10 mM MgSO$_4$, pH 5.6). Resuspended cultures were incubated at room temperature for 2 hours before infiltration. To demonstrate transient expression of GUS, half leaves were fully infiltrated with *Agrobacterium* containing pLSLGUS or a 1:1 mixture of *Agrobacterium* containing pLSLGUS and p35SREP. Seven dpi infected leaf tissue was excised from the plant and stained in X-Gluc for 24 hours at 37° C. Chlorophyll was removed using 80% ethanol, and leaf images were taken (FIG. 12). To demonstrate transient expression of GFP, three leaves were syringe infiltrated with *Agrobacterium* containing pLSLGFP, or infiltrated with a 1:1 mixture of *Agrobacterium* containing pLSLGFP and p35SREP or pLSLGUS and p35SREP. Images capturing GFP fluorescence were taken 3, 7, and 12 dpi (FIG. 13). Both GUS and GFP expression were markedly enhanced when p35SREP was co-delivered. Notably, a slight browning of leaf tissue was observed 7 dpi due to replicase expression (FIG. 14). To correlate enhanced protein expression with replicon production, Rep-assisted replicational release was evaluated by PCR (FIG. 15, top). To this end, DNA was extracted from leaf tissue infiltrated with *Agrobacterium* containing pLSLGFP or pLSLGUS, or infiltrated with a 1:1 mixture of *Agrobacterium* containing pLSLGFP or pLSLGUS and p35SREP. Circular replicons were detected by PCR using primers NB415 and NB416. Template switching was minimized by using the Expand Long Template PCR mix (Roche) following manufacturer's protocols. Strong amplification of LIR sequence only from samples co-transformed with p35SREP suggests that GVRs were present in the transformed cells (FIG. 15, bottom). Taken together, these data illustrate that GVRs can facilitate transient delivery of reporter proteins.

Figure 16:
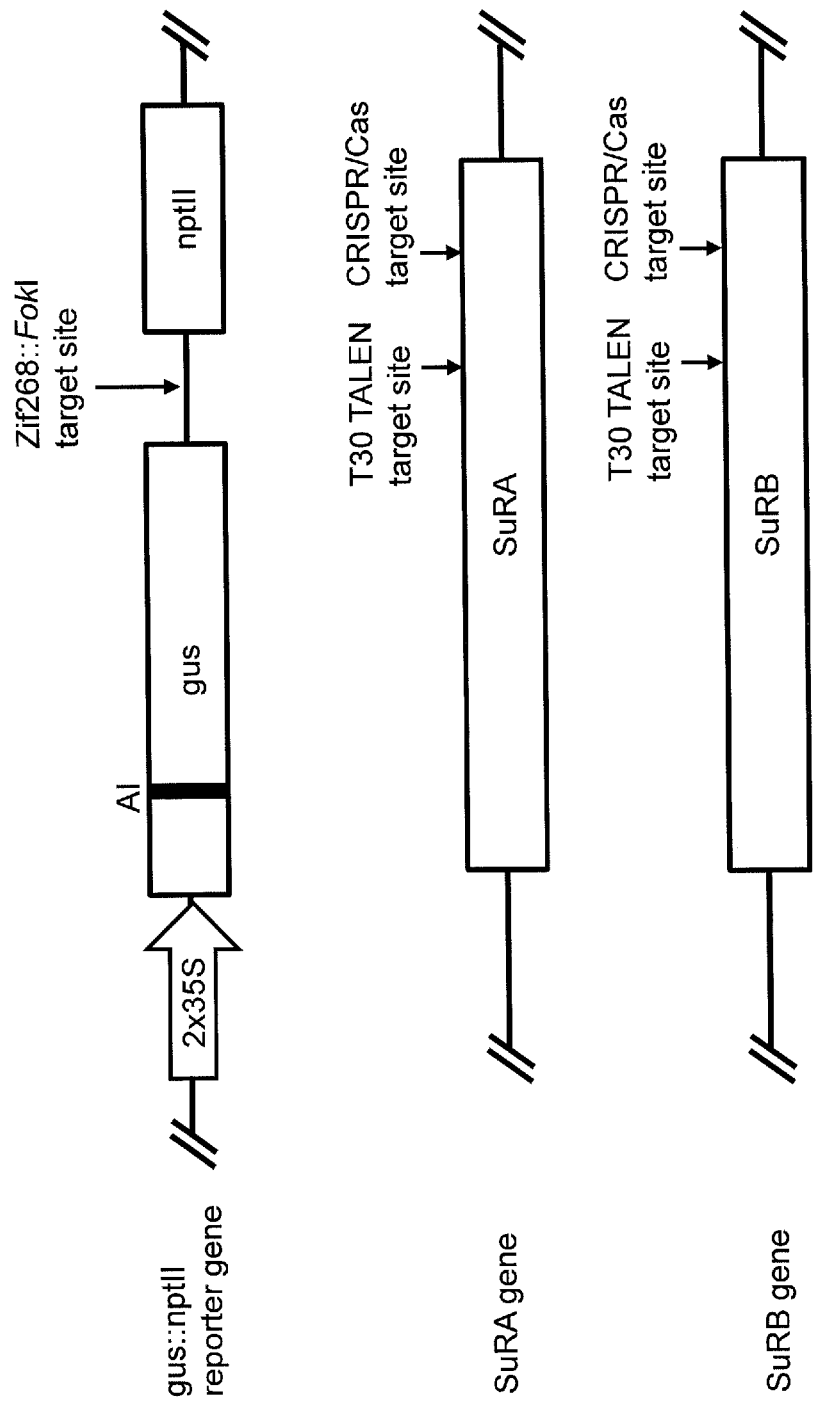
FIG. 16 is an illustration of target loci for Zif268::FokI, the T30 TALE nuclease pair, and the CRISPR/Cas system. ZFN target sequence is present within a stably integrated, and defective gus::nptII reporter gene (top). The T30 TALE nuclease and CRISPR/Cas target sequences are present within the endogenous acetolactate synthase genes (ALS), SuRA (middle) and SuRB (bottom). AI, artificial intron IV of ST-LS1 gene from Solanum tuberosum.
Figure 17:
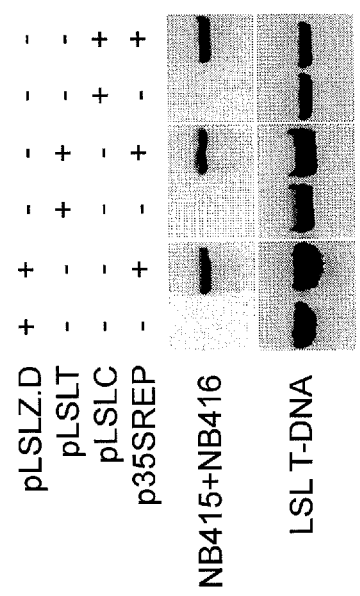
FIG. 17 is an image of a gel from a PCR designed to detect GVRs containing ZFN (pLSLZ.D), TALE nuclease (pLSLT), and CRISPR/Cas (pLSLC) sequences.
Figure 18:
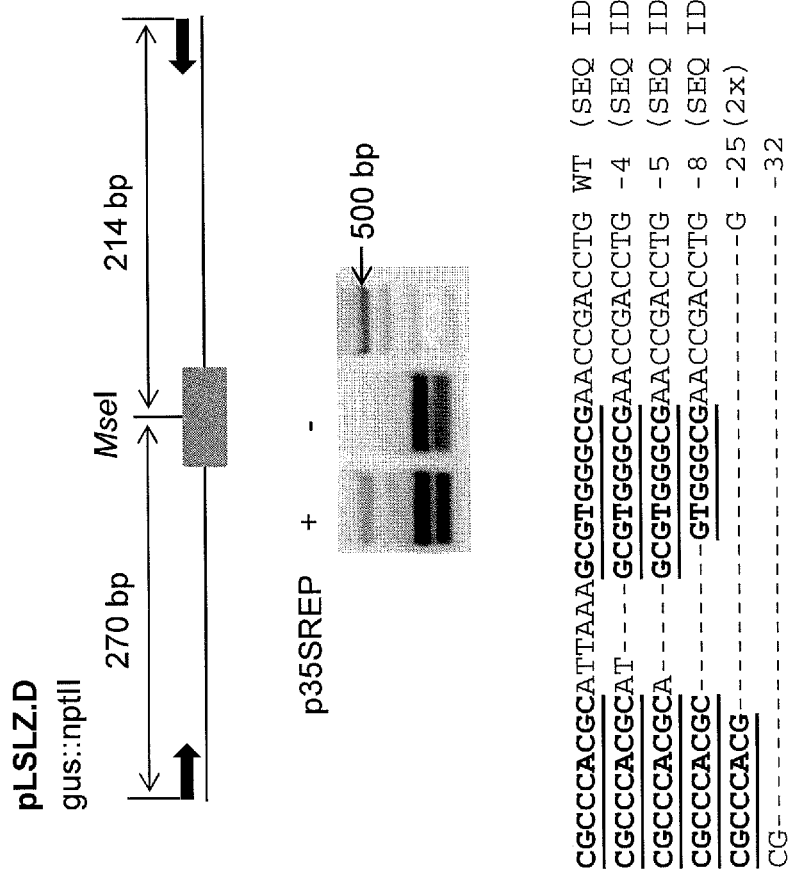
FIG. 18 is an image of a gel (middle) from a PCR-digest (top) designed to detect ZFN-induced mutations at the gus::nptII gene. Plant DNA was isolated from leaf tissue seven dpi. Amplicons encompassing the ZFN target site were digested overnight with MseI and separated on an agarose gel. Cleavage-resistant bands were cloned into pJet1.2 and sequenced (bottom).

Demonstrating Targeted Mutagenesis by Delivery of ZFNs in *Nicotiana tabacum* Leaf Tissue Using GVRs To demonstrate targeted mutagenesis, pLSL was modified to encode a Zif268::FokI ZFN. Zif268::FokI sequence was amplified from pDW1345 using primers NB379 and NB380. Forward and reverse primers contained XbaI and AatII restriction enzyme sites for cloning into pNJB091. The resulting vector was used in a MultiSite Gateway recombination reaction with pLSL and pNB098 to generate pLSLZ.D. The resulting vectors were sequence verified and transformed into *Agrobacterium tumefaciens* GV3101 by the freeze-thaw method. Target sequence for Zif268 is present within a gus::nptII reporter gene that is stably integrated in the genome of *N. tabacum* plants (FIG. 16). Leaf tissue was syringe infiltrated with *Agrobacterium* containing pLSLZ.D, or coinfiltrated with *Agrobacterium* containing pLSLZ.D and p35SREP. Plant DNA was extracted seven dpi, replicational release was verified (FIG. 17), and Zif268 target sequence was analyzed for ZFN-induced non-homologous end joining (NHEJ) mutations. To this end, a 484 bp DNA sequence, encoding the Zif268 target sequence, was amplified by PCR using primers NB422 and NB424. The resulting amplicons were purified and used as a template in a second PCR with primers NB396 and NB307 (FIG. 18). The PCR product was digested overnight with MseI and separated on an agarose gel. Cleavage-resistant products, present only in the pLSLZD and p35SREP lane, were cloned and sequenced (FIG. 18). Six out of eight sequenced clones contained mutations at the Zif268 target sequence. Five out of the six sequences encoded distinct NHEJ mutations suggesting GVR-mediated delivery of Zif268:FokI occurred in multiple somatic cells. Furthermore, densitometry analysis of cleavage-resistant amplicons indicates approximately 10% of reporter genes encode NHEJ mutations. Together, these results suggest GVRs enable targeted mutagenesis by the transient delivery of ZFN protein.

Figure 19:
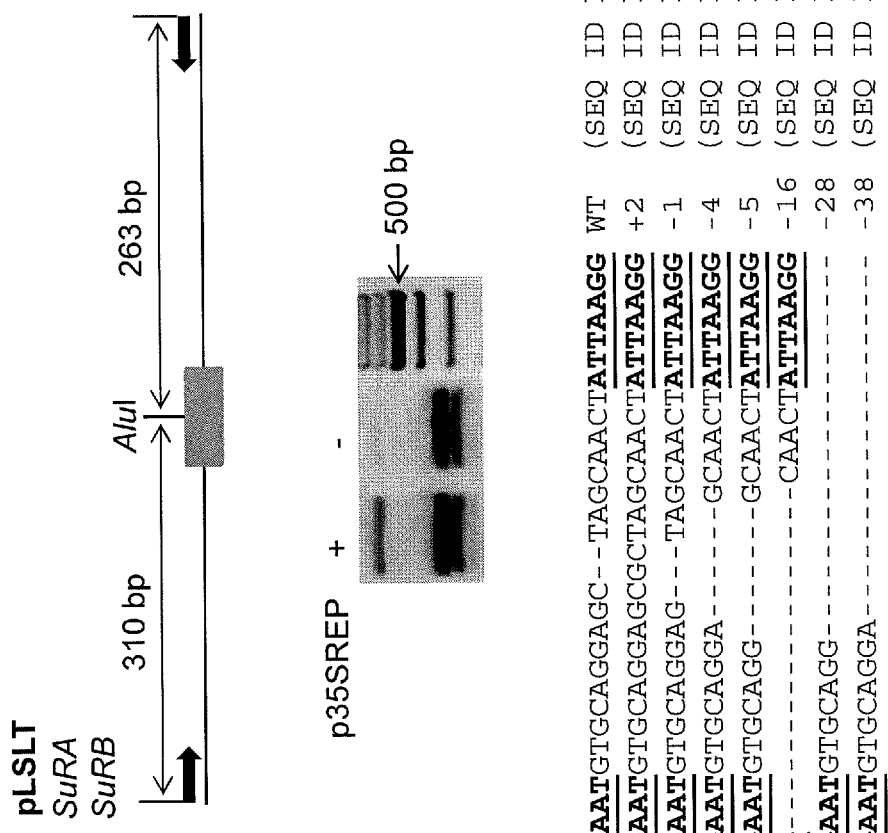
FIG. 19 is an image of a gel (middle) from an enrichment PCR (top) designed to detect TALE nuclease-induced mutations at the ALS loci. Plant DNA was pre-digested overnight with AluI before PCR amplification of SuRA and SurB loci. Amplicons were digested overnight with AluI, separated on an agarose gel, and cleavage-resistant bands were cloned into pJet1.2 and sequenced (bottom).

Demonstrating Targeted Mutagenesis by Delivery of TALE Nucleases in *Nicotiana tabacum* Leaf Tissue Using GVRs Replicon-mediated expression of a ZFN monomer is predicted to be efficient due to its relatively small coding sequence (the Zif268::FokI gene is 897 nt) and minimal sequence repeats. To assess whether GVRs can facilitate delivery of large and repetitive TALE nuclease sequence, pLSL was modified to encode two TALE nuclease sequences separated by a T2A translational-skipping sequence (pLSLT). Target sequence for the TALE nuclease pair is present within two endogenous ALS genes, SuRA and SuRB (Zhang et al., Plant Physiol. 161:20-27, 2012, FIG. 16). WT N. tabacum leaves were syringe infiltrated with Agrobacterium containing pLSLT, or coinfiltrated with Agrobacterium containing pLSLT and p35SREP. Plant DNA was extracted seven dpi, replicational release was verified (FIG. 17), and SuRA and SuRB loci were amplified following an initial digestion of genomic DNA with AluI. Resulting amplicons were digested with AluI overnight and separated on an agarose gel (FIG. 19). Sequencing of cleavage-resistant amplicons confirmed TALE nuclease-induced NHEJ mutations in seven out of eleven clones. These results suggest GVR-mediated TALE nuclease expression can be achieved.

Figure 20:
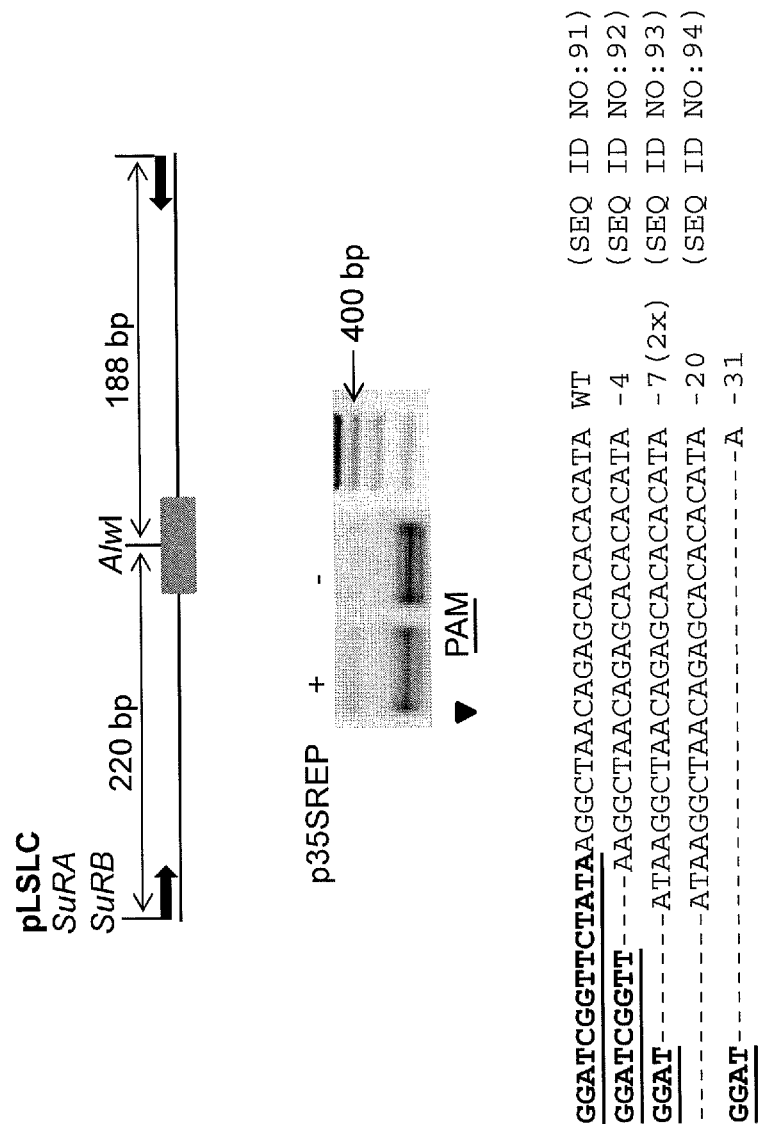
FIG. 20 is an image of a gel (middle) from a PCR-digest (top) designed to detect Cas9-included mutations at the ALS loci. Plant DNA was isolated from leaf tissue five dpi and the CRISPR/Cas target site was amplified by PCR. The resulting amplicons were digested with AlwI, separated on an agarose gel, and cleavage resistant bands were cloned and sequenced (bottom).

Demonstrating Targeted Mutagenesis by Delivery of CRISPR/Cas Elements in Nicotiana tabacum Leaf Tissue Using GVRs The CRISPR/Cas system functions to protect bacteria and archaea against invading foreign nucleic acid. It was previously demonstrated that targeted DNA double-strand breaks (DSBs) could be created in mammalian cells by expression of the Cas9 endonuclease and a programmable guide RNA (gRNA). We tested whether the CRISPR/Cas system is functional in plant cells using GVRs to deliver the components necessary for targeted DNA cleavage. The LSL T-DNA was modified to encode a plant codon-optimized Cas9 followed by gRNA driven by an AtU6 RNA polymerase III promoter. The gRNA was designed to recognize a site in SuRA and SuRB approximately 100 bp downstream of the T30 TALEN target (FIG. 16). Genomic DNA was extracted five dpi, replicational release was verified (FIG. 17; pLSLC), and PCR products encompassing the gRNA target were subjected to AlwI digestion (FIG. 20). DNA sequencing of AlwI resistant products derived from the sample transformed with pLSLC and p35SREP confirmed the presence of mutations at the predicted target site in five out of seven clones. Notably, one of the mutant amplicons contained an intact AlwI site but also had a four bp deletion; recovery of this mutant was likely due to incomplete digestion of the PCR amplicon. The data demonstrate that the CRISPR/Cas system can be used to make targeted modifications to plant genomes and that GVRs can simultaneously deliver gRNA and the Cas9 endonuclease.

Demonstrating GT in Nicotiana tabacum Using GVRs

Figure 21:
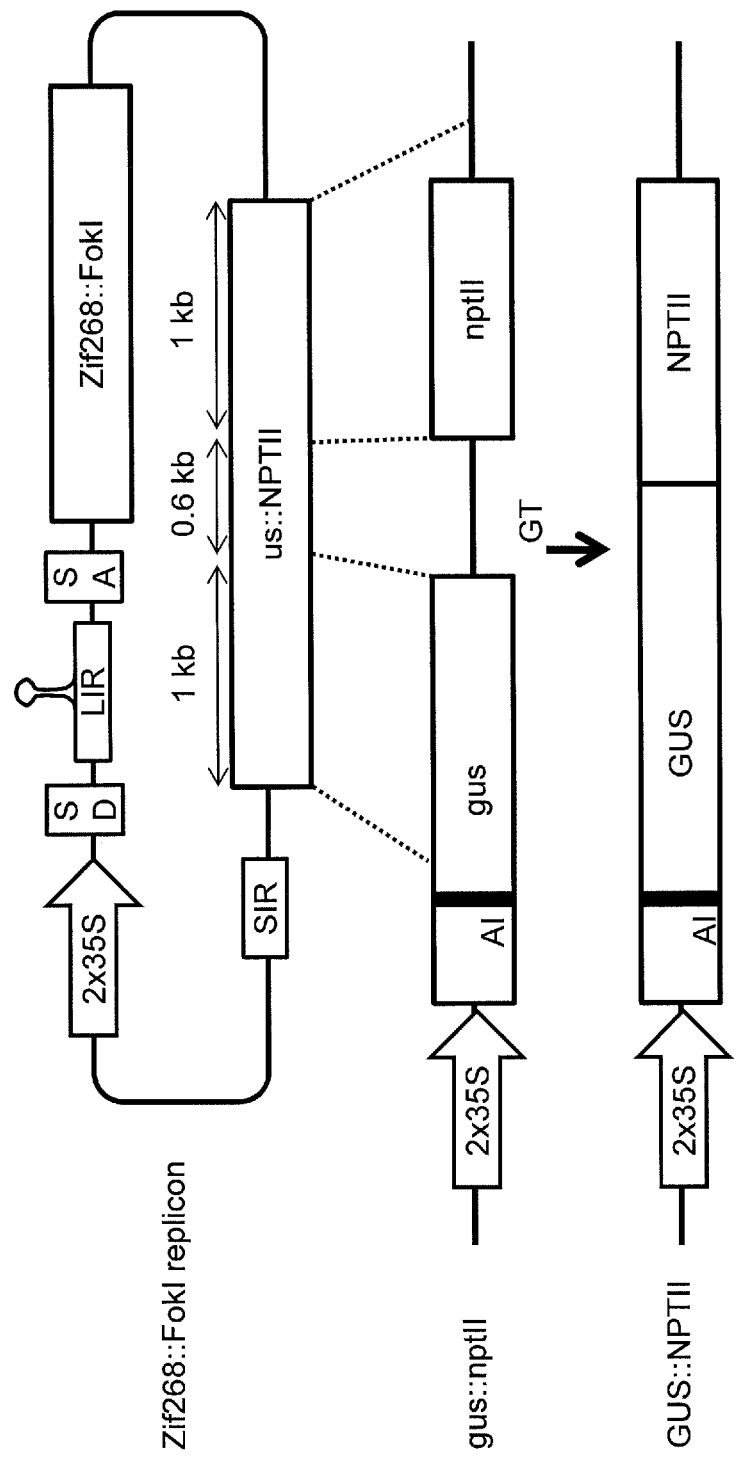
FIG. 21 is a schematic outlining the approach to correct a non-functional gus::nptII reporter. Repair template sequence, present within pLSLZ.D, encodes 1 kb homology arms isogenic to gus::nptII sequence, as well as 600 bp of sequence designed to restore gus::nptII protein function.
Figure 22:
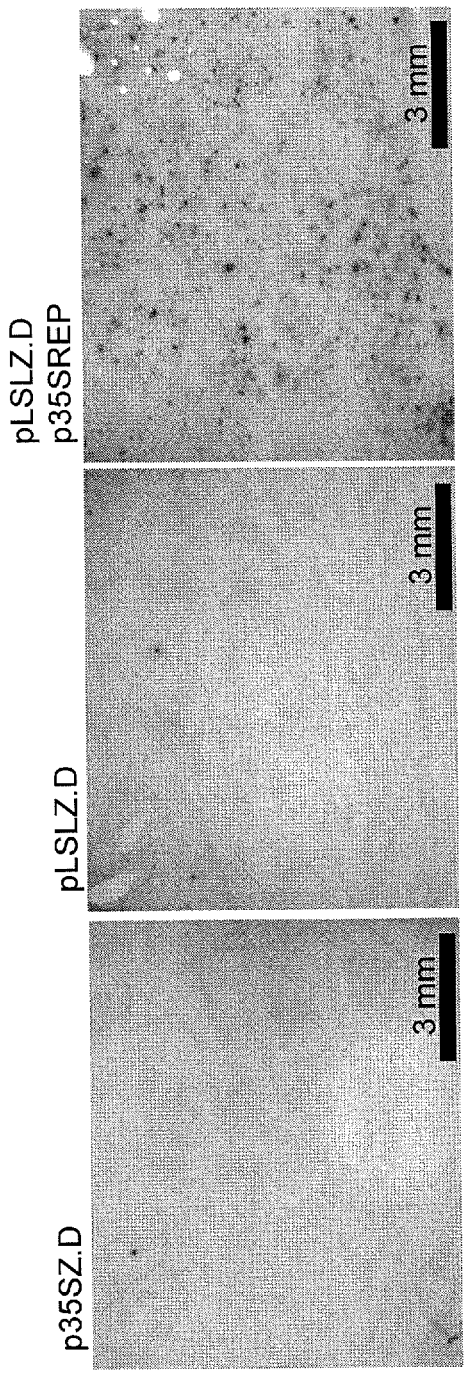
FIG. 22 shows selected images leaf tissue with GUS-expressing cells. To visualize cells expressing functional GUS protein, leaf tissue was stained in X-Gluc solution for 24 to 48 hours at 37° C., and chlorophyll was removed. Images shown are selected examples from tissue transformed with p35SZ.D (left), pLSLZ.D (center), and both pLSLZ.D and p35SREP (right).
Figure 23:
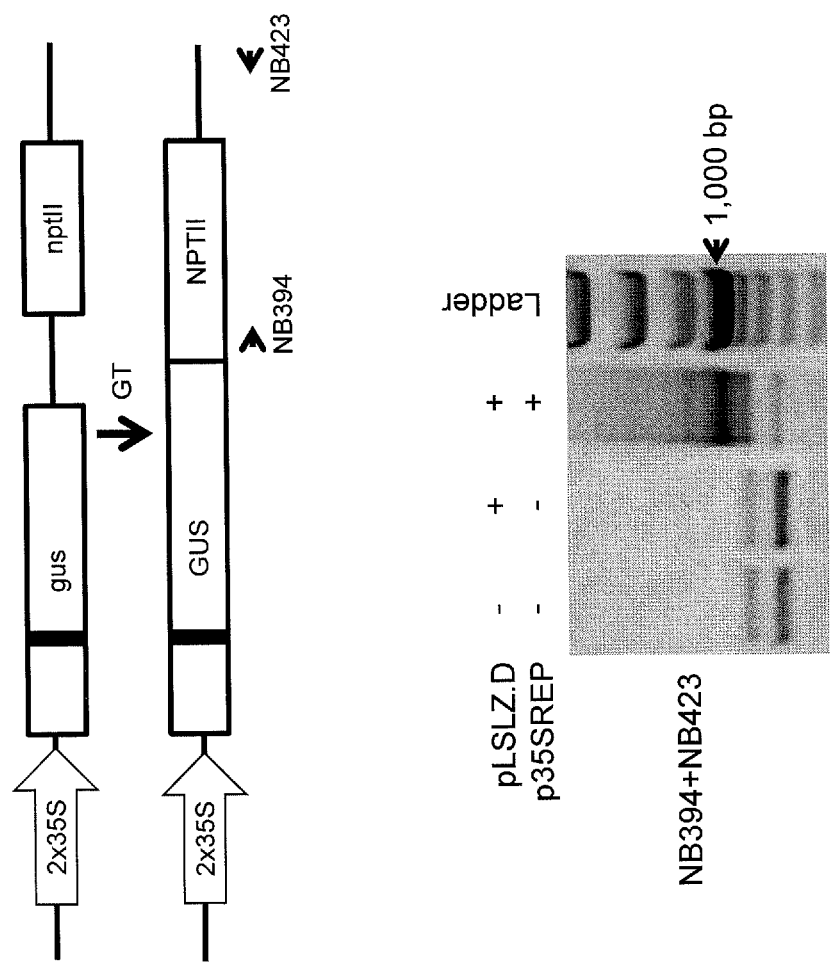
FIG. 23 is an image of a gel (bottom) from a PCR (top) designed to detect GUS::NPTII genes. PCR was performed on genomic DNA extracted from leaf tissue seven dpi. Primers were designed to be complementary to sequence downstream of the NPTII coding sequence and homologous to the sequence within the repair template (top). A high number of amplicons of the expected size (1.078 kb) were observed only from genomic DNA isolated from tissue transformed with pLSLZ.D and p35SREP.
Figure 24:
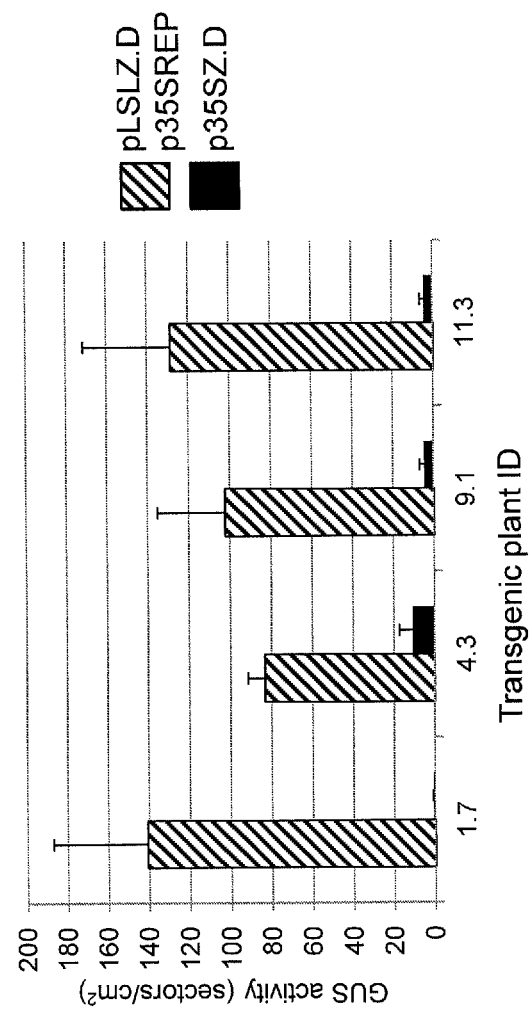
FIG. 24 is a graph plotting the density of GUS-expressing cells across multiple transgenic lines (identified as 1.7, 4.3, 9.1, and 11.3). Error bars represent SEM of at least three biological replicates.

GVRs were assessed for their ability to achieve GT through the coordinated delivery of nucleases and repair templates. The target for modification was the defective gus::nptII gene, which can be repaired by correcting a 600 bp deletion that removes part of the coding sequences of both GUS and NPTII. Following Zif268::FokI in pLSLZ.D is a us::NPTII repair template (FIG. 21). Cells having undergone GT will stain blue when incubated in a solution with the GUS substrate X-Gluc. Random integration of the repair template or read-through transcription from viral promoters should not produce functional GUS protein due to 703 nt missing from the 5' coding sequence. This was confirmed by delivering pLSLZ.D and p35SREP to non-transgenic leaf tissue; no GUS activity was observed (data not shown). To compare the performance of GVRs with the delivery of conventional T-DNA technology, a T-DNA vector was engineered to encode Zif268::FokI and a us:NPTII repair template (p35SZ.D). To this end, Multisite Gateway recombination was performed using plasmids pMDC32, pNB098 and pNB091. Due to the two-component design GVRs—requiring co-delivery of pLSLZD and p35SREP, a direct comparison of GT frequencies with p35SZD results in a performance bias, favoring the system that requires transfer of the least number of T-DNAs. While this may be an influencing factor, co-transformation of T-DNA in Nicotiana species is efficient (McCormac et al., Transgenic Res. 25:549-561, 2001), likely leading to minimal loss of performance with GVRs. Five to seven dpi, infiltrated leaf tissue was stained in X-Gluc and chlorophyll was removed. Relative to p35SZ.D, a substantial enhancement in the number of GUS-expressing cells in leaf tissue transformed with pLSLZD and p35SREP (FIG. 22) was observed. To molecularly verify repair of reporter gene coding sequences, PCR was performed using primers NB394 and NB423, which bind to sequence within the 600 bp modification and are complementary to sequence downstream of the homology encoded on the repair template. A 1,000 bp product, present only in the lane with p35SREP and pLSLZ.D suggested the presence of repaired reporter genes (FIG. 23). To quantify the relative enhancement of GT, the density of blue sectors was quantified from four transgenic plant lines (1.7, 4.3, 9.1, and 11.3). A significant enhancement in blue sectors with pLSLZ.D and p35SREP was observed across all four plant lines (FIG. 24) was observed. Table 2 indicates the total number of blue sectors in leaf tissue transgenic lines.

Exploring Elements of GVRs Necessary for High Frequency GT

Figure 25:
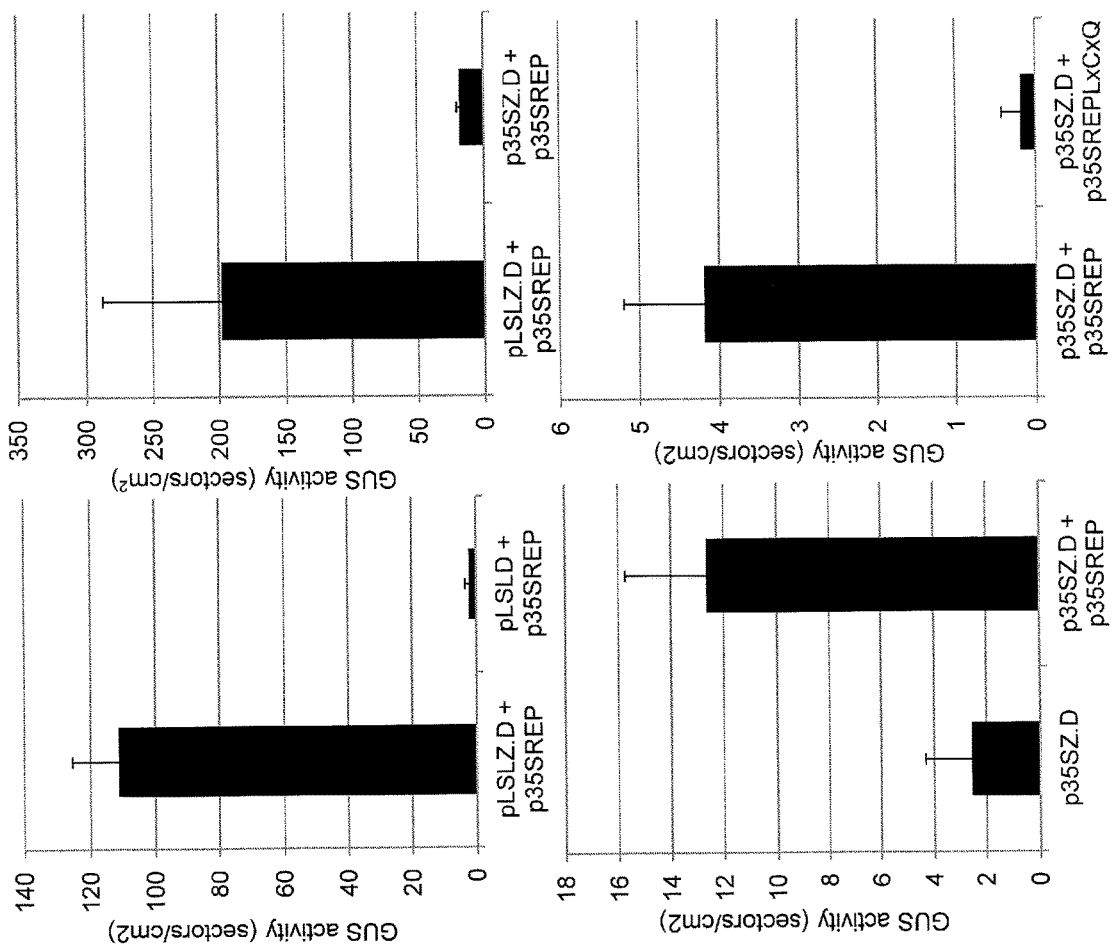
FIG. 25 is a series of graphs plotting the density of GUS-expressing cells with different transformed vectors. Error bars represent SEM of at least three biological replicates.
Figure 26:
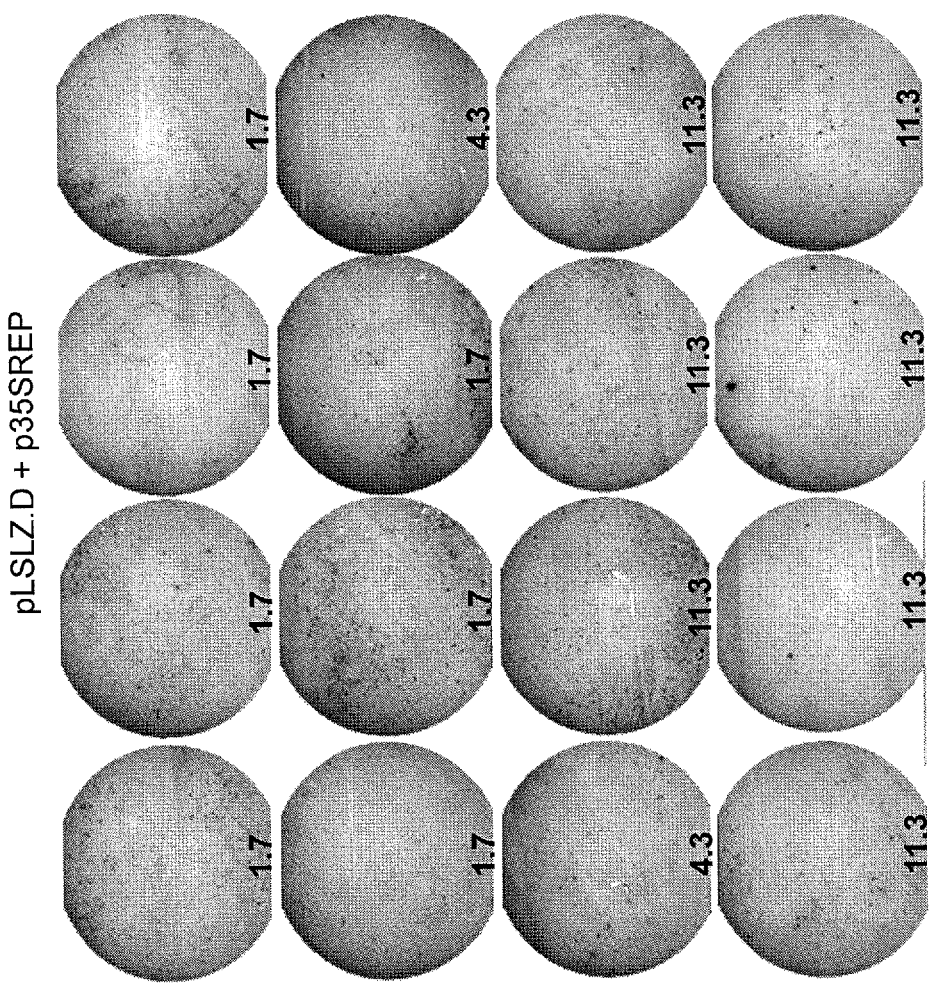
FIG. 26 is a series of images of leaf tissue with GUS-expressing cells following Agrobacterium-mediated delivery of pLSLZ.D and p35SREP to transgenic lines 1.7, 4.3, and 11.3, as indicated.
Figure 27:
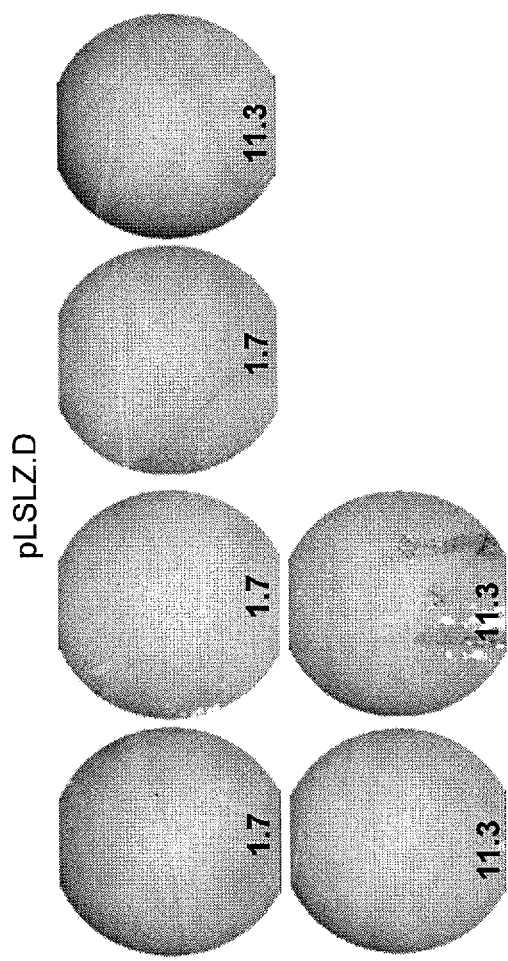
FIG. 27 is a series of images of leaf tissue with GUS-expressing cells following Agrobacterium-mediated delivery of pLSLZ.D to transgenic lines 1.7 and 11.3, as indicated.
Figure 28:
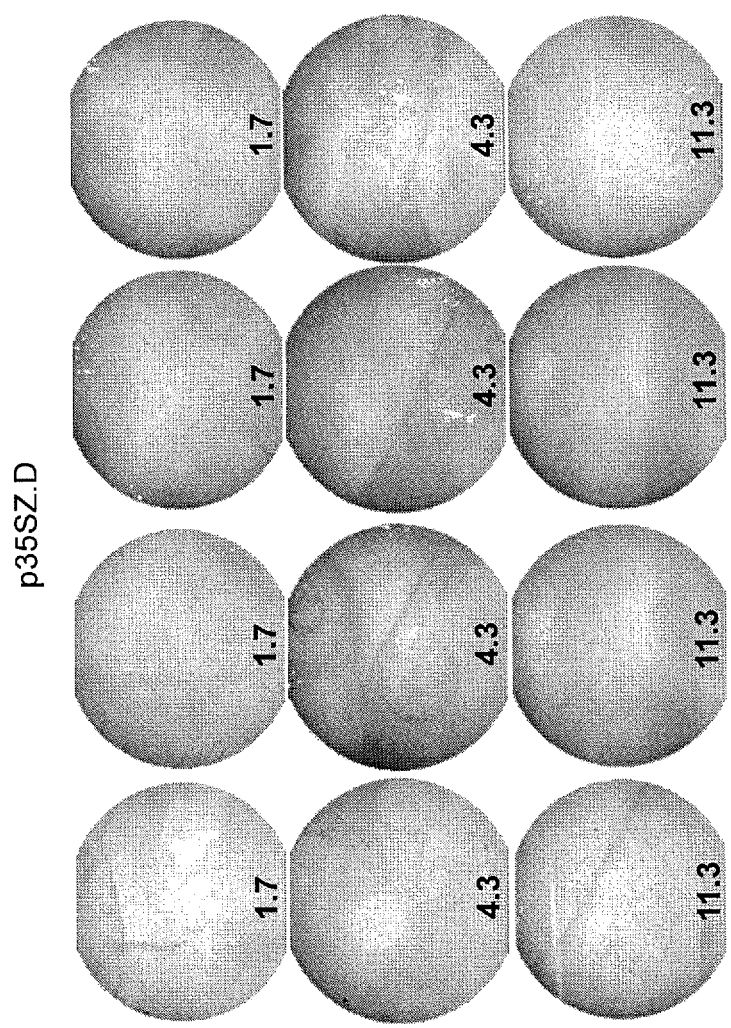
FIG. 28 is a series of images of leaf tissue with GUS-expressing cells following Agrobacterium-mediated delivery of p35SREP to transgenic lines 1.7, 4.3, and 11.3, as indicated.
Figure 29:
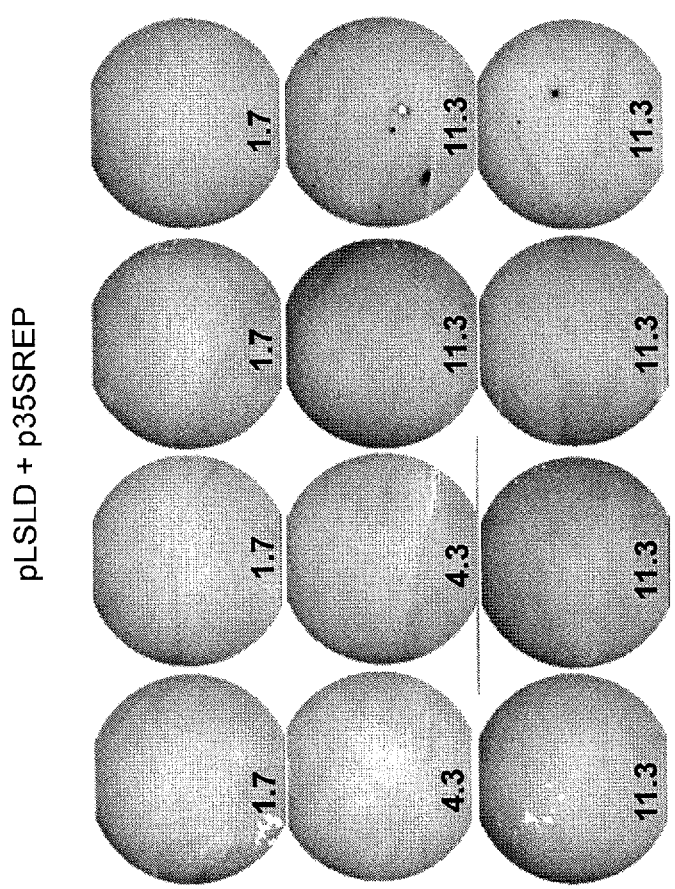
FIG. 29 is a series of images of leaf tissue with GUS-expressing cells following Agrobacterium-mediated delivery of pLSLD and p35SREP to transgenic lines 1.7, 4.3, and 11.3, as indicated.
Figure 30:
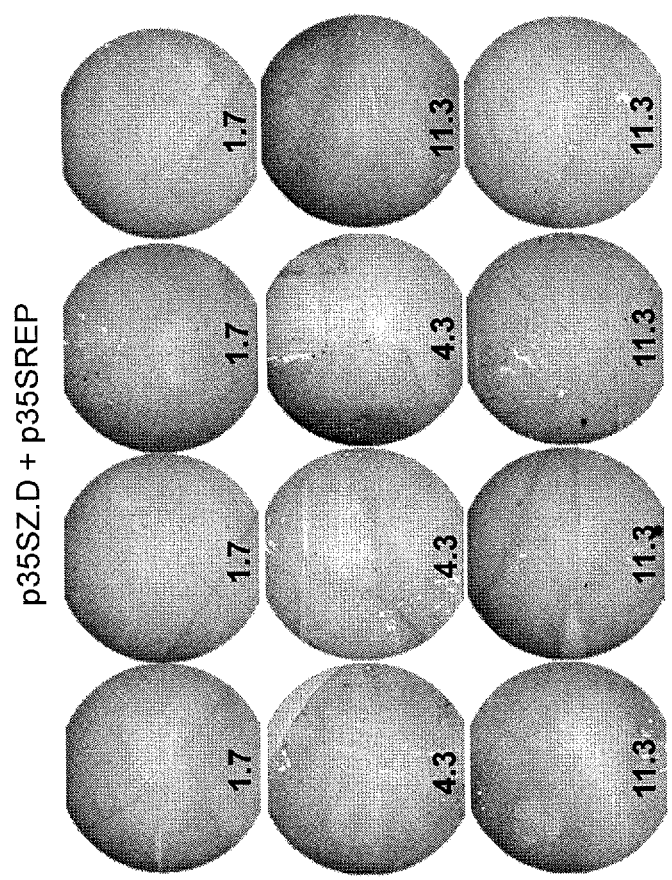
FIG. 30 is a series of images of leaf tissue with GUS-expressing cells following Agrobacterium-mediated delivery of p35SZ.D and p35SREP to transgenic lines 1.7, 4.3, and 11.3, as indicated.

There are several features of GVRs that may promote GT, including high levels of nuclease expression, high levels of repair template production and pleotropic Rep and RepA activity. To individually test these features, we paired two experimental samples on a single leaf to minimize variation caused by differences in leaf age and health, and quantified the density of blue sectors that result from GT. To determine the contribution of ZFN expression on GT, the coding sequence Zif268::FokI was replaced with GFP. Consistent with the stimulatory effect DSBs have on recombination, we observed a significant decrease in blue sectors when Zif268::FokI was removed (FIG. 25, top left). To determine if Rep-mediated replication of the GVRs contributes to GT, we compared the co-delivery of pLSLZ.D and p35SREP with the co-delivery of p35SZ.D and p35SREP. The decrease in blue sectors observed after removing the cis-acting LIR and SIR elements suggests that GVR replication contributes to enhanced rates of GT (FIG. 25, top right). Finally, to determine if there are pleotropic consequences of Rep and RepA expression on GT, we compared frequencies of GT using our standard T-DNA vector (p35SZ.D) with and without p35SREP. Here, we observed a significant increase in blue sectors when p35SREP was delivered, suggesting that pleotropic Rep and/or RepA activity promotes GT (FIG. 25, bottom left). See also FIGS. 26-30 for additional images of leaf tissue with GUS activity.

Mastrevirus RepA is known to interact with plant cell proteins, including the retinoblastoma-related protein pRBR. By sequestering pRBR's repressive activity against E2F, S-phase progression is promoted, providing the necessary factors for genome replication. One explanation for our results showing a pleotropic activity of replicase proteins on GT is that, in somatic leaf tissue, RepA promotes cell-cycle progression from G0/G1 to S phase and thereby provides improved cellular conditions for homologous recombination. To test this hypothesis, we introduced a single amino acid substitution within the conserved pRBR-interacting domain of RepA (designated LxCxQ) which reduces binding affinity to pRBR. A significant decrease in GT was observed when LxCxQ RepA T-DNA was delivered (FIG. 25, bottom right), suggesting that progression into S-phase stimulates GT.

Figure 31:
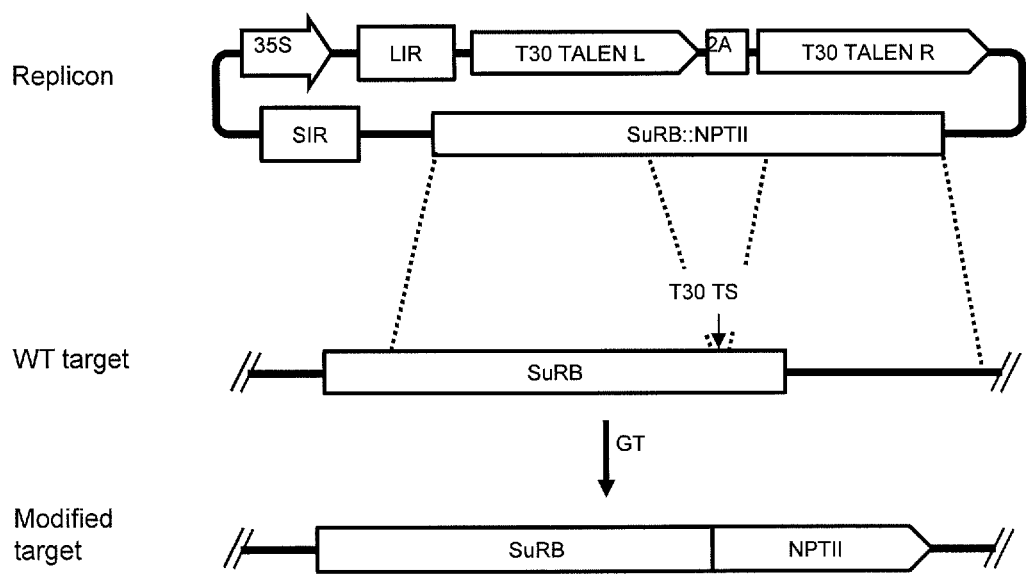
FIG. 31 is an illustration of the approach used to create a SuRB::NPTII fusion protein (top) and an image of two gels from PCRs designed to genotype candidate recombinant plants (bottom). Primers were designed to detect the 5' modification junction (5' check) and the 3' modification junction (3' check).
Figure 31:
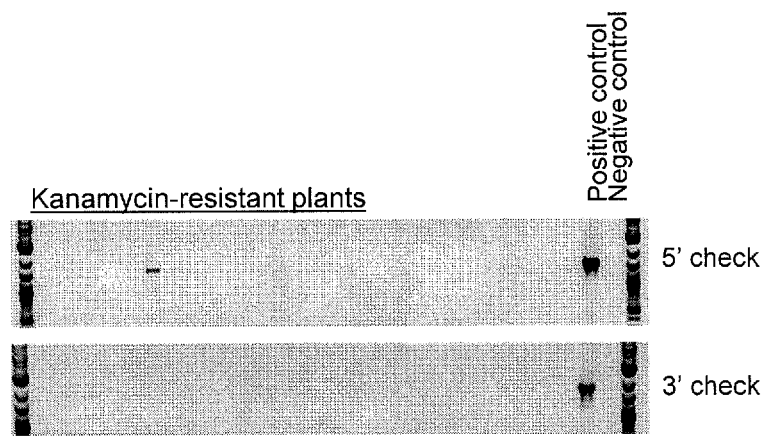

Demonstrating Methods for Regeneration of Recombinant *Nicotiana tabacum* Plants To regenerate modified *Nicotiana tabacum* plants, the leaf disc transformation protocol was implemented (Horsch et al., *Science* 227:1229-31, 1985). The target gene was the endogenous SuRB gene. A repair template, present downstream of the T30 TALEN pair on pLSLT, contained 1 kb of sequence homologous to the SuRB locus flanking NPTII coding sequence. As a consequence of GT, the NPTII coding sequence is placed in-frame with the SuRB coding sequence, resulting in the production of a SuRB::NPTII fusion protein. *Agrobacterium* containing pLSLT and p35SREP were grown overnight at 28° C. in LB with 50 μg/ml kanamycin and 50 μg/ml gentamycin. Cells were pelleted and resuspended to an $OD_{600}$ of 1 in LB. Leaf discs from WT tobacco plants were transferred into the *Agrobacterium* cultures for 10 minutes and then plated onto co-cultivation media as described elsewhere (Gallois and Marinho, *Methods Mol. Biol.* 49:39-48, 1995). Three days after transformation, discs were transferred to regeneration plates containing 50 μg/ml kanamycin and 1 mg/L 6-Benzylaminopurine. Shoots that appear about four weeks after transformation were assessed for the presence of the SuRB:NPTII fusion gene by PCR (FIG. 31). Amplification of a ~1.2 kb product (plant #6) suggests this plant was produced from a cell that has undergone GT. Amplification of the 5' junction may suggest that the GT event was 'one-sided' (e.g. following invasion of the repair template by a free 3' end of the chromosomal DNA, the NPTII sequence is copied and then the break is sealed by illegitimate recombination).

Demonstrating Replicational Release in Potato

Figure 32:
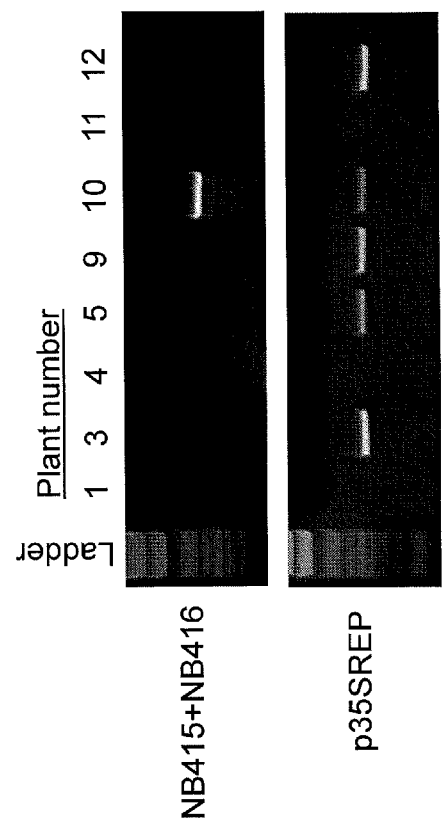
FIG. 32 is an image of a gel from a PCR designed to detect BeYDV-based GVRs in potato cells. Genomic DNA from plants co-transformed with p35SREP and pLSLGFP was evaluated for replicational release (top), and for the presence of Rep/RepA nucleotide sequence (bottom).
Figure 33:
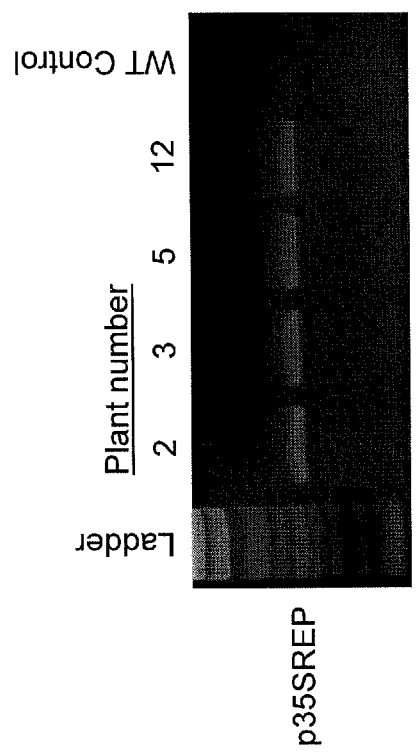
FIG. 33 is an image of a gel from a PCR designed to detect Rep/RepA RNA transcripts in potato plants transformed with p35SREP.

Functionality of BeYDV replicons in economically-valuable crops was investigated. To this end, experiments were first undertaken to demonstrate replicational release in potato cells (*Solanum tuberosum* cultivar Deseree). Potato leaf tissue was excised from aseptically-growing plants, and co-transformed with *Agrobacterium* containing p35SREP and pLSLGFP. Following co-transformation, leaf tissue was plated on cocultivation media for 2 days to allow for T-DNA transfer and integration. Leaf tissue was then washed in MS media containing 250 μg/mL cefotaxime, and plated on regeneration media containing 50 μg/mL hygromycin. Genomic DNA from several lines of hygromycin-resistant potato plants (Line 1, 3, 4, 5, 9, 10, 11, 12) was isolated and assessed for the presence of p35SREP T-DNA and circular replicons. Amplification of a 440 bp sequence from Rep/RepA and a 714 bp sequence from replicon nucleotide sequence from plant line 10 suggests GVRs are present in potato cells (FIG. 32). Interestingly, expression of Rep/RepA does not elicit an observable hypersensitive response. This was demonstrated by verifying expression of Rep/RepA in phenotypically-normal hygromycin-resistant plants by RT-PCR using primers that detect Rep/RepA RNA sequence (FIG. 33).

Figure 34:
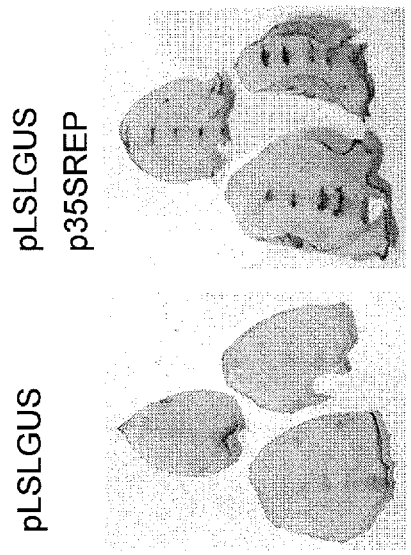
FIG. 34 is a pair of images of potato leaves expressing GUS enzyme. Potato leaves were transformed with *Agrobacterium* containing pLSLGUS (left) or a mixture of *Agrobacterium* containing pLSLGUS and p35SREP (right). Leaf tissue was stained in X-Gluc solution and chlorophyll was removed.
Figure 35:
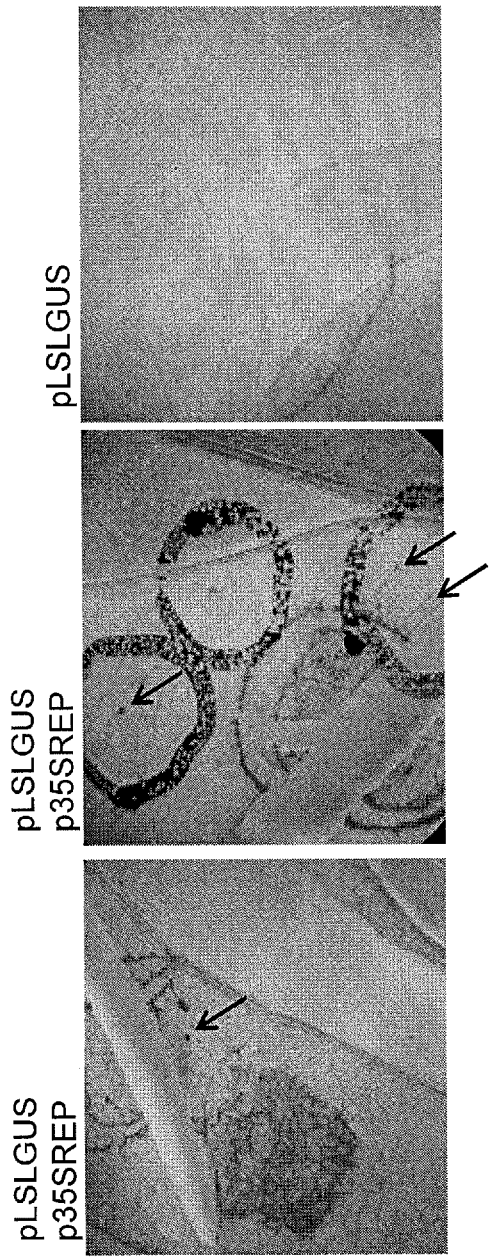
FIG. 35 is a series of images of tomato leaf tissue with GUS-expressing cells. Tomato leaf tissue was infiltrated with *Agrobacterium* containing pLSLGUS (right) or a mixture of *Agrobacterium* containing pLSLGUS and p35SREP (left and middle). To visualize cells expressing functional GUS protein, infected leaf tissue was stained in X-Gluc solution for 24 hours at 37° C., and chlorophyll was removed. Black arrows indicate areas of GUS activity.

Demonstrating Transient Delivery of Reporter Proteins in Tomato Leaf Tissue Using GVRs To demonstrate functionality of BeYDV-based GVRs in tomato (*Solanum lycopersicum* cv. M82), pLSLGUS and p35SREP were transformed into *Agrobacterium tumefaciens* (AGL1) by the freeze-thaw method. *Agrobacterium* was grown overnight at 28° C. to an $OD_{600}$ of 1 and diluted in LB media to an $OD_{600}$ of 0.2. Half leaves were fully infiltrated with *Agrobacterium* encoding pLSLGUS or coin-filtrated with pLSLGUS and p35SREP. To detect cells expressing GUS enzyme, leaf tissue was stained eleven dpi in X-Gluc solution. Chlorophyll was removed using 80% ethanol, and leaf images were taken (FIG. 34). The presence of GUS-expressing cells only in tissue transformed with pLSLGUS and p35SREP (FIG. 35) suggested GVRs can drive transient protein expression in tomato leaf tissue.

Figure 36:
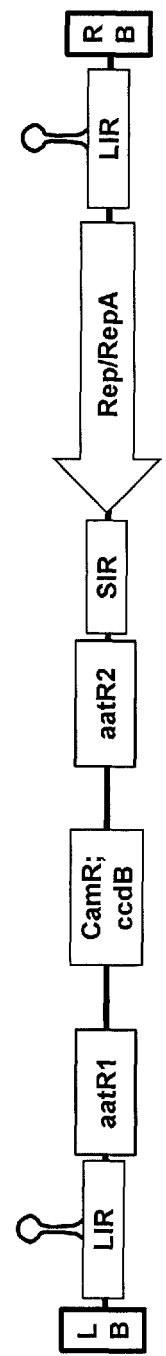
FIG. 36 is an illustration showing the general structure of the Wheat dwarf virus LSL T-DNA. Rep/RepA nucleotide sequence is present within the LIR elements. Rep/RepA gene expression is initiated from the complementary sense LIR promoter.
Figure 37:
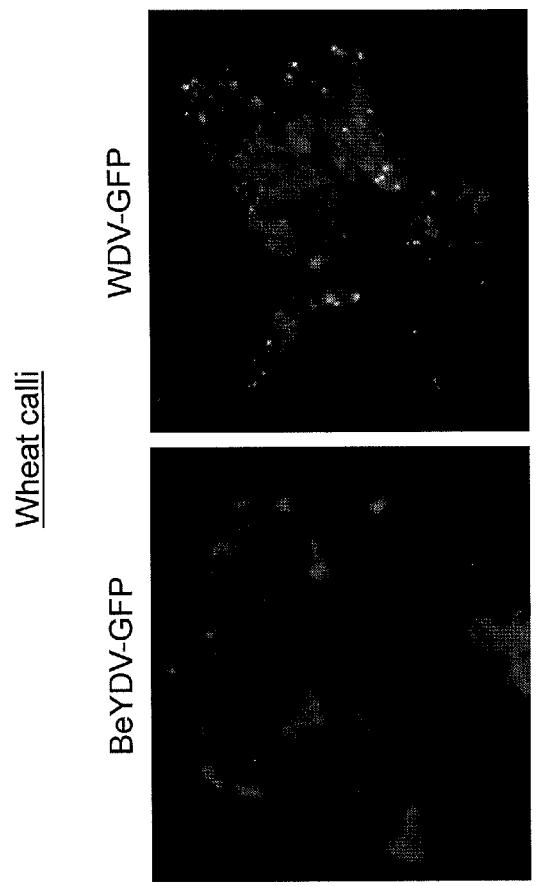
FIG. 37 is a pair of images of wheat calli tissue expressing GFP. GFP sequence was delivered to calli by particle bombardment of plasmid DNA containing BeYDV LSL sequences (left) or WDV LSL sequences (right). Images were taken three dpi.
Figure 38:
FIG. 38 is a set of images of *Setaria* calli expressing GFP. GFP sequence was delivered to calli by particle bombardment of plasmid DNA containing BeYDV LSL sequences (left) or WDV LSL sequences (right). Images were taken three dpi.
Figure 39:
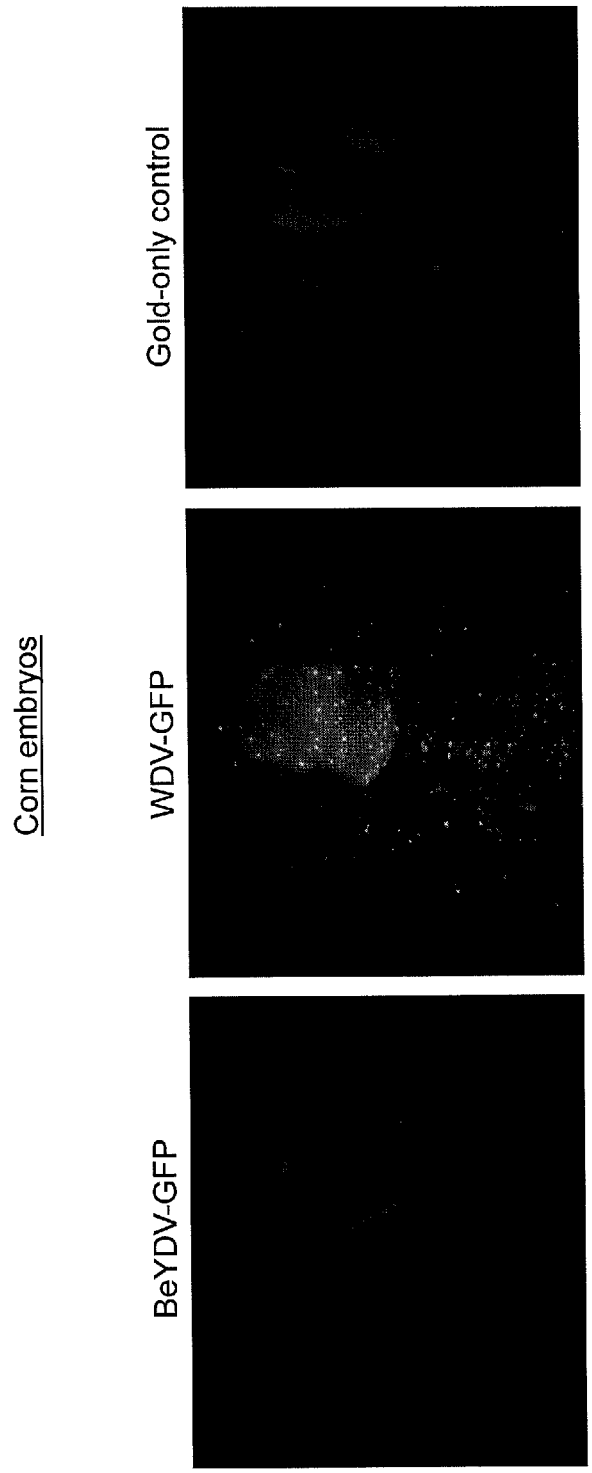
FIG. 39 is a set of images of corn embryos expressing GFP. GFP sequence was delivered to calli by particle bombardment of plasmid DNA containing BeYDV LSL sequences (left), WDV LSL sequences (middle), or control (right). Images were taken three dpi.

Demonstrating Functionality of Wheat Dwarf Virus Replicons in Wheat, *Setaria*, and Maize To expand the use of GVRs for genome editing in monocotyledonous plants, an LSL T-DNA was constructed with cis-acting replication sequences from the Wheat dwarf virus (WDV) (FIG. 36). Rep/RepA coding sequence was positioned inside the flanking LIR sequences, just downstream of the complementary sense LIR promoter. To demonstrate transient protein expression, WDV LSL plasmids containing the GFP gene (WDV-GFP) were delivered to wheat (*Triticum aestivum* cultivar Bobwhite), *Setaria* (*Setaria viridis*) and maize (*Zea mays* cultivar A188), by particle bombardment. Three days post bombardment, tissue was assessed for GFP expression. Enhanced expression of GFP was observed in wheat calli (FIG. 37), *Setaria* calli (FIG. 38), and corn embryos (FIG. 39) when delivered WDV-GFP. One explanation for these results may be that WDV replicons are replicating and promoting GFP expression.

Demonstrating GT in Rice Using WDV Replicons

Figure 40:
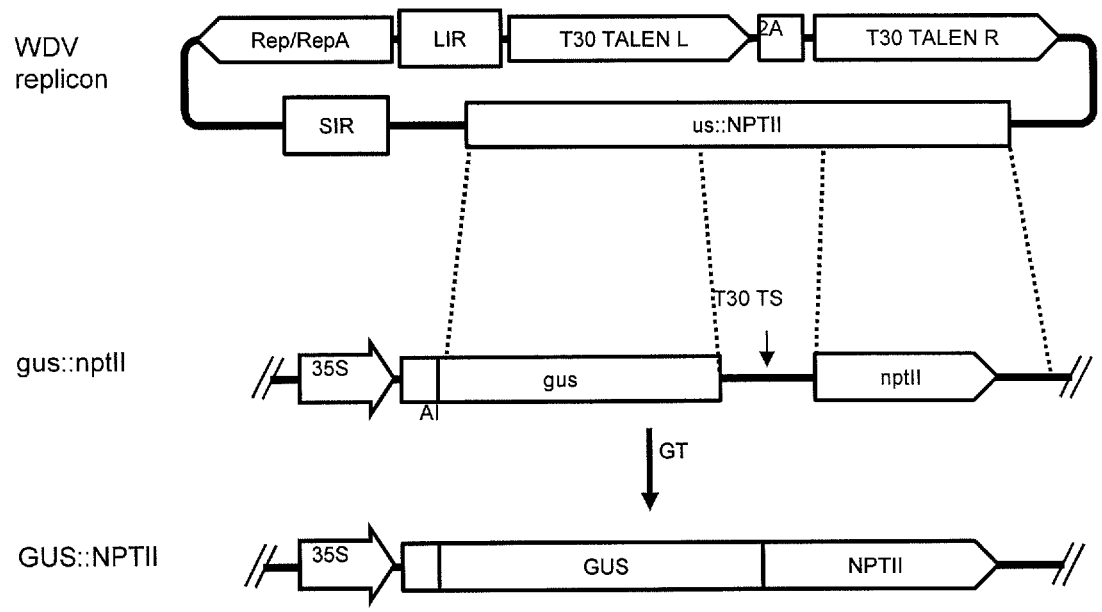
FIG. 40 is an illustration describing an approach to correct a non-functional gus::nptII reporter gene in rice (top) and pictures of GUS activity in rice leaves (bottom).
Figure 40:
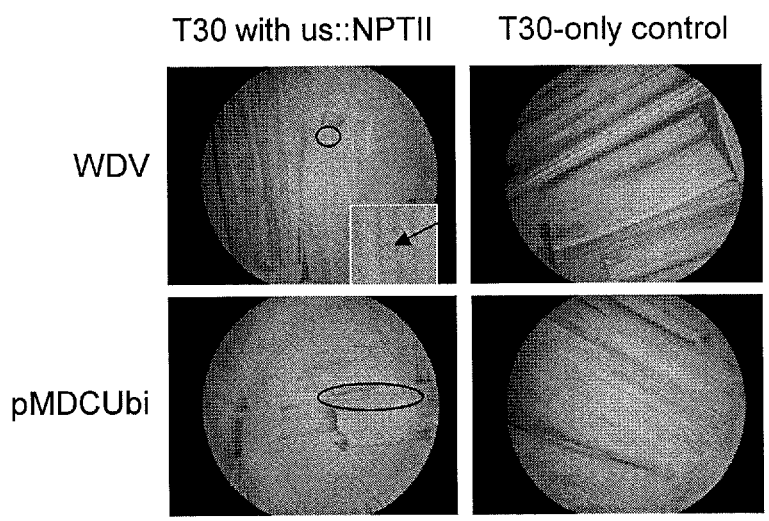

To determine if WDV can facilitate the delivery of TALENs and repair templates for GT in rice, a WDV replicon was engineered to contain the T30 TALEN pair followed by a repair template designed to correct the non-functional gus::nptII gene (FIG. 40, top). Leaf tissue from transgenic rice plants, containing a stably integrated gus::nptII gene, was exposed to *Agrobacterium* containing WDV T-DNA plasmids with or without repair template sequence. Transformation conditions were performed as previously described by Andrieu et al. (*Rice*, 5:23, 2012). Leaf tissue also was transformed with conventional T-DNA containing the T30 TALEN pair followed by the us::NPTII repair template. Blue sectors observed in leaf tissue delivered GVR T-DNA and conventional T-DNA suggests that gus::nptII gene function was restored through GT in a subset of leaf cells (FIG. 40, bottom).

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

| Primer | Sequence | SEQ ID NO |
|---|---|---|
| NB104 | gcggtaccctcgagtctagatctgtcttttccaaatatttattg | 2 |
| NB105 | gcggtaccctcgagtctagattttgtggtggttgcagc | 3 |

TABLE 1 -continued

| Primer | Sequence | SEQ ID NO |
|---|---|---|
| NB106 | gcggtaccctcgagtctagacaagattctcttcacttctc | 4 |
| NB112 | aggctagcgagctcagatctccttgtcaagaggagcatc | 5 |
| NB113 | aggctagcgagctcagatcttttgccattaatggagaatcttg | 6 |
| NB114 | aggctagcgagctcagatctcaatgacgacactccccac | 7 |
| NB128 | gcatgcagtactgagctcgccgaagatacgtggaaac | 8 |
| NB129 | gagctcagtactgcatgcgctggagggtaatagaaac | 9 |
| NB153 | gattaggctagcgagctcagatct | 10 |
| NB154 | cggacagattattcgatgcaaagg | 11 |
| NB155 | gacaaaccacaactgacaatacaga | 12 |
| NB158 | gcggtaccctcgagtctaga | 13 |
| NB161 | tcaccatcgtgaatcatccctcct | 14 |
| NB177 | tcgagtctagacacaatcacacaaaactaacaaaag | 15 |
| NB178 | gctcagatctgcaccaagaccaaaaatggcaac | 16 |
| NB207 | gcatgcagtactgagctcacgtggaaacaacggtgtttg | 17 |
| NB208 | gagctcagtactgcatgctaatagaaacactaatcttc | 18 |
| NB257 | tgccacgtggacgaatactagcaa | 19 |
| NB258 | gcttgaatcatggcctgaacgctt | 20 |
| NB263 | gagctcagtactgcat | 21 |
| NB264 | gcatgcagtactgagc | 22 |
| NB271 | ttacggttttcaccgaagttcat | 23 |
| NB272 | ttcggtgaaaaaccgtaaaccgacctgtccggtgccctg | 24 |
| NB274 | actgatctagacactggcggaagcaacgcgta | 25 |
| NB275 | tcagtagatctgccatgatggatactttctcg | 26 |
| NB307 | gccatgatggatactttctcg | 27 |
| NB314 | caacttttgtatacaaagttggcattataaaaaagcattgctcatcaatttgttgcaacgaacag gtcactatcagtcaaaataaaatcattatt | 28 |
| NB315 | aagctcgggcccaataatgatttttatttttg | 29 |
| NB316 | ctttgtatacaaaagttgccgagctcgcggccgcattaggcaccccag | 30 |
| NB317 | aactttgtacaagaaagctgggtcgtcgacctgcagactggctgtg | 31 |
| NB318 | aggaagtgagacgaaatttaataacggcgagatataaacttttaataggacgtccgatcgttcaaa catttggcaataaagtttcttaagattgaatcctgttgccggtcttgcgatgattatcatataat ttctgttgaattacgttaagcatgtaataattaacatgtaatgcatgacgttatttatgagatgg gttttttatgattagagtcccgcaattatacatttaatacgcgatagaaaacaaaatatagcgcgc aaactaggataaattatcgcgcgcggtgtcatctatgttactagatcgggaattgatcccccctc gacagcttccggaaagggcgaattcgcaactttgtatacaaaagttgaacgagaaacgtaaaatg atataaatatcaatatattaaattagattttgcataaaaaacagactacataatactgtaaaaca caacatatccagtcactatgccatccagctgatatccctat | 32 |
| NB319 | cgacggccagtcttaagctcgggcccaataatgatttttatttttgactgatagtgacctgttcg ttgcaacaaattgatgagcaatgcttttttataatgccaactttgtacaaaaaagcaggctccga attcatgccttctgctagtaagaacttcagactccaatctaaatatgttttccttacctatccca agtgctcatctcaaagagatgatttattccagtttctctgggagaaactcacacctttttcttatt ttcttccttggtgttgcttctgagcttcatcaagatggcactacccactatcatgctcttctcca gcttgataaaaaccttgtatagggatccttatttttcgattttgaaggaaatcaccctaatat ccagccagctagaaactcctaaacaagtccttgattacatatcaaaggacggagatattaaacca gaggagatttccgagatcataaggtctctcctcgcaaatctgac | 33 |
| NB320 | attaaaaccagaggagatttccgagatcataaggtctctcctcgcaaatctgacgcacgatggag aactattatccagactgcaacgtctaaggaggaatatccttgacatgatcaaggaagaattccctc | 34 |

TABLE 1 -continued

| Primer | Sequence | SEQ ID NO |
|---|---|---|
|  | atgaatgggcaacaaagcttcaatggctggaatattcagccaacaaattattccctccacaacct gaaccgtatgtgtcgcccttcacagaatcagatcttcgctgccacgaagatctacactcctggag ggaaacccatctataccatgtaagcatagacgcttatacttacatacatcctgtctcataccaac aagctcaatctgaccttgaatggatggccgatttaaccaggacaatggaaggaatggaatccgac accccagcctctacatctgcggaccaactcgtaccggaaagaccacctgggctagaagtctcgga cgacacaactattggaacggtaccatcgatttcaccaactacgat |  |
| NB321 | attaaaaccagaggagatttccgagatcataaggtctctcctcgcaaatctgacgcacgatggag aactattatccagactgcaacgtctaaggaggaatatcttgacatgatcaaggaagaattccctc atgaatgggcaacaaagcttcaatggctggaatattcagccaacaaattattccctccacaacct gaaccgtatgtgtcgcccttcacagaatcagatcttcgctgccacgaagatctacactcctggag ggaaacccatctataccatgtaagcatagacgcttatacttacatacatcctgtctcataccaac aagctcaatctgaccttgaatggatggccgatttaaccaggacaatggaaggaatggaatccgac accccagcctctacatctgcggaccaactcgtaccggaaagaccacctgggctagaagtctcgga cgacacaactattggaacggtaccatcgatttcaccaactacgat | 35 |
| NB322 | gtaccggaaagaccacctgggctagaagtctcggacgacacaactattggaacggtaccatcgat ttcaccaactacgatgaacacgccacctataatatcatcgacgacatccccttcaagttcgtccc attgtggaagcaattaataggttgccagtctgatttcactgtcaaccctaaatatggaaaaaaga agaaaataaaaggtgggatcccttctataattctttgcaatcctgacgaagactggatgttatca atgacaagtcaacagaaggattactttaaagataattgcgtcacccactacatgtgtgacgggga gactttttttgctcggaatcgtcgagtcactgaacgtgcctgaattcgacccagctttcttgta caaagttggcattataaaaaataattgctcatcaatttgttgcaacgaacaggtcactatcagtc aaaataaaatcattatttgccatccagctgatatcccctatagtg | 36 |
| NB323 | cgacggccagtcttaagctc | 37 |
| NB324 | cactatagggatatcagct | 38 |
| NB325 | agcttggtacccctgcaggtagcagaaggcatg | 39 |
| NB326 | ataagcacaagttttatccggc | 40 |
| NB327 | ggatcctctagattacgcccgcctgc | 41 |
| NB328 | cgtaatctagaggatccggcttactaaaagc | 42 |
| NB329 | tgttgaccgagctcctgcagaagcttctcgag | 43 |
| NB330 | cctgcaggtagcagaaggcatgttgttgtgactccgaggggttgcctcaaactctatcttataac cggcgtggaggcatggaggcaggggtattttggtcattttaatagatagtggaaaatgacgtgga atttacttaaagacgaagtcgagacctttgcgactctagaggtctcaaatttaatattaccggcg tggcccccccttatcgcgagtgctttagcacgagcggtccagatttaaagtagaaaatttcccgc ccactagggttaaaggtgttcacactataaaagcatatacgatgtgatggtatttgatggagcgt atattgtatcaggtatttccgttggatacgaattattcgtacgaccctccctaagattcttgatt gtttataaaaccaaatctcattgtctttgttgtgtattgtttgcaggacgtcgagagttctcaac acaacatatacaaaacaaacgaatctcaagca | 44 |
| NB331 | acaaaacaaacgaatctcaagcaatcaagcattctacttctattgcagcaatttaaatcatttct acaagtttgtacaaaaaagctgaacgagaaacgtaaaatgatataaatatcaatatattaaatta gattttgcataaaaaacagactacataatactgtaaaacacaacatatccagtcactatggcggc cgcattaggcaccccaggcttttacactttatgcttccggctcgtataatgtgtggattttgagtt aggatccgtcgagattttcaggagctaaggaagctaaaatggagaaaaaaatcactggatatacc accgttgatatatcccaatggcatcgtaaagaacattttgaggcatttcagtcagttgctcaatg tacctataaccagaccgttcagctggatattacggccttttaaagaccgtaaagaaaataagc acaagttttatccggcctttattcaca | 45 |
| NB332 | ctatggtcgacctgcagactggctgtg | 46 |
| NB333 | gggatcccactcgagggtcaacatggtggagcacg | 47 |
| NB334 | ctagagtcgaggtcctctcca | 48 |
| NB335 | aggtggctcctacaaatgccatcattgcgataaaggaaaggccatcgttgaagatgcctctgccg acagtggtcccaaagatggaccccaccacgaggagcatcgtggaaaaagaagacgttccaacc acgtcttcaaagcaagtcggattgatgtgatatctccactgacgtaagggatgacgcacaatccca ctatccttcgcaagaccccttcctctatataaggaagttcatttcatttggagaggacctcgactc tagccttcctctatataaggaagttcatttcatttggagaggtaagtttcacttcacacattatt actgtcttctaatacaaggttttttatcaagctgggaagaagcatgatagtgggtagtgccatct tgatgaagctcagaagcaacaccaaggaagaaaataagaaaaggtgtgagtttctcccagagaaa ctgaataaatcatctctttgagatgagcacttgggataggtaag | 49 |
| NB336 | tgagatgagcacttgggataggtaaggaaaacatatttagattggagtctgaagttcttactagc agaaggcatgttgttgtgactccgaggggttgcctcaaactctatcttataacggcgtggaggc atgaggcaggggtattttggtcattttaatagatagtggaaaatgacgtggaatttacttaaag acgaagtcgagacctttgcgactctagaggtctcaatttaatattaccggcgtggcccccctta tcgcgagtgctttagcacgagcggtccagatttaaagtagaaaatttcccgcccactagggttaa aggtgttcacactataaaagcatatacgatgtgatggtatttgatggagcgtatattgtatcagg | 50 |

TABLE 1 -continued

| Primer | Sequence | SEQ ID NO |
|---|---|---|
|  | tatttccgttggatacgaattattcgtacgaccctcatagtttaaactgaaggcgggaaacgaca atctgatccaagctcaagctaagcttgcatgcctgcaggatatcg |  |
| NB337 | cgatatcctgcaggcatgcaagcttagc | 51 |
| NB338 | aagtctttgcgacaagggggggcccacgccg | 52 |
| NB339 | aattcggcgtgggccccccttgtcgcaaag | 53 |
| NB344 | cacagccagtctgcaggtcgaccatagtgactggatatgttgtgttttacagtattatgtagtct gttttttatgcaaaatctaatttaatatattgatatttatatcattttacgtttctcgttcagat tcttgtacaaagtggtgagtgtacttcaagtcagtgggaaatcaataaaatgattattttatgaa tatatttcattgtgcaagtagatagaaattacatatgttacataacacacgaaataaacaaaaaa agacaatccaaaaacaaacaccccaaaaaaaataatcactttagataaactcgtatgaggagagg cacgttcagtgactcgacgattcccgagcaaaaaaagtctccccgtcacacatgtagtgggtgac gcaattatctttaaagtaatccttctgttgacttgtcattgataacatccagtcttcgtcaggat tgcaaagaattatagaagggatcccactcgagaagcttctgcag | 54 |
| NB362 | acctcgactctagaatgaagactaatctttttctctttc | 55 |
| NB363 | gaacgatcggacgtcttaaagctcatcatgtttgtatag | 56 |
| NB379 | gcccttcaccatggcttcctccctccaaagaaaaag | 57 |
| NB380 | gaacgatcggacgtcctattaaaagtttatctcaccgtta | 58 |
| NB394 | tgccgccgtgttccggctgtcagc | 59 |
| NB396 | aaggtgcacgggaatatttcgcgc | 60 |
| NB415 | gtttcacttcacacattattactg | 61 |
| NB416 | tgttgagaactctcgacgtcctgc | 62 |
| NB422 | gtgtgaacaacgaactgaactggc | 63 |
| NB423 | agagcgcccaatacgcaaaccgc | 64 |
| NB424 | cagcgagtcagtgagcgaggaagc | 65 |
| NB448 | agctagtctagaatgttacgtcctgtagaaacc | 66 |
| NB449 | gtacgtgacgtctcattgtttgcctccctgc | 67 |
| NB478 | gacggtgcagaaagtgaagta | 68 |
| NB479 | tatgggcccaggagtgtctaa | 69 |
| NB488 | caagctaagcttgcatgcctgcagggtgtttgacaggatatattggcg | 70 |
| NB489 | tccatgccgcctcctttagc | 71 |
| NB490 | gctaaaggaggcggcatgga | 72 |
| NB491 | accacttcaagaactctgtagc | 73 |
| NB492 | gctacagagttcttgaagtggtg | 74 |
| NB493 | aggcacgttcagtgactcgacgaagtagatgccgaccggatctgtcg | 75 |
| NB494 | gaagttcttactagcagaaggcatcggatctgcgaaagctcgagag | 76 |
| NB495 | gtcacaacaacatgccttctgctacctgcaggcgtaatcatggtcatagc | 77 |

TABLE 2

| Delivered T-DNA: | p35SZ.D | | | | pLSLZ.D + p35SREP | | | | pLSLD + p35SREP | | |
|---|---|---|---|---|---|---|---|---|---|---|---|
| Transgenic plant line ID: | 1.7 | 4.3 | 9.1 | 11.3 | 1.7 | 4.3 | 9.1 | 11.3 | 1.7 | 4.3 | 11.3 |
| Leaf 1 (blue sectors/cm²) | 0.00 | 1.85 | 0.93 | 0.56 | 479.26 | 85.37 | 218.89 | 372.96 | 0.19 | 7.41 | 1.11 |
| Leaf 2 (blue sectors/cm²) | 1.48 | 7.78 | 13.89 | 2.96 | 160.93 | 96.67 | 77.22 | 147.96 | 0.00 |  | 0.00 |
| Leaf 3 (blue sectors/cm²) | 0.93 | 22.96 | 0.00 | 1.48 | 170.19 | 68.15 | 120.37 | 61.67 |  |  | 2.04 |
| Leaf 4 (blue sectors/cm²) |  |  | 0.74 | 1.11 | 287.22 |  | 25.00 | 38.15 |  |  | 2.22 |
| Leaf 5 (blue sectors/cm²) |  |  | 1.11 | 6.11 | 101.48 |  | 70.37 | 109.07 |  |  |  |

TABLE 2-continued

| | | | | | | | | | |
|---|---|---|---|---|---|---|---|---|---|
| Leaf 6 (blue sectors/cm²) | | 10.00 | 13.33 | 90.74 | | | 96.48 | | |
| Leaf 7 (blue sectors/cm²) | | | | 36.67 | | | 74.63 | | |
| Leaf 8 (blue sectors/cm²) | | | | 27.96 | | | | | |

| Delivered T-DNA: | pLSLZ.D | | | p35SZ.D + p35SREP | | | p35SZ.D + p35SREPLxCxQ | | |
|---|---|---|---|---|---|---|---|---|---|
| Transgenic plant line ID: | 1.7 | 9.1 | 11.3 | 1.7 | 4.3 | 9.1 | 11.3 | 1.7 | 9.1 | 11.3 |
| Leaf 1 (blue sectors/cm²) | 7.04 | 47.96 | 5.00 | 16.11 | 19.26 | 4.26 | 67.41 | 3.89 | 0.00 | 0.00 |
| Leaf 2 (blue sectors/cm²) | | 7.04 | | 16.48 | | | 19.81 | 0.93 | | |
| Leaf 3 (blue sectors/cm²) | | 0.93 | | 6.67 | | | 7.04 | 0.00 | | |
| Leaf 4 (blue sectors/cm²) | | | | 23.15 | | | | 0.00 | | |
| Leaf 5 (blue sectors/cm²) | | | | 3.70 | | | | 0.00 | | |
| Leaf 6 (blue sectors/cm²) | | | | 2.22 | | | | | | |
| Leaf 7 (blue sectors/cm²) | | | | 11.11 | | | | | | |
| Leaf 8 (blue sectors/cm²) | | | | 0.19 | | | | | | |
| Leaf 9 (blue sectors/cm²) | | | | 0.93 | | | | | | |
| Leaf 10 (blue sectors/cm²) | | | | 8.15 | | | | | | |

What is claimed is:

1. A method for modifying the genetic material of a plant cell, the method comprising:
  (a) introducing into the cell a bean yellow dwarf virus vector comprising a repair template that is heterologous to the virus and is targeted to a first sequence that is endogenous to the plant cell, wherein the plant cell is a soybean plant cell; and
  (b) inducing a double strand break at or near the sequence to which the repair template is targeted, wherein said double strand break is generated by an endonuclease targeted to a second endogenous plant sequence at or near the first sequence that is targeted by the donor sequence,
  wherein the bean yellow dwarf virus vector comprises a sequence encoding said endonuclease,
  wherein the endonuclease is a transcription activator-like effector nuclease;
  wherein the bean yellow dwarf virus vector is a deconstructed vector that further encodes the proteins needed for viral replication, wherein said deconstructed vector does not generate a productive infection, and
  wherein homologous recombination occurs between the first endogenous plant sequence and the donor sequence.

2. The method of claim 1, wherein the endonuclease is encoded by a transgene sequence stably integrated into the genetic material of the plant, or is expressed transiently.

3. The method of claim 2, wherein the transgene encoding the endonuclease is operably linked to a promoter that is constitutive, cell specific, inducible, or activated by alternative splicing of a suicide exon.

4. The method of claim 1, further comprising:
  (c) cultivating the cell on a medium to regenerate a plant.

5. The method of claim 1, further comprising:
  (c) incubating the cell in a growth chamber to generate a plant.

6. The method of claim 1, further comprising:
  (c) recovering a plant that comprises the donor sequence.

* * * * *